US012686892B2

(12) United States Patent
Karlikow et al.

(10) Patent No.: US 12,686,892 B2
(45) Date of Patent: Jul. 21, 2026

(54) MOLECULAR SENSING PLATFORM AND METHODS OF USE

(71) Applicant: THE GOVERNING COUNCIL OF THE UNIVERSITY OF TORONTO, Toronto (CA)

(72) Inventors: Margot Karlikow, Toronto (CA); Keith Pardee, Toronto (CA); Peivand Sadat Mousavi, Waterloo (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 1044 days.

(21) Appl. No.: 17/767,837

(22) PCT Filed: Oct. 9, 2020

(86) PCT No.: PCT/CA2020/051367
§ 371 (c)(1),
(2) Date: Apr. 8, 2022

(87) PCT Pub. No.: WO2021/068086
PCT Pub. Date: Apr. 15, 2021

(65) Prior Publication Data
US 2024/0093317 A1 Mar. 21, 2024

(30) Foreign Application Priority Data
Oct. 9, 2019 (GB) ...................................... 1914568

(51) Int. Cl.
*C12Q 1/6865* (2018.01)
*C12Q 1/6897* (2018.01)
*C12Q 1/70* (2006.01)

(52) U.S. Cl.
CPC ........... *C12Q 1/701* (2013.01); *C12Q 1/6865* (2013.01); *C12Q 1/6897* (2013.01)

(58) Field of Classification Search
None
See application file for complete search history.

(56) References Cited

U.S. PATENT DOCUMENTS

2017/0198302 A1 7/2017 Feng et al.

FOREIGN PATENT DOCUMENTS

| CN | 109880851 A | 6/2019 |
| WO | 2019089803 A1 | 5/2019 |
| WO | 2019104058 A1 | 5/2019 |
| WO | 2019126577 A3 | 7/2019 |

OTHER PUBLICATIONS

Pardee et al., Rapid, Low-Cost Detection of Zika Virus Using Programmable Biomolecular Components. Cell, 2016, 165: 1255-1266.*

Gootenberg et al. Nucleic acid detection with CRISPR-Cas13a/C2c2. Science 356, 438-442 (2017).*
Gootenberg et al. Multiplexed and portable nucleic acid detection platform with Cas13, Cas12a, and Csm6. Science 360, 439-444 (2018).*
Kellner, Max J. et al. SHERLOCK: nucleic acid detection with CRISPR nucleases. Nature Protocols, vol. 14, Oct. 2019, 2986-3012.
Li, Shi-Yuan et al. CRISPR-Cas 12a-assisted nucleic acid detection. Cell Discovery, 2018, 4:20.
Gan, Wupeng et al. A filter paper-based microdevice for low-cost, rapid, and automated DNA extraction and amplification from diverse sample types. Lab Chip, 2014, 14, 3719-3728.
Search Report issued for Application GB1914568.9 on Apr. 16, 2020.
Freije, Catherine A. et al. Programmable inhibition and detection of RNA viruses using Cas13. Mol Cell. Dec. 5, 2019; 76(5): 826-837.
Curtis, Kelly A. et al. Isothermal Amplification Using a Chemical Heating Device for Point-of-Care Detection of HIV-1. PLoS One. Feb. 2012, vol. 7, Issue 2, e31432.
Chen, Janice S. et al. CRISPR-Cas12a target binding unleashes indiscriminate single-stranded DNase activity. Science. Apr. 27, 2018; 360(6387): 436-439.
Pardee, Keith et al. Rapid, Low-Cost Detection of Zika Virus Using Programmable Biololecular Components. Cell 165, 1255-1266, May 19, 2016.
Schildkraut, Ezra et al. Advertorial: Single Guide, Simplified, EnGen sgRNA Synthesis Kit, S. pyogenes. May 1, 2017, vol. 37, No. 9. https://www.genengnews.com/magazine/293/advertorial-single-guide-simplified-engen-sgrna-synthesis-kit-s-pyogenes/.

(Continued)

*Primary Examiner* — Nianxiang Zou
(74) *Attorney, Agent, or Firm* — Smart & Biggar LP; Carmela De Luca

(57) ABSTRACT

Provided are signal-inducing CRISPR-sensitive nucleic acid, optionally DNA, sensors, for example comprising: a) a non-functional CRISPR-sensitive DNA reporter construct comprising a non-functional expression cassette with at least one CRISPR target site inserted, generated by removal or addition of nucleic acids or naturally present in the expression cassette, the non-functional expression cassette having a reporter construct upstream end upstream of the CRISPR target site and a reporter construct downstream end downstream of the CRISPR target site, and b) a function-restoring nucleic acid, the function-restoring nucleic acid comprising an upstream flanking end, a function restoring repair insert and a downstream flanking end, wherein the upstream flanking end interfaces with reporter construct upstream end and/or the downstream flanking end interfaces with the reporter construct downstream end and one or both of the flanking ends are capable of permitting insertion or ligation of the function restoring repair insert into/to the reporter construct when the CRISPR target site is actuated under sensing condition, thereby producing a functional DNA reporter construct and sensor signal. Also provided are cell free and cell based systems, kits, primer pairs and molecular barcodes and methods of use thereof.

11 Claims, 24 Drawing Sheets
Specification includes a Sequence Listing.

(56) References Cited

OTHER PUBLICATIONS

Teng, Fei et al. CDetection: CRISPR-Cas12b-based DNA detection with sub-attomolar sensitivity and single-base specificity. Genome Biology (2019) 20:132.

Yan, Lei et al. Isothermal amplified detection of DNA and RNA. Molecular BioSystems, 2014, 10, 970-1003.

Written Opinion issued for PCT/CA2020/051367 on Jan. 11, 2021 for.

Pardee, Keith et al. Paper-based Synthetic Gene Networks. Cell. Nov. 6, 2014; 159(4): 940-954.

Myhrvold, Cameron et al. Field-deployable viral diagnostics using CRISPR-Cas13. Science 360, 444-448 , Apr. 27, 2018.

Mousavi, Peivand Sadat et al. A Multiplexed, Electrochemical Interface for Gene Circuit-Based Sensors. Nat. Chem. Jan. 2020; 12(1): 48-55.

Linnes, Jacqueline C. et al. Paper-based molecular diagnostic for Chlamydia trachomatis. The Royal Society of Chemistry Advances, 2014, 4, 42245-42251.

Gootenberg, Jonathan S. et al. Nucleic acid detection with CRISPR-Cas13a/C2c2. Science, Apr. 28, 2017; 356(6336): 438-442.

Gootenberg, Jonathan S. et al. Multiplexed and portable nucleic acid detection patform with Cas13, Cas12a, and Csm6. Science. Apr. 27, 2018, 360(6387): 439-444.

* cited by examiner

Fig. 4

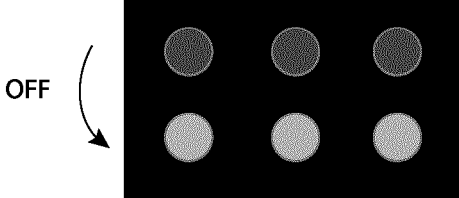

OFF

Without diagnostic target: functional DNA ==> purple color

With diagnostic target: non-functional DNA ==> yellow color

Fig. 5

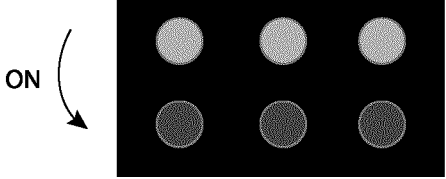

ON

Without diagnostic target: non-functional DNA ==> yellow color

With diagnostic target: functional DNA ==> purple color

Fig. 6 top

```
5'    GCGCTAATACGACTCACTATAGGGCGAAGTTCATATGCTCAACAAGGGCGCCGAGG    3'
      |-+-+-+-+-+-+-+-+-+-+-+-+-+-+-+-+-+-+-+-+-+-+-+-+-+-+-+-+-|
3'    CGCGATTATGCTGAGTGATATCCCGCTTCAAGTATACGAGTTGTTCCCGCGGCTCC    5'
              [    T7 promoter        >
``` bottom

```
5'    GCGCTAATACGACTCACTATAGGGCCCGGCGACACGGTCACCTTTATTCCAGTG    3'
      |-+-+-+-+-+-+-+-+-+-+-+-+-+-+-+-+-+-+-+-+-+-+-+-+-+-+-+-|
3'    CGCGATTATGCTGAGTGATATCCCGGGCCGCTGTGCCAGTGGAAATAAGGTCAC    5'
              [    T7 promoter        >
```

Fig. 7

5'- ATT TAA AGT TCT TAG ACT TTT AAC GGT AAC TTC CCA GTC ACG ACG TTG ATC TAC AAC AGT AGA AAT TAT TTA AAG TTC TTA GAC GGA TCA TAT CCT TGA TGG ATT CGA CAT TAT -3'

Nucleic acid input (RNA or DNA)

Sensing
&
Signal amplification

Production of a crRNA

Cas12a

PAM molecular label
(fluorophore, enzyme, AuNP, etc)

dsDNA reporter cleavage strand displacement ssDNA array base pairing

**signal spatially
resolved on array**

DNA array

Guide RNA

Cas protein

Cleavage

Cleavage

Target DNA

ON or OFF

Fig. 14b
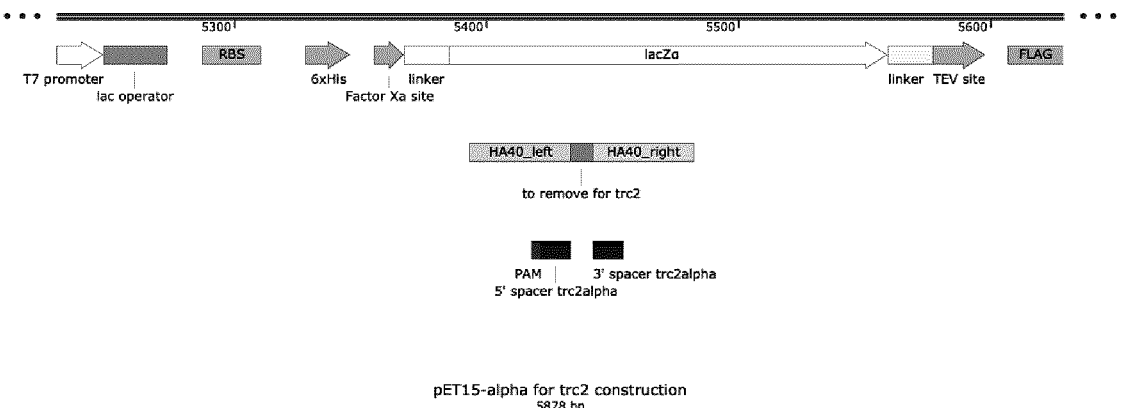
pET15-alpha for trc2 construction
5878 bp
Fig. 14c
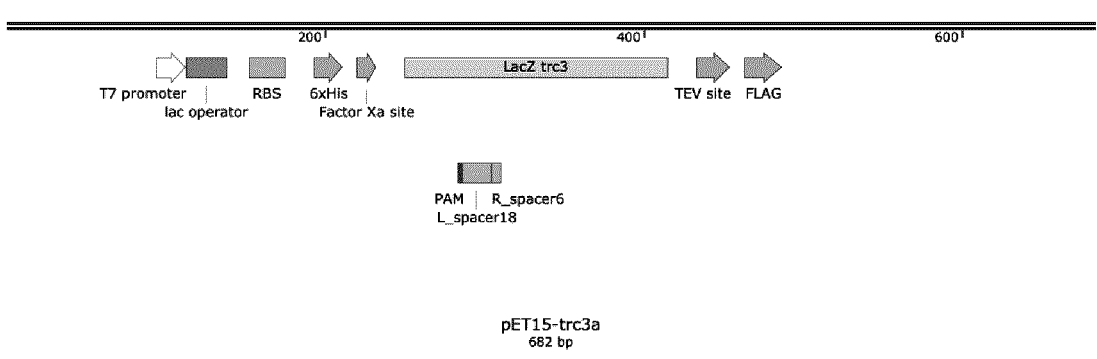
pET15-trc3a
682 bp
Fig. 15a
```
5'   GCGCTAATACGACTCACTATAGGGGTCTAAGAACTTTAAATAATTTCTACTGTTGTAGATATCCCCCTTTCGCCAGCTGGCGTA   3'
     |--+--+--+--+--+--+--+--+--+--+--+--+--+--+--+--+--+--+--+--+--+--+--+--+--+--+--+--+--+--+--+--|
3'   CGCGATTATGCTGAGTGATATCCCCAGATTCTTGAAATTTATTAAAGATGACAACATCTATAGGGGGAAAGCGGTCGACCGCAT   5'
         T7 promoter
```

Fig. 15b

```
5'    GCGCTAATACGACTCACTATAGGGGTCTAAGAACTTTAAATAATTTCTACTGTTGTAGATCAACGTCGTGACCCTGGCGTTACCGTTAAA
      |--+--+--+--+--+--+--+--+--+--+--+--+--+--+--+--+--+--+--+--+--+--+--+--+--+--+--+--+--+--+|
3'    CGCGATTATGCTGAGTGATATCCCCAGATTCTTGAAATTTATTAAAGATGACAACATCTAGTTGCAGCACTGGGACCGCAATGGCAATTT
            [____T7 promoter____>
```

```
      AGTCTAAGAACTTTAAAT        3'
      -+--+--+--+--+--+--|        108
      TCAGATTCTTGAAATTTA        5'
```

Fig. 15c

```
5'    GCGCTAATACGACTCACTATAGGGGTCTAAGAACTTTAAATAATTTCTACTGTTGTAGATCAACGTCGTGACTGGGAAGTTACCGTTAAA
      |--+--+--+--+--+--+--+--+--+--+--+--+--+--+--+--+--+--+--+--+--+--+--+--+--+--+--+--+--+--+|
3'    CGCGATTATGCTGAGTGATATCCCCAGATTCTTGAAATTTATTAAAGATGACAACATCTAGTTGCAGCACTGACCCTTCAATGGCAATTT
            [____T7 promoter____>
```

```
      AGTCTAAGAACTTTAAAT        3'
      -+--+--+--+--+--+--|        108
      TCAGATTCTTGAAATTTA        5'
```

Fig. 15d

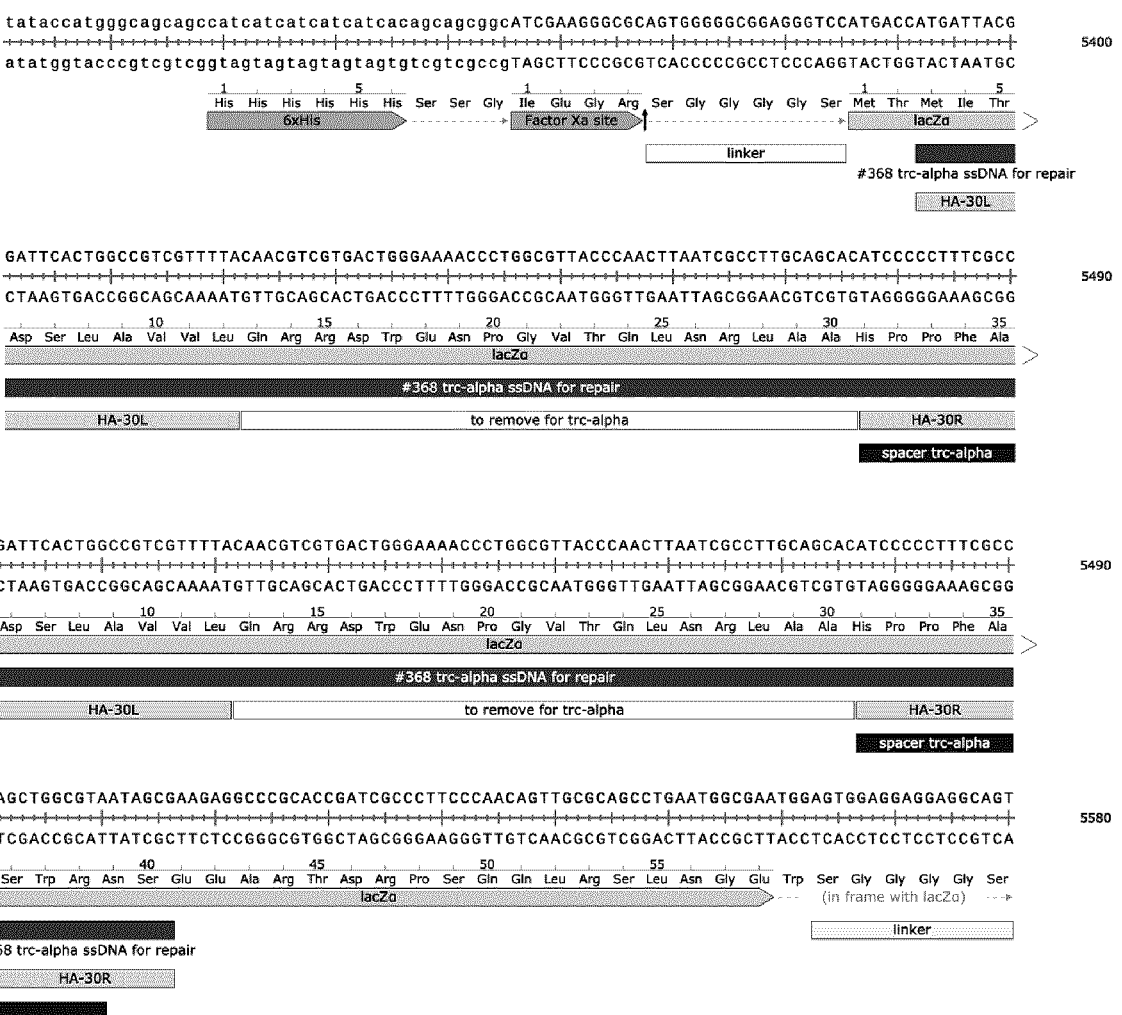

Fig. 16b

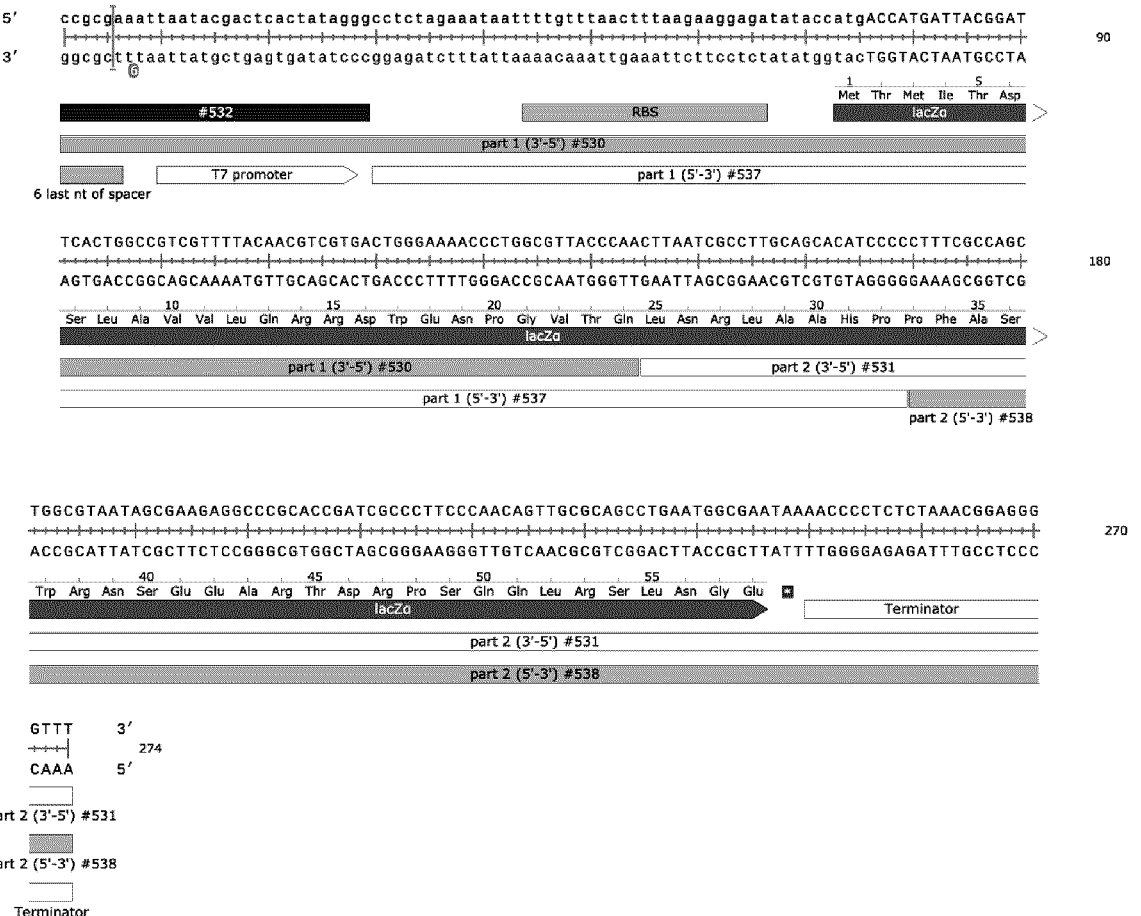

```
5'    ccgcgaaattaatacgactcactatagggcctctagaaataattttgtttaactttaagaaggagatataccatgACCATGATTACGGAT
      |--+--|--+--|--+--|--+--|--+--|--+--|--+--|--+--|--+--|--+--|--+--|--+--|--+--|--+--|--+--|--+--|--+--|--+--|       90
3'    ggcgctttaattatgctgagtgatatcccggagatctttattaaaacaaattgaaattcttcctctatatggtacTGGTACTAATGCCTA
                                                                                   1            5
                                                                                Met Thr Met Ile Thr Asp
```

■■■ #532 ■■■　　　　　RBS　　　　lacZα part 1 (3'-5') #530

6 last nt of spacer　　T7 promoter　　part 1 (5'-3') #537

```
TCACTGGCCGTCGTTTTACAACGTCGTGACTGGGAAAACCCTGGCGTTACCCAACTTAATCGCCTTGCAGCACATCCCCCTTTCGCCAGC
+--+--|--+--|--+--|--+--|--+--|--+--|--+--|--+--|--+--|--+--|--+--|--+--|--+--|--+--|--+--|--+--|--+--|       180
AGTGACCGGCAGCAAAATGTTGCAGCACTGACCCTTTTGGGACCGCAATGGGTTGAATTAGCGGAACGTCGTGTAGGGGGAAAGCGGTCG
        10           15          20          25          30          35
    Ser Leu Ala Val Val Leu Gln Arg Arg Asp Trp Glu Asn Pro Gly Val Thr Gln Leu Asn Arg Leu Ala Ala His Pro Pro Phe Ala Ser
``` lacZα part 1 (3'-5') #530　　　　part 2 (3'-5') #531 part 1 (5'-3') #537 part 2 (5'-3') #538

```
TGGCGTAATAGCGAAGAGGCCCGCACCGATCGCCCTTCCCAACAGTTGCGCAGCCTGAATGGCGAATAAAACCCCTCTCTAAACGGAGGG
+--+--|--+--|--+--|--+--|--+--|--+--|--+--|--+--|--+--|--+--|--+--|--+--|--+--|--+--|--+--|--+--|--+--|       270
ACCGCATTATCGCTTCTCCGGGCGTGGCTAGCGGGAAGGGTTGTCAACGCGTCGGACTTACCGCTTATTTTGGGGAGAGATTTGCCTCCC
        40          45          50          55
    Trp Arg Asn Ser Glu Glu Ala Arg Thr Asp Arg Pro Ser Gln Gln Leu Arg Ser Leu Asn Gly Glu ■
``` lacZα　　　　Terminator part 2 (3'-5') #531 part 2 (5'-3') #538

```
GTTT    3'
+--+--|       274
CAAA    5'
``` part 2 (3'-5') #531 part 2 (5'-3') #538

Terminator

Fig. 16c

```
5'    GCGCTAATACGACTCACTATAGGGGTCTAAGAACTTTAAATAATTTCTACTGTTGTAGATCCAACTCGGCCGATCCGGCCGCGAGTTAAA
      |--+--|--+--|--+--|--+--|--+--|--+--|--+--|--+--|--+--|--+--|--+--|--+--|--+--|--+--|--+--|--+--|--+--|--+--|
3'    CGCGATTATGCTGAGTGATATCCCCAGATTCTTGAAATTTATTAAAGATGACAACATCTAGGTTGAGCCGGCTAGGCCGGCGCTCAATTT
              T7 promoter
```

```
AGTCTAAGAACTTTAAAT    3'
+--+--|--+--|--+--|--+--|       108
TCAGATTCTTGAAATTTA    5'
```

Fig. 16d

```
5'    TGAACAGCCCTGGTCGGCCCTTACCAACTCGGCCGATCCGGCCGCGAAATTAATACGACTCACTATAGGG    3'
      |--+--|--+--|--+--|--+--|--+--|--+--|--+--|--+--|--+--|--+--|--+--|--+--|--+--|
3'    ACTTGTCGGGACCAGCCGGGAATGGTTGAGCCGGCTAGGCCGGCGCTTTAATTATGCTGAGTGATATCCC    5'
                                                              T7 promoter
``` amplification product #470-683
248 bp

Fig. 17d
Fig. 17e
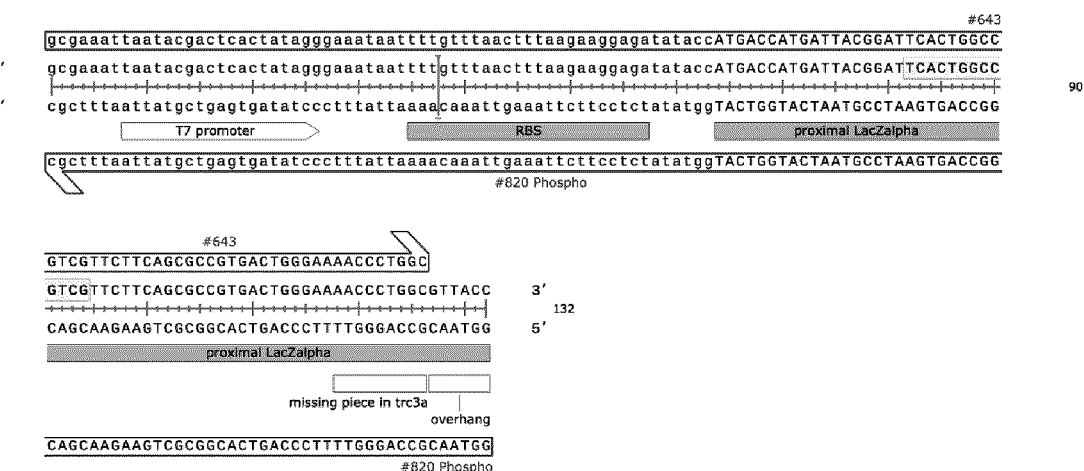
Fig. 17f
```
5'     GCGCTAATACGACTCACTATAGGGGTCTAAGAACTTTAAATAATTTCTACTGTTGTAGATCAACGTCGTGACTGGGAAGTTACCGTTAAA
       |--+--+--+--|--+--+--+--|--+--+--+--|--+--+--+--|--+--+--+--|--+--+--+--|--+--+--+--|--+--+--+--|
3'     CGCGATTATGCTGAGTGATATCCCCAGATTCTTGAAATTTATTAAAGATGACAACATCTAGTTGCAGCACTGACCCTTCAATGGCAATTT
            [   T7 promoter   >
       AGTCTAAGAACTTTAAAT     3'
       +--+--+--|--+--+--+--|     108
       TCAGATTCTTGAAATTTA     5'
```

Diagnostic target: nucleic acid DNA - sensitivity using HDA

Diagnostic target: nucleic acid RNA - sensitivity using RTHDA

Fig. 17m

```
5'   ATTTAAAGTTCTTAGACTTTTAACGGTAACTTCCCAGTCACGACGTTGATCTACAACAGTAGAAATTATTTAAAGTTCTTAGACGGATCA
     ├───┼───┼───┼───┼───┼───┼───┼───┼───┼───┼───┼───┼───┼───┼───┼───┼───┼───┼───┼───┼───┼───┼───┤
3'   TAAATTTCAAGAATCTGAAAATTGCCATTGAAGGGTCAGTGCTGCAACTAGATGTTGTCATCTTTAATAAATTTCAAGAATCTGCCTAGT

TATCCTTGATGGATTCGACATTAT    3'
     ├───┼───┼───┼───┼───┼───┤       114
     ATAGGAACTACCTAAGCTGTAATA    5'
```

Fig. 17n sensitivity dsDNAcrRNA detection using RPA

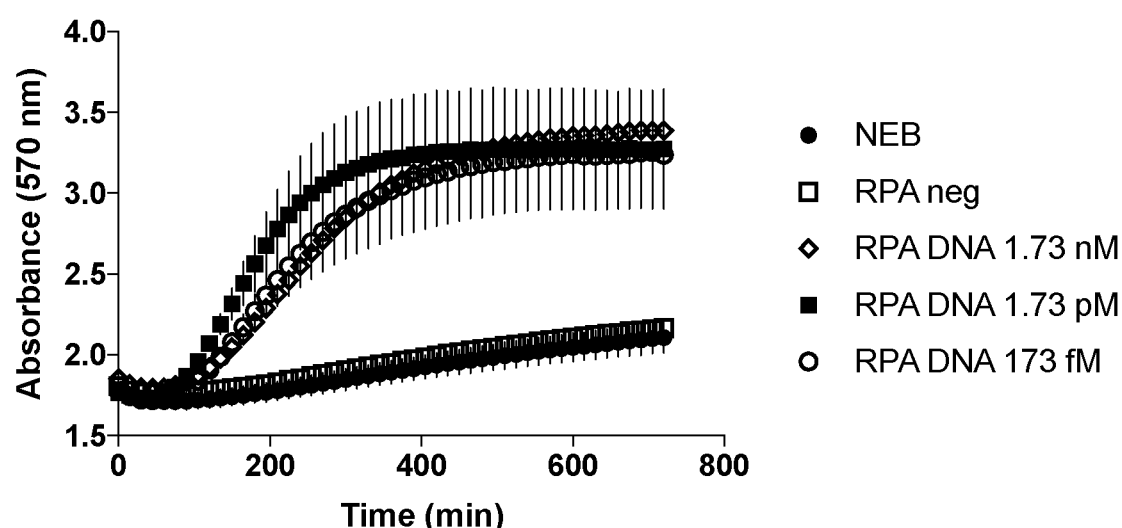

- ● NEB
- □ RPA neg
- ◇ RPA DNA 1.73 nM
- ■ RPA DNA 1.73 pM
- ○ RPA DNA 173 fM

Fig. 17o sensitivity dsDNAcrRNA detection without amplification

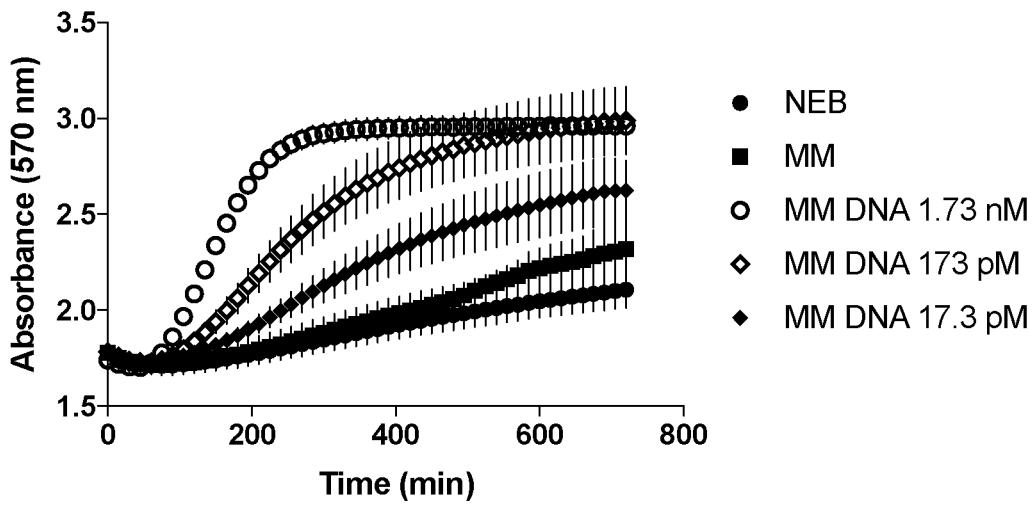

Legend:
- ● NEB
- ■ MM
- ○ MM DNA 1.73 nM
- ◇ MM DNA 173 pM
- ◆ MM DNA 17.3 pM

Fig. 18

```
5'   ATTTAAAGTTCTTAGACTTTTAACGTAAAACGACGGCCAGTGAATCCGATCTACAACAGTAGAAATTATTTAAAGTTCTTAGACGGATCA
     |--+--+--+--+--+--+--+--+--+--+--+--+--+--+--+--+--+--+--+--+--+--+--+--+--+--+--+--+--+--+
3'   TAAATTTCAAGAATCTGAAAATTGCATTTTGCTGCCGGTCACTTAGGCTAGATGTTGTCATCTTTAATAAATTTCAAGAATCTGCCTAGT
```

```
     TATCCTTGATGGATTCGACATTAT      3'
     +--+--+--+--+--+--+--+--|         114
     ATAGGAACTACCTAAGCTGTAATA      5'
```

Fig. 19a

```
5'   CCATGATTACGAAGGCTCCACTGCTTCTGCTTGGGA      3'
     |--+--+--+--+--+--+--+--+--+--+--+--|         36
3'   GGTACTAATGCTTCCGAGGTGACGAAGACGAACCCT      5'
```

Different steps taken

Laser cut QR
code to serve
as mold
For the
inverted QR
code

Inverted QR
code made of
glue – Molded
on the laser
cut piece.

Inverted
QR code
wax
printed

Successful rehydration of the
inverted QR code. The color
mimicking the molecular
reaction enables to read the
QR code.

SEQUENCE LISTING

<160> NUMBER OF SEQ ID NOS: 28

<210> SEQ ID NO 1
<211> LENGTH: 56
<212> TYPE: DNA
<213> ORGANISM: Artificial Sequence
<220> FEATURE:
<223> OTHER INFORMATION: Synthetic Construct

<400> SEQUENCE: 1
gcgctaatac gactcactat agggcgaagt tcatatgctc aacaagggcg ccgagg          56

<210> SEQ ID NO 2
<211> LENGTH: 54
<212> TYPE: DNA
<213> ORGANISM: Artificial Sequence
<220> FEATURE:
<223> OTHER INFORMATION: Synthetic Construct

<400> SEQUENCE: 2
gcgctaatac gactcactat agggcccggc gacacggtca cctttattcc agtg           54

<210> SEQ ID NO 3
<211> LENGTH: 108
<212> TYPE: DNA
<213> ORGANISM: Artificial Sequence
<220> FEATURE:
<223> OTHER INFORMATION: Synthetic Construct

<400> SEQUENCE: 3
gcgctaatac gactcactat aggggtctaa gaactttaaa taatttctac tgttgtagat     60
caacgtcgtg actgggaagt taccgttaaa agtctaagaa ctttaaat               108

<210> SEQ ID NO 4
<211> LENGTH: 84
<212> TYPE: DNA
<213> ORGANISM: Artificial Sequence
<220> FEATURE:
<223> OTHER INFORMATION: Synthetic Construct

<400> SEQUENCE: 4
gcgctaatac gactcactat aggggtctaa gaactttaaa taatttctac tgttgtagat     60
atcccccttt cgccagctgg cgta                                         84

<210> SEQ ID NO 5
<211> LENGTH: 108
<212> TYPE: DNA
<213> ORGANISM: Artificial Sequence
<220> FEATURE:
<223> OTHER INFORMATION: Synthetic Construct

<400> SEQUENCE: 5
gcgctaatac gactcactat aggggtctaa gaactttaaa taatttctac tgttgtagat     60
caacgtcgtg accctggcgt taccgttaaa agtctaagaa ctttaaat               108

<210> SEQ ID NO 6
<211> LENGTH: 359
<212> TYPE: DNA
<213> ORGANISM: Artificial Sequence
<220> FEATURE:
<223> OTHER INFORMATION: Synthetic Construct

<400> SEQUENCE: 6
tataccatgg gcagcagcca tcatcatcat catcacagca gcggcatcga agggcgcagt     60

-continued

```
gggggcggag ggtccatgac catgattacg gattcactgg ccgtcgtttt acaacgtcgt        120
gactgggaaa accctggcgt tacccaactt aatcgccttg cagcacatcc ccctttcgcc        180
gattcactgg ccgtcgtttt caacgtcgtg actgggaaaa ccctggcgtt acccaactta        240
atcgccttgc agcacatccc cctttcgcca gctggcgtaa tagcgaagag gcccgcaccg        300
atcgcccttc ccaacagttg cgcagcctga atggcgaatg gagtggagga ggaggcagt        359
```

```
<210> SEQ ID NO 7
<211> LENGTH: 180
<212> TYPE: DNA
<213> ORGANISM: Artificial Sequence
<220> FEATURE:
<223> OTHER INFORMATION: Synthetic Construct

<400> SEQUENCE: 7
tataccatgg gcagcagcca tcatcatcat catcacagca gcggcatcga agggcgcagt         60
gggggcggag ggtccatgac catgattacg gattcactgg ccgtcgtttt acaacgtcgt        120
gactgggaaa accctggcgt tacccaactt aatcgccttg cagcacatcc ccctttcgcc        180
```

```
<210> SEQ ID NO 8
<211> LENGTH: 180
<212> TYPE: DNA
<213> ORGANISM: Artificial Sequence
<220> FEATURE:
<223> OTHER INFORMATION: Synthetic Construct

<400> SEQUENCE: 8
actggccgtc gttttacaac gtcgtgactg ggaagttacc caacttaatc gccttgcagc         60
acatccccct ttcgccagct ggcgtaatag cgaagaggcc cgcaccgatc gcccttccca        120
acagttgcgc agcctgaatg gcgaaagtgg aggaggaggc agtgaaaact tatacttcca        180
```

```
<210> SEQ ID NO 9
<211> LENGTH: 270
<212> TYPE: DNA
<213> ORGANISM: Artificial Sequence
<220> FEATURE:
<223> OTHER INFORMATION: Synthetic Construct

<400> SEQUENCE: 9
tataccatgg gcagcagcca tcatcatcat catcacagca gcggcatcga agggcgcagt         60
gggggcggag ggtccatgac catgattacg gattcactgg ccgtcgtttt acaacgtcgt        120
gactgggaaa accctggcgt tacccaactt aatcgccttg cagcacatcc ccctttcgcc        180
agctggcgta atagcgaaga ggcccgcacc gatcgccctt cccaacagtt gcgcagcctg        240
aatggcgaaa gtggaggagg aggcagtgaa                                         270
```

```
<210> SEQ ID NO 10
<211> LENGTH: 274
<212> TYPE: DNA
<213> ORGANISM: Artificial Sequence
<220> FEATURE:
<223> OTHER INFORMATION: Synthetic Construct

<400> SEQUENCE: 10
ccgcgaaatt aatacgactc actatagggc tctagaaat aattttgttt aactttaaga          60
aggagatata ccatgaccat gattacggat tcactggccg tcgttttaca acgtcgtgac        120
tgggaaaacc ctggcgttac ccaacttaat cgccttgcag cacatccccc tttcgccagc        180
```

-continued

```
tggcgtaata gcgaagaggc ccgcaccgat cgcccttccc aacagttgcg cagcctgaat      240
ggcgaataaa acccctctct aaacggaggg gttt                                  274

<210> SEQ ID NO 11
<211> LENGTH: 108
<212> TYPE: DNA
<213> ORGANISM: Artificial Sequence
<220> FEATURE:
<223> OTHER INFORMATION: Synthetic Construct

<400> SEQUENCE: 11
gcgctaatac gactcactat aggggtctaa gaactttaaa taatttctac tgttgtagat       60
ccaactcggc cgatccggcc gcgagttaaa agtctaagaa ctttaaat                    108

<210> SEQ ID NO 12
<211> LENGTH: 70
<212> TYPE: DNA
<213> ORGANISM: Artificial Sequence
<220> FEATURE:
<223> OTHER INFORMATION: Synthetic Construct

<400> SEQUENCE: 12
tgaacagccc tggtcggccc ttaccaactc ggccgatccg gccgcgaaat taatacgact       60
cactataggg                                                              70

<210> SEQ ID NO 13
<211> LENGTH: 180
<212> TYPE: DNA
<213> ORGANISM: Artificial Sequence
<220> FEATURE:
<223> OTHER INFORMATION: Synthetic Construct

<400> SEQUENCE: 13
actggccgtc gttttacaac gtcgtgactg ggaagttacc caacttaatc gccttgcagc       60
acatccccct ttcgccagct ggcgtaatag cgaagaggcc cgcaccgatc gcccttccca      120
acagttgcgc agcctgaatg gcgaaagtgg aggaggaggc agtgaaaact tatacttcca      180

<210> SEQ ID NO 14
<211> LENGTH: 248
<212> TYPE: DNA
<213> ORGANISM: Artificial Sequence
<220> FEATURE:
<223> OTHER INFORMATION: Synthetic Construct

<400> SEQUENCE: 14
gcgctaatac gactcactat agggcgaagt tcatatgctc aacaagggcg ccgagggcgc       60
catggttttc gagcctgcct atatcaaggc caatcccggc gacacggtca cctttattcc      120
agtggacaaa ggacataatg tcgaatccat caaggatatg atccgtctaa gaactttaaa      180
taatttctac tgttgtagat caacgtcgtg actgggaagt taccgttaaa agtctaagaa      240
ctttaaat                                                                248

<210> SEQ ID NO 15
<211> LENGTH: 132
<212> TYPE: DNA
<213> ORGANISM: Artificial Sequence
<220> FEATURE:
<223> OTHER INFORMATION: Synthetic Construct.

<400> SEQUENCE: 15
gcgaaattaa tacgactcac tatagggaaa taattttgtt taactttaag aaggagatat       60
```

-continued

```
accatgacca tgattacgga ttcactggcc gtcgttcttc agcgccgtga ctgggaaaac      120
cctggcgtta cc                                                          132

<210> SEQ ID NO 16
<211> LENGTH: 273
<212> TYPE: DNA
<213> ORGANISM: Artificial Sequence
<220> FEATURE:
<223> OTHER INFORMATION: Synthetic Construct

<400> SEQUENCE: 16
tataccatgg gcagcagcca tcatcatcat catcacagca gcggcatcga agggcgcagt       60
tgggggcgga gggtccatga ccatgattac ggattcactg gccgtcgttt tacaacgtgg      120
ggtgactggg aaaaccctgg cgttacccaa cttaatcgcc ttgcagcaca tccccctttc      180
gccagctggc gtaatagcga gaggcccgc accgatcgcc cttcccaaca gttgcgcagc      240
ctgaatggcg aaagtggagg aggaggcagt gaa                                   273

<210> SEQ ID NO 17
<211> LENGTH: 114
<212> TYPE: DNA
<213> ORGANISM: Artificial Sequence
<220> FEATURE:
<223> OTHER INFORMATION: Synthetic Construct

<400> SEQUENCE: 17
atttaaagtt cttagacttt taacggtaac ttcccagtca cgacgttgat ctacaacagt       60
agaaattatt taaagttctt agacggatca tatccttgat ggattcgaca ttat            114

<210> SEQ ID NO 18
<211> LENGTH: 114
<212> TYPE: DNA
<213> ORGANISM: Artificial Sequence
<220> FEATURE:
<223> OTHER INFORMATION: Synthetic Construct

<400> SEQUENCE: 18
atttaaagtt cttagacttt taacgtaaaa cgacggccag tgaatccgat ctacaacagt       60
agaaattatt taaagttctt agacggatca tatccttgat ggattcgaca ttat            114

<210> SEQ ID NO 19
<211> LENGTH: 36
<212> TYPE: DNA
<213> ORGANISM: Artificial Sequence
<220> FEATURE:
<223> OTHER INFORMATION: Synthetic Construct

<400> SEQUENCE: 19
ccatgattac gaaggctcca ctgcttctgc ttggga                                 36

<210> SEQ ID NO 20
<211> LENGTH: 135
<212> TYPE: DNA
<213> ORGANISM: Artificial Sequence
<220> FEATURE:
<223> OTHER INFORMATION: Synthetic Construct

<400> SEQUENCE: 20
gtccatgacc atgattacgg attcactggc cgtcgtttta caacgtcgtg actgggaaaa       60
ccctggcgtt acccaactta atcgccttgc agcacatccc cctttcgcca gctggcgtaa      120
```

-continued tagcgaagag gcccg                                                                     135

<210> SEQ ID NO 21
<211> LENGTH: 115
<212> TYPE: DNA
<213> ORGANISM: Artificial Sequence
<220> FEATURE:
<223> OTHER INFORMATION: Synthetic Construct

<400> SEQUENCE: 21
atgattacgg attcactggc cgtcgtttta caacgtcgtg actgggaaaa ccctggcgtt      60
acccaactta atcgccttgc agcacatccc cctttcgcca gctggcgtaa tagcg           115

<210> SEQ ID NO 22
<211> LENGTH: 89
<212> TYPE: DNA
<213> ORGANISM: Artificial Sequence
<220> FEATURE:
<223> OTHER INFORMATION: Synthetic Construct

<400> SEQUENCE: 22
gattacggat tcactggccg tcgttttaca acgtcgtgac tgggaaaacc ctggcgttac      60
ccaacttaat cgccttgcag cacatcccc                                        89

<210> SEQ ID NO 23
<211> LENGTH: 94
<212> TYPE: DNA
<213> ORGANISM: Artificial Sequence
<220> FEATURE:
<223> OTHER INFORMATION: Synthetic Construct

<400> SEQUENCE: 23
ggattcactg gccgtcgttt tacaacgtcg tgactgggaa aaccctggcg ttacccaact      60
taatcgcctt gcagcacatc cccctttcgc cagc                                  94

<210> SEQ ID NO 24
<211> LENGTH: 54
<212> TYPE: DNA
<213> ORGANISM: Artificial Sequence
<220> FEATURE:
<223> OTHER INFORMATION: Synthetic Construct

<400> SEQUENCE: 24
gcgctaatac gactcactat aggggacgca accccaggaa tccgccaatt caag            54

<210> SEQ ID NO 25
<211> LENGTH: 90
<212> TYPE: DNA
<213> ORGANISM: Artificial Sequence
<220> FEATURE:
<223> OTHER INFORMATION: Synthetic Construct

<400> SEQUENCE: 25
caagcagaag cagtggagcc ttcgatctac aacagtagaa attatttaaa gttcttagac      60
gagcagccac attaagcata ttacacacac                                       90

<210> SEQ ID NO 26
<211> LENGTH: 54
<212> TYPE: DNA
<213> ORGANISM: Artificial Sequence
<220> FEATURE:
<223> OTHER INFORMATION: Synthetic Construct

<400> SEQUENCE: 26

-continued

```
gcgctaatac gactcactat aggggacgca accccaggaa tccgccaatt caag          54

<210> SEQ ID NO 27
<211> LENGTH: 90
<212> TYPE: DNA
<213> ORGANISM: Artificial Sequence
<220> FEATURE:
<223> OTHER INFORMATION: Synthetic Construct

<400> SEQUENCE: 27
ggtaacttcc cagtcacgac gttgatctac aacagtagaa attatttaaa gttcttagac      60
gagcagccac attaagcata ttacacacac                                      90

<210> SEQ ID NO 28
<211> LENGTH: 9
<212> TYPE: DNA
<213> ORGANISM: Escherichia coli

<400> SEQUENCE: 28 aaccctggc                                                               9
```

MOLECULAR SENSING PLATFORM AND METHODS OF USE

RELATED APPLICATIONS

This is a Patent Cooperation Treaty Application which claims priority to United Kingdom patent application GB1914568.9, filed Oct. 9, 2019, herein incorporated by reference in its entirety.

FIELD

The present disclosure relates to a target-nucleic acid-specific generation of a crRNA-encoding nucleic acids, nucleic acid sensors, and in particular to methods and uses thereof for various applications including cell free and cell based applications, such as diagnostic and molecular barcoding applications.

INTRODUCTION

Sensors such as nucleic acid sensors have multiple applications.

Diagnostics

Molecular diagnostics use pathogen genomes, or the sequences of disease (e.g. cancer-related mutations), as a biomarker or molecular barcode for detection. Such molecular technologies compare favorably to traditional antibody-based diagnostics, which are expensive to develop and generally only probe for surface markers on pathogens. Molecular diagnostics, can be developed relatively inexpensively and may probe not only for the presence of disease, but also for other relevant clinical features, such as drug resistance. Molecular technologies also offer an incredible level of signal amplification.

Taken together, these advantages have resulted in molecular-based methods becoming the gold standard for diagnostics. Polymerase Chain Reaction (PCR) is by far the most common mode of detection for molecular diagnostics. It is a powerful technique that allows for the detection of minute amounts of specific nucleic acids through a series of amplification reactions that require thermal cycling. In the clinic, PCR has been embedded into dozens of benchtop diagnostic instruments and is the process that underlies almost all modern diagnostics done in the clinic. These systems, however, have been largely confined to use in laboratory settings because of their costly and bulky hardware, and the requirement for specialized personnel.

Molecular Barcoding

Molecular barcoding, is the use of molecular technologies to detect synthetic or natural DNA sequences from commodities for the purpose of identifying the product or other related information such as manufacturing origin. The concept is analogous to optical barcoding systems, such as Universal Product Code (UPC) or Quick Response Codes (QR codes), but with the advantage that the "barcode" can be embedded throughout the product, making tampering or fraud more difficult. There have been previous commercial efforts using DNA labels, but these have required samples to be sent away for sequencing, making the system impractical for most applications.

De-Centralized Molecular Capabilities

The rising cost of health care and the need for de-centralized technologies for maintaining public health have led to a significant effort toward building low cost and portable diagnostics. While it would be ideal to deploy PCR to point-of-care (POC) settings, cost and technical requirements have largely restricted PCR to the lab. One important area of focus has been the development of isothermal nucleic acid amplification methods. As the name suggests, these amplification reactions operate at a single temperature, rather than thermal cycling, and as such do not require sophisticated equipment. In fact, heating for these reactions can even be provided using a chemical heater (e.g. calcium oxide and water reaction) (Curtis et al., 2012). Other benefits of isothermal methods include a simplified workflow, meaning that work can be done outside of the lab by individuals with little to no training (Yan et al., 2014). Commercial isothermal reactions have recently become available and with these, practical applications of isothermal amplification as diagnostics (Gan et al., 2014; Linnes et al., 2014). Unfortunately, however, these diagnostics suffer from significant rates of false positives because of off-target amplification.

A method that uses sensors downstream of isothermal amplification to provide a second sequence-specific step, can improve detection specificity and performance (Pardee et. al. 2016).

Toehold switch-based RNA sensors have the advantage of adding an extra sequence-specific check point to isothermal amplification. This additional step significantly improves detection specificity. Unfortunately, toehold switches do not appear to be as sensitive as CRISPR-based approaches.

Other de-centralized sensor platforms use Cas12 and Cas13 (SHERLOCK, DETECTR). These efforts have demonstrated quantification down to attomolar concentrations, detection down to zeptomolar concentrations and sensor multiplexing. While exciting, challenges limit the practical implementation of these most recent technologies. For example, these methods rely on the storage and deployment of RNA-based reagents. RNA is unstable, and SHERLOCK requires that pre-packaged RNAs be used to both guide the specificity of the technology (e.g. crRNAs) and create the signal for positive results (e.g. RNA-based reporters). Not only is RNA prone to physical/chemical deterioration, but upon exposure to real world patient and environmental samples one can anticipate significant non-specific activation of the RNA-based reporter by nucleases. From the technical side, these technologies are also limited to cleavage-based mechanisms for the generation of reporter signal.

Thus there is a need for additional molecular technologies for reading molecular barcodes at the point-of-use.

SUMMARY

The inventors have developed a nucleic acid sensing platform that combines CRISPR technology that is free of the need for pre-packaged RNA inputs and can generate reporter signal in various modes (e.g. colorimetric, electrochemical, enzymatic, luminescent or fluorescent) and that is compatible with cell-free or cell-based applications. Cell-free applications include, e.g. diagnostic or barcode applications, and cell-based applications include, for example synchronization of process to endogenous gene expression via crRNA embedded in 3' UTR of gene. Production of the crRNA can be regulated for example depending on the expression profile of the gene in which a crRNA primer is embedded and resulting the guide RNA can be selected to actuate desired downstream effects such as cell suicide.

As shown in the Examples, methods and products involving the real time and multiplexed synthesis of guide RNAs for incorporation into the Cas complex, as well as the development of a downstream nucleic acid restructuringbased reporter are provided. As demonstrated, the systems and components described provide robust and flexible sensing platform.

Provided in some embodiments is a nucleic acid sensor, based on CRISPR technology that can be rationally designed for broad applications in portable diagnostics, in sensing and in biotechnology.

As described herein, some embodiments pertain to systems, products and methods that utilize RNA-based guides (crRNA) for CAS enzymes such as Cas12a (Cpf1) to be generated at the time of use during the amplification process. For example, crRNA can be generated using isothermal amplification methods such as nucleic acid sequence-based amplification (NASBA), or through transcription-based amplification reactions from for example dsDNA encoding a promoter and crRNA supplied to reactions or through ssDNA-based RNA generation. In particular, transcription-based amplification methods may be used with barcoding applications. In amplification-based embodiments, the sensors systems utilize primer directed amplification to reach low detection thresholds which can be necessary for diagnostic applications. As demonstrated herein, in some embodiments DNA corresponding to a desired crRNA sequence is added as an extension on one primer and a promoter is added as an extension on another primer used for the amplification process, thereby generating a DNAcrRNA which encodes the required guide RNA when the target sequence to be detected is present. When the DNAcrRNA is used to generate an RNA amplicon, a Cas enzyme such as Cas12a (Cpf1) is capable of extracting this crRNA from the RNA amplicon, essentially loading itself with the guide RNA, which provides the specificity required for activation of a gene such as a reporter gene or molecular beacon. Native Cas12a is capable of recognizing the crRNA when the spacer sequence is flanked by direct repeats (DR). As shown herein, as the spacer is flanked by one or more direct repeats, Cas12a is able to cleave a crRNA and load it. In some embodiments, using an enzyme like Cas9, the system would be supplemented with tracer RNA and a RNAse III enzyme. By production of the RNA following amplification, the tracer RNA would hybridize to the guideRNA, forming a dsRNA structure that the RNAseIII would cleave, allowing Cas9 to load the guideRNA. Using a Cas9 enzyme, the system could also utilize a primer with extensions corresponding to a single-guideRNA (the tracer RNA is included in the primer with the guideRNA) and a RNAse III enzyme. Allowing for RNA-free deployment of sensor kits can greatly improve the practical utility of the sensor system.

Accordingly, an aspect is a crRNA primer comprising, from 5' to 3', a crRNA-encoding segment that is sequence encoding a crRNA or the reverse complement of a sequence encoding a crRNA, and a distal target segment that has or is complementary to the sequence of a distal portion of the target nucleic acid. As provides is an oligonucleotide insert, for example a dsDNA insert, comprising sequence similar to the primers described herein that can be inserted into a gene that can be induced. The oligonucleotide insert can be an array comprising repeating units of the insert targeting one or more target nucleic acids. The target nucleic acids can for example be one or more essential genes or genes involved in biofuel production as described in the examples below.

Also provided is an oligonucleotide primer, optionally a promoter primer or a crRNA primer.

Another aspect of the disclosure includes an oligonucleotide primer pair comprising: a promoter primer comprising, from 5' to 3', a transcriptional promoter, and a proximal detection target segment that has, or is complementary to, the sequence of a proximal portion of a detection target nucleic acid; and a crRNA primer comprising, from 5' to 3', a crRNA encoding segment that is a sequence encoding a crRNA or the reverse complement of a sequence encoding a crRNA, and a distal detection target segment that has, or is complementary to, the sequence of a distal portion of the detection target nucleic acid, wherein the target segments in each primer permit amplification from the detection target nucleic acid. In one embodiment the crRNA primer is comprised in an array up to 8000 base pairs in length. In one embodiment, the promoter primer comprises a T7 promoter, T3 promoter, or SP6 promoter. In one embodiment the crRNA primer is between 30 and 200 base pairs in length. Similar design could be used when generating guideRNA nucleic acids for use with Cas9 enzyme.

Another aspect includes a system for target nucleic acid-specific generation of a crRNA-encoding nucleic acid, optionally a DNA molecule, the system comprising: at least one primer pair described herein; and a polymerase, such as a DNA polymerase and components for nucleic acid amplification. In one embodiment the DNA polymerase is an isothermal DNA polymerase (e.g. suitable for isothermal amplification), optionally the isothermal DNA polymerase is suitable for use in isothermal amplification method selected from Lamp, NASBA, RPA, NEAR, and/or the polymerase is selected from AMV-RT, Bsu, IsoPol, and HDA. In one embodiment the DNA polymerase is a pCR polymerase such as Q5.

Another aspect includes a method of target-nucleic acid-specific generation of a crRNA-encoding nucleic acid molecule, the method comprising: a) contacting a system for target nucleic acid-specific generation of a crRNA-encoding nucleic acid molecule described herein with a sample containing the target nucleic acid; and b) incubating the system contacted with sample of step a) under conditions for target-specific amplification of the target sequence to generate a crRNA-encoding nucleic acid molecule.

The nucleic acid molecule can be DNA, RNA or a hybrid thereof. For example, the methods and systems described herein can generate RNA as an output of the isothermal amplification (like for NASBA). In other embodiments, the output of amplification can be DNA.

A further aspect includes a method of detecting a target nucleic acid in a sample, the method comprising: a) providing a sample to be tested for the presence of the target nucleic acid; b) contacting the system for target nucleic acid-specific generation of a crRNA-encoding nucleic acid as described herein with the sample; c) incubating the system under conditions to allow target-specific amplification of any target sequence to generate a crRNA-encoding nucleic acid molecule; d) optionally, separating any crRNA-encoding nucleic acid molecules from remaining primers; e) contacting the crRNA-encoding nucleic acid molecule with an RNA polymerase and components for transcription; f) incubating the crRNA-encoding nucleic acid molecule, RNA polymerase and components for transcription under conditions to allow the generation of a crRNA; g) contacting the crRNA with a CRISPR-Cas protein; h) incubating the crRNA and CRISPR-Cas protein under conditions to allow the binding of the crRNA to the CRISPR-Cas protein to generate an active CRISPR-Cas effector protein; i) contacting the active CRISPR-Cas effector protein with a signal-generating CRISPR-sensitive reporter and components for generating of signal from the signal-generating reporter; j) incubating the active CRISPR-Cas effector protein, the signal-generating CRISPR-sensitive reporter, and components under conditions to allow a function restoring repair on the signal-generating reporter; k) incubating the system under conditions to allow the generation of signal from the signal-generating now functional previously CRISPR-sensitive reporter; and l) detecting the presence or absence of signal.

In one embodiment of the method of detecting a target nucleic acid in a sample, the crRNA-encoding nucleic acid molecule is a DNA molecule. In some embodiments the separating of step d) comprises isolating the crRNA-encoding nucleic acid from the system. In some embodiments separating of step d) comprises removing or inactivating the primers.

In one embodiment of the method of detecting a target nucleic acid in a sample, the promoter primer comprises a T7 promoter and the RNA polymerase is T7 polymerase. In one embodiment the promoter primer comprises a T3 promoter and the RNA polymerase is T3 polymerase. In one embodiment the promoter primer comprises a SP6 promoter and the RNA polymerase is SP6 polymerase.

In one embodiment of the method of detecting a target nucleic acid in a sample the CRISPR-Cas protein is Cpf1.

In one embodiment of the method of detecting a target nucleic acid in a sample the crRNA is generated at time of use.

In one embodiment of the method of detecting a target nucleic acid in a sample the sample is a biological sample. In a further embodiment, the biological sample is obtained from a tissue sample, saliva, blood, plasma, sera, stool, urine, semen, sputum, mucous, lymph, synovial fluid, cerebrospinal fluid, ascites, pleural effusion, seroma, pus, skin swab, or mucosal membrane surface. In one embodiment of the method of detecting a target nucleic acid in a sample the sample is an environmental sample. In a further embodiment the environmental sample is or is obtained from a food sample, a beverage sample, a surface, a soil sample, a water sample, exposure to atmospheric air or other gas sample, or a combination thereof.

The sample can also be any sample that comprises a barcode e.g. a function restoring nucleic acid or the CRISPR-sensitive DNA reporter or sensor.

The method of detecting can also be performed on a printed article comprising a component of the Re-RAIR systems described herein, such as a function restoring nucleic acid or the CRISPR-sensitive DNA reporter or sensor. The article comprising a reaction substrate can be rehydrated and contacted with the missing component. If the missing component of the function restoring nucleic acid restores the function of the DNA sensor a signal is produced.

In one embodiment of the method of detecting a target nucleic acid in a sample the target nucleic acid is unpurified or unamplified from the sample prior to the application of the method.

Another aspect of the disclosure includes a kit for detecting a target nucleic acid in a sample, the kit comprising: at least one primer pair as described herein and packaging materials therefor; or a system for target nucleic acid-specific generation of a crRNA-encoding nucleic acid and packaging materials therefor.

In one embodiment the kit further comprises components to isolate a crRNA. In one embodiment the kit further comprises components to remove or inactivate oligonucleotide primers.

In one embodiment the kit further comprises an RNA polymerase and components for transcription.

In one embodiment the kit further comprises a CRISPR-Cas protein or a nucleic acid encoding a CRISPR-Cas protein and components for generating a CRISPR-Cas protein.

In one embodiment, the kit further comprises a signal-generating CRISPR-sensitive reporter and components to generate signal from the signal-generating CRISPR-sensitive reporter. In a further embodiment the CRISPR-sensitive reporter is a CRISPR-sensitive DNA sensor described herein.

In some, embodiments the primers are removed.

The time of use generation of crRNA can also be exploited as a molecular barcode. crRNA can be generated at time of use from dsDNA oligonucleotides comprising a promoter and crRNA-encoding nucleic acid sequence. As described in the Examples, it was found that the crRNA primer (ssDNA) described herein can be used directly and/or for the generation of crRNA. The molecular barcode embodiments, can operate with the addition of (i) dsDNA comprising a promoter and guide sequence for onsite production of crRNA, (ii) ssDNA to produce crRNA, or (iii) ssDNA as crDNA without production of RNA. In all these cases, the need for using or shipping RNA in test kits is circumvented.

Accordingly, one aspect of the disclosure is a crRNA-encoding nucleic acid, optionally a crRNA-encoding single stranded DNA (ssDNA) molecule comprising a sequence that is the reverse complement of a crRNA molecule. Another aspect of the disclosure is a method of generating a crRNA molecule comprising introducing the nucleic acid, optionally the ssDNA, into a cell free system comprising components for transcription or into a cell, under suitable conditions for transcription and incubating the system or cell under said conditions to make the CRISPR RNA molecule.

Another aspect of the disclosure is a molecular barcode comprising a crRNA-encoding nucleic acid molecule, optionally DNA molecule, optionally for use in labeling a physical good or material, a location, or an event. It can also be a signal inducing CRISPR-sensitive reporter or component thereof e.g. function restoring nucleic acid or a signal generating CRISPR reporter.

In one embodiment the crRNA-encoding nucleic acid molecule is a ssDNA molecule. In a further embodiment, the ssDNA is from 30 to 200 bp in length, optionally in an array of up to 8 kb.

In another embodiment the crRNA-encoding nucleic acid molecule is a dsDNA molecule and the dsDNA molecule further comprises a transcriptional promoter, wherein the promoter is operably linked to the crRNA-encoding DNA. In one embodiment the promoter is a non-canonical promoter. In another embodiment the promoter is a T7 promoter, a T3 promoter, or a SP6 promoter.

In one embodiment the crRNA-encoding nucleic acid, optionally DNA, molecule, is ligase-resistant, optionally the crRNA-encoding nucleic acid, optionally DNA, molecule is modified at its 5'-OH end.

In one embodiment the physical good or material is a consumer product or consumer product packaging. In a further embodiment, the consumer product is selected from *cannabis*, a pharmaceutical drug, a food, a beverage, a fuel, a lubricant, a cosmetic, a perfume, and a gemstone. In another embodiment the physical good or material is selected from an explosive, a biological material, a hazardous chemical, hazardous waste, and currency.

Another aspect of the disclosure includes a method for labeling a physical good or material, a location, or an event comprising adding at least one molecular barcode described herein to a physical good or material, a location, or an event, wherein the molecular barcode is a CRISPR-encoding nucleic acid molecule such as for example a crRNA-encoding nucleic acid or a signal-inducing CRISPR-sensitive reporter, and the adding comprises for example applying, embedding, or dispersing.

In one embodiment the at least one molecular barcode is applied to or printed on the surface of the physical good or material. In a further embodiment, the at least one molecular barcode is applied to or printed on the surface of the physical good or material in a QR-code printed pattern. In another embodiment the at least one molecular barcode is embedded in the physical good or material.

In one embodiment the at least one molecular barcode comprises a signal-inducing CRISPR-sensitive DNA sensor described herein, or a component thereof. In one embodiment, the signal-inducing CRISPR-sensitive sensor or component is a non-functional CRISPR-sensitive DNA reporter or a function restoring repair nucleic acid described herein. In a further embodiment the non-functional CRISPR-sensitive DNA reporter is a dsDNA molecule.

In one embodiment the at least one molecular barcode comprises a DNAcrRNA described herein.

Another aspect of the disclosure includes cell-free system for generating a crRNA, the system comprising: a crRNA-encoding ssDNA; and an RNA polymerase and components for transcription.

Another aspect of the disclosure includes a cell-free system for detecting a molecular barcode described herein, the system comprising: an RNA polymerase and components for transcription; a CRISPR-Cas protein or a nucleic acid encoding a CRISPR-Cas protein and components for generating a CRISPR-Cas protein; a signal-generating CRISPR-sensitive reporter; and components for generating signal from, the signal-generating CRISPR-sensitive reporter.

In one embodiment the RNA polymerase is T7 polymerase, T3 polymerase, or SP6 polymerase.

In one embodiment the CRISPR-Cas protein is Cas12a.

In one embodiment the signal-generating CRISPR-sensitive reporter is a signal-generating CRISPR-sensitive sensor described herein.

Another aspect includes a method of detecting a molecular barcode described herein, the method comprising: a) providing a sample to be tested for the presence of the molecular barcode; b) contacting the sample with a system for detecting a molecular barcode described herein; c) incubating the sample under conditions to allow transcription of a crRNA from the molecular barcode; d) incubating the sample under conditions to allow binding of the crRNA to the CRISPR-Cas protein to generate an active CRISPR-Cas effector protein; e) optionally incubating the sample under conditions to allow a function restoring repair of a signal-generating CRISPR-sensitive sensor described herein; f) incubating the sample under conditions for generating signal from the signal-generating CRISPR-sensitive reporter, optionally to express an RNA, and optionally a protein, from the signal-generating CRISPR-sensitive reporter; f) and detecting the presence or absence of signal.

In one embodiment, the sample is or is obtained from a product label or product packaging. In another embodiment, the sample is an environmental sample. In a further embodiment, the environmental sample is or is obtained from a food sample, a beverage sample, a surface, a soil sample, a water sample, exposure to atmospheric air or other gas sample, or a combination thereof.

Another aspect includes a kit for detecting a molecular barcode described herein, the kit comprising a cell-free system for detecting a molecular barcode described herein and packaging materials therefor. For molecular barcode applications, kits would be supplied without one or more than one DNA encoded components (X, see table A, below, showing possible kit combinations). The molecular barcode can for example be any of the "X" pieces not included in the kit. In some embodiments, this "missing piece(s)" would be included on the product of interest and would serve as the "key" to authenticate the product.

The kit can also comprise a positive control such as the molecular barcode e.g. the missing piece to confirm the assay is working in the hands of the user.

Each kit can also contain other components such as one or more of RNA pol, Cas, NTPs, a buffer, etc or other component described herein.

In an embodiment, the kit further comprises a physical substrate, wherein the system is applied to the physical substrate. In one embodiment the physical substrate is porous substrate. In one embodiment the physical substrate is a flexible materials substrate. In a further embodiment, the substrate is a paper substrate, a fabric substrate, or a flexible polymer-based substrate. In another embodiment the physical substrate is a microtube or chamber.

In an embodiment the cell-free system is applied to the physical substrate in a molecular QR-code printed pattern.

In an embodiment the system is applied to multiple discrete locations on the physical substrate.

In an embodiment the kit further comprises one or more additional discrete reporter systems for detecting a crRNA in a sample, wherein the one or more additional discrete reporter systems is applied to one or more discrete locations on the physical substrate.

The "primer" sequences can also be inserted in a gene to provide a latent activation system for effecting a desired effect when a precipitating or permissive condition is present as described for example in Examples 7 to 9. Accordingly also provided in another aspect is an oligonucleotide insert having sequence similar to a "primer" described herein that can be inserted into a gene such as the 3'UTR of a gene, which under permissive conditions can be used to effect a change, for example such permissive conditions can be when expression of the gene is activated by an internal or external signal. For example the oligonucleotide insert can comprise a crDNA molecule or a crRNA-encoding nucleic acid molecule. The oligonucleotide insert can be comprised in a construct for example for preparing a recombinant cell or subject comprising the oligonucleotide insert.

For example, the construct can comprise a vector backbone and the oligonucleotide insert, and the vector backbone can for example be a viral vector such as a retroviral vector, a plasmid, a bacteriophage or the like.

Also provided herein in one aspect is a cell comprising the oligonucleotide insert, for example inserted in a gene such as the 3'UTR of a gene. The cell can be a bacteria cell, a yeast cell, an insect cell or a mammalian cell. In some embodiments the cell is in a subject such as a rodent, non-human subject or human.

Also provided in another aspect is a kit comprising any component or combination thereof described herein.

For example one embodiment of the disclosure includes a kit for detecting a molecular barcode described herein comprising the cell-free system for detecting a molecular barcode described herein.

Described herein in a further aspect is a reporter system that is based on DNA re-organization, which resolves the limitation of the RNA cleavage-based reporters of SHER-LOCK and DETECTR. As shown in the Examples, CRISPR (Cas12a/Cpf1) guided by specific crRNA (generated as above) or ssDNA to cleave a non-functional reporter gene. In this embodiment, the 5' non-functional end of the reporter is then replaced by a functional 5' end of the reporter gene (and is referred to as Re-PAIRed). By converting the action of CRISPR cleavage into the repair of a reporter cassette, various modes of reporter signal (color, electrochemical, luminescent, fluorescent, etc) can be generated.

This DNA re-organization-based reporter system circumvents the need for costly chemically-modified RNAs and enables multiplexing. For example, the recognition of: sequence A could generate a red reporter signal, sequence B a blue reporter signal, sequence C a green reporter signal, etc.

Accordingly, a further aspect of the disclosure is signal-inducing CRISPR-sensitive DNA sensor, the sensor comprising: I) a non-functional CRISPR-sensitive DNA reporter construct comprising a non-functional expression cassette with at least one CRISPR target site present in the expression cassette, the non-functional expression cassette having a reporter construct upstream-end upstream of the CRISPR target site and a reporter construct downstream-end downstream of the CRISPR target site, and a function-restoring nucleic acid, the function-restoring nucleic acid comprising an upstream flanking end, a function restoring repair insert and optionally a downstream flanking end, wherein the upstream flanking end interfaces with reporter construct upstream end and/or the downstream flanking end interfaces with the reporter construct down-stream end and one or both of the flanking ends permit insertion or ligation of the function restoring repair insert into the reporter construct when the CRISPR target site is actuated under sensing condition, thereby producing a functional DNA reporter construct and sensor signal; or II) a non-functional DNA reporter construct comprising a non-functional expression cassette, the non-functional expression cassette having a single stranded part; and at least one function-restoring nucleic acid (e.g. supplemented dsDNA), the function-restoring nucleic acid comprising a CRISPR target site inserted or naturally present in the function restoring nucleic acid, and a function restoring repair insert complementary to the single stranded part of the non-functional DNA reporter construct, the function restoring insert being releasable upon CRISPR mediated cleavage of the function restoring nucleic acid; wherein the function restoring repair insert interfaces (hybridizes) with the reporter construct single stranded part permitting insertion or ligation of the function restoring repair insert into/to the reporter construct when the CRISPR target site is actuated under sensing condition, thereby producing a functional DNA reporter construct and sensor signal.

In one embodiment, the function-restoring nucleic acid is a ssDNA. In a further embodiment, the upstream flanking end hybridizes or ligates with the reporter construct upstream end and/or the downstream flanking end hybridizes or ligates with the reporter construct downstream end.

In another embodiment the function-restoring nucleic acid is a dsDNA.

Another aspect is a signal-inducing CRISPR-sensitive DNA sensor comprising a non-functional CRISPR-sensitive DNA reporter construct, the reporter construct comprising: a promoter; a reporter cassette; a function-blocking region; CRISPR-Cas target sites that flank the function-blocking region; a reporter construct upstream end upstream of the function-blocking region and a reporter construct down-stream end downstream of the function-blocking region, wherein the upstream end is capable of interfacing with the downstream end to permit function-restoring repair of the reporter construct when the CRISPR target sites are actuated under sensing condition, thereby producing a functional DNA reporter construct and sensor signal.

Another aspect is a cell-free system for detecting a CRISPR-RNA (crRNA), the system comprising: the signal-inducing CRISPR-sensitive DNA sensor described herein; a CRISPR-Cas protein, or a nucleic acid encoding a CRISPR-Cas protein and components sufficient for generating a CRISPR-Cas protein; and components for repairing the signal-inducing DNA sensor.

In one embodiment, the signal-inducing CRISPR-sensitive DNA sensor comprises a function-restoring nucleic acid that is a ssDNA, and the components for repairing the sensor comprise an exonuclease, a ligase, and a DNA polymerase. In one embodiment, the signal-inducing CRISPR-sensitive DNA sensor comprises a function-restoring nucleic acid that is a ssDNA, and the components for repairing the sensor comprise a DNA polymerase, optionally the system further comprises a component listed in Table 2.

In one embodiment, the signal-inducing CRISPR-sensitive DNA sensor comprises a function-restoring nucleic acid that is a ssDNA, wherein the upstream flanking end hybridizes or ligates with the reporter construct upstream end and/or the downstream flanking end hybridizes or ligates with the reporter construct downstream end, and the components for repairing the sensor comprise a DNA ligase.

In one embodiment, the signal-inducing CRISPR-sensitive DNA sensor comprises a function-restoring nucleic acid that is a ssDNA, wherein the upstream flanking end hybridizes or ligates with the reporter construct upstream end and/or the downstream flanking end hybridizes or ligates with the reporter construct downstream end, and the CRISPR-Cas protein is Cpf1.

In one embodiment under sensing conditions the signal-inducing CRISPR-sensitive DNA sensor encodes a ribozyme or aptamer and the system further comprises components for transcription.

In one embodiment under sensing conditions the signal-inducing CRISPR-sensitive DNA sensor encodes a protein and the system further comprises components for transcription and translation. In a further embodiment the protein is selected from a fluorescent protein, a luminescent protein, a chromoprotein, an electrochemically active protein, an affinity protein and an enzyme. In a further embodiment the protein is an enzyme, optionally beta galactosidase. In another embodiment the protein is a fluorescent protein or a luminescent protein, optionally the fluorescent protein is green fluorescent protein (GFP).

In one embodiment the repair nucleic acid comprises a modified PAM.

Another aspect is a method of detecting a crRNA in a sample, the method comprising: a) exposing the system for detecting a CRISPR-RNA described herein to the sample; b) incubating the system under conditions to allow binding of any crRNA to the CRISPR-Cas protein to generate an active CRISPR-Cas effector protein; c) incubating the system under conditions to allow modification and repair of the signal-inducing CRISPR-sensitive sensor; d) incubating the system under conditions to allow expression of the reporter cassette; and e) detecting the presence or absence of signal.

In one embodiment, under sensing conditions the signal-inducing CRISPR-sensitive DNA sensor encodes beta galactosidase and the signal being detected is a colorimetric signal or an electrochemical signal.

In one embodiment, under sensing conditions the signal-inducing CRISPR-sensitive DNA sensor encodes a fluorescent protein or a luminescent protein and the signal being detected is a fluorescent signal or a luminescent signal.

Another aspect is a kit for detecting a crRNA in a sample, the kit comprising the signal-inducing CRISPR-sensitive DNA sensor described herein, or a component thereof, and packaging materials therefor; or the system for detecting a CRISPR-RNA described herein and packaging materials therefor.

In one embodiment the kit for detecting a crRNA in a sample further comprises a physical substrate, wherein the sensor system or a component thereof is applied to the physical substrate. In an embodiment the physical substrate is a porous substrate or a flexible materials substrate, optionally a paper substrate, a fabric substrate, or a flexible polymer-based substrate. In an embodiment, the physical substrate is a rigid chip or an electrode, optionally a DNA array, the DNA array comprising for example the sensor or a component thereof such as the function restoring nucleic acid. In one embodiment, the physical substrate is a microtube or chamber.

In one embodiment the system or a component thereof is applied to the physical substrate in a molecular QR-code printed pattern. In a further embodiment the system or a component thereof is applied to multiple discrete locations on the physical substrate.

In one embodiment, the kit for detecting a crRNA in a sample further comprises one or more additional discrete reporter systems or components thereof for detecting a crRNA in a sample, wherein the one or more additional discrete reporter systems or components thereof is applied to one or more discrete locations on the physical substrate.

In one embodiment, the system or a component thereof or the one or more discrete reporter systems or components thereof is/are applied in a predetermined pattern, optionally wherein different patterns are each associated with a known identifier.

Another aspect is a function-restoring nucleic acid, the function-restoring nucleic acid comprising a downstream flanking end, a function restoring repair insert and optionally an upstream flanking end, wherein the upstream flanking end is capable of interfacing with a reporter construct upstream end and/or the downstream flanking end is capable of interfacing with a reporter construct downstream end and one or both of the flanking ends permit insertion or ligation of the function restoring repair insert into/to the reporter construct or other function restoring nucleic acid described herein. A further aspect is a physical substrate comprising the function restoring nucleic acid described herein.

Another aspect is a crRNA-encoding single stranded DNA (ssDNA) molecule comprising a sequence that encodes a crRNA molecule or a sequence that is the reverse complement of a crRNA molecule, optionally as described herein.

In one embodiment, the crRNA-encoding single stranded DNA (ssDNA) molecule further comprises at its 3' end a detection target segment that has the sequence of or is complementary to the sequence of a detection target nucleic acid.

Another aspect is a method of generating a crRNA molecule and/or an assay comprising generating a cRNA molecule, comprising a) introducing the crRNA-encoding ssDNA described herein into i) a cell free system comprising components for transcription or ii) into a cell, under suitable conditions for transcription and b) incubating the system or cell under said conditions to make the crRNA molecule.

A further aspect is a method of generating a crRNA molecule in vivo, comprising introducing an oligonucleotide insert, crRNA or array of crRNAs or inserts in a 3'UTR of a gene into a cell, a tissue, or an organism, wherein the crRNA has the sequence of a protospacer localized on a target gene and inducing 1) a mutation in a coding sequence of a target nucleic acid or 2) repair and function of the cleaved target nucleic acid if a repair DNA (ssDNA or dsDNA) is provided to the cell, wherein the crRNA in the 3'UTR is extractable form mRNA transcribed from the gene.

The preceding section is provided by way of example only and is not intended to be limiting on the scope of the present disclosure and appended claims. Additional objects and advantages associated with the compositions and methods of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional advantages objects and embodiments are expressly included within the scope of the present disclosure.

Other features and advantages of the present application will become apparent from the following detailed description. It should be understood, however, that the detailed description and the specific examples while indicating embodiments described herein are given by way of illustration only, the scope of the claims should not be limited by the embodiments set forth in the examples, but should be given the broadest interpretation consistent with the description as a whole.

DRAWINGS

Further objects, features and advantages of the disclosure will become apparent from the following detailed description taken in conjunction with the accompanying figures showing illustrative embodiments of the disclosure, in which:

FIG. 1 is a schematic showing a particular embodiment of the methods described. For molecular barcoding, labels can be provided as 1 (arrow) or 2 (arrow). In the case of 1, the label is a ssDNA molecule that can be processed as a crRNA or a crDNA and the crRNA or crDNA is loaded into Cas protein and participate to the DNA re-organization. In the case of 2, the label is the DNA encoding the crRNA. RNA is produced in this embodiment using T7 RNA polymerase. Generated crRNA can then be loaded into Cas protein and induce DNA reorganization. Further, labels may also include dsDNA encoding a non-functional reporter or dsDNA encoding the repair element for the non-functional reporter. For diagnostic applications (arrow 3), upon the presence of a specific nucleic acid (diagnostic target), the amplification generates a composite DNA sequence. Both primers used for the amplification recognize in a sequence specific manner the diagnostic target. On one primer, is appended a T7 promotor sequence (for RNA synthesis—in black), on the second one, the sequence coding for the crRNA (dashed). The amplification generates a nucleic acid molecule, comprising a composite DNA containing the sequence allowing downstream RNA synthesis, the trigger sequence recognized by the primers and the DNA encoding the crRNA (black, white and dashed rectangle). Upon addition of a T7 RNA polymerase, the specific composite RNA is synthesized and further processed by Cas protein to generate a specific crRNA dependent of the diagnostic target was generated, allowing downstream CRISPR events.

Final step for the three pathways is DNA re-organization. On the left is represented the "cleavage only" mechanism. Upon production of the crRNA, Cas12 (i.e. Cas12a/Cpf1, alternatively referred to as Cas12a, Cpf1 or Cas12/Cpf1) binds in a sequence specific manner to a functional DNA and will induce cleavage. As the DNA is now broken, no signal can be detected. On the right is the cleavage and DNA re-organization mechanism. Upon production of the crRNA, Cas12a binds to a non-functional DNA and induces a sequence specific cleavage. By providing to the system the missing piece of DNA (dotted rectangle), DNA is repaired and able to generate a detectable signal.

Simple cleavage can also be used to generate signal as shown in FIG. 9*a* and FIG. 9*b*. This could be as simple as signal induced from the cleavage of a molecular beacon (cleavage separates fluorophore from quencher, yielding signal) as shown in FIG. 9*a* or cleavage of an alternate double stranded nucleic acid-based reporter (as shown in FIG. 9*b*). In this latter case, cleavage results in the release of a single-stranded nucleic acid that can now base pair with a third element, for example a DNA array, allowing spatial resolution of multiplexing.

FIG. 2 is a schematic demonstrating nucleic acid dependent crRNA synthesis. Upon the presence of a specific nucleic acid (diagnostic target), the amplification generated a composite DNA sequence. Both primers used for the amplification recognize in a sequence specific manner the diagnostic target. On one primer, is appended a T7 promotor sequence (for RNA synthesis—in black), on the second one, the sequence coding for the crRNA (dashed). The amplification generates a new DNA containing the sequence allowing downstream RNA synthesis, the trigger sequence recognized by the primers and the DNA encoding the crRNA (black, white and dashed). Upon addition of a T7 RNA polymerase, a specific crRNA dependent of the diagnostic target is generated, allowing downstream CRISPR events.

The RNA polymerase, for example Sp6 or T7, can for example be purchased from NEB or Thermo Fisher Scientific.

The RNA polymerase can for example be DNA-dependent RNA polymerase with strict specificity for double-stranded promoters, catalyzing the 5'→3' synthesis of RNA on either single-stranded DNA or double-stranded DNA downstream from its promoter.

FIG. 3 is a schematic of two reporter systems. On the left is represented the "cleavage only" mechanism. Upon production of the crRNA, a Cas protein such as Cas12a binds in a sequence specific manner to a functional DNA and induces cleavage. Any Cas protein with dsDNA break ability would be compatible. As the DNA is now broken, no signal can be detected (as above, through alternate schemes see FIGS. 9*a* and 9*b*, cleavage-only can also lead to observable signals). On the right is the cleavage and DNA reorganization mechanism. Upon production of the crRNA, the Cas protein such as Cas12a binds to a non-functional DNA and induce a sequence specific cleavage. By providing to the system the missing piece of DNA (dotted rectangle), DNA is repaired and able to generate a detectable signal.

FIG. 4 is a drawing of a plate showing the color signal produced using a cleavage only mechanism reporter—signal OFF system. Here the functional gene encode for the enzyme beta-galactosidase. When in presence of the enzyme, substrate CPRG (yellow, represented as light grey) is cleaved and generate a purple color represented as dark grey. In the signal OFF mechanism, without the presence of the diagnostic target, no crRNA was produced and Cas12a was not be able to cleave the DNA of b-galactosidase. The enzyme was produced, cleaved CPRG and generated the purple color as shown (upper wells—dark grey). In presence of the diagnostic target, DNA coding for beta-galactosidase was cleaved, and no purple color is generated as shown (lower wells—light grey).

FIG. 5 is a drawing of a plate showing the color signal produced using a cleavage and DNA re-organization mechanism—signal ON system. DNA coding for non-functional beta-galactosidase is used as a reporter. In the signal ON system, if there is no detection of the diagnostic target, the reporter DNA stays non-functional (no cleavage), no enzyme coding for b-galactosidase is produced (no repair) and therefore the substrate would stay yellow on the paper discs as shown (upper wells—light grey). On the contrary, upon detection of the diagnostic target, the crRNA generated will mediate with Cas12a the non-functional DNA reporter cleavage. The complementary piece of DNA is incorporated in the cleaved reporter DNA. A functional beta-galactosidase enzyme is therefore produced and the substrate is cleaved, generating the purple color on the paper discs as shown (lower wells—dark grey).

FIG. 6 is a schematic of two different promoter primers comprising a T7 promoter and a proximal detection target segment that is complementary to a proximal portion of binding target such as small pAz. Small pAz is a subcloning of a short section of the gene coding for pseudoazurin into a pDEST14 backbone.

FIG. 7 is a schematic of a crRNA primer (ssDNA) comprising a crRNA-encoding segment that includes a spacer complementary to a distal portion of small pAz used to generate that data shown in FIG. 17*l*, as described in Example 3.

Figure 9A:
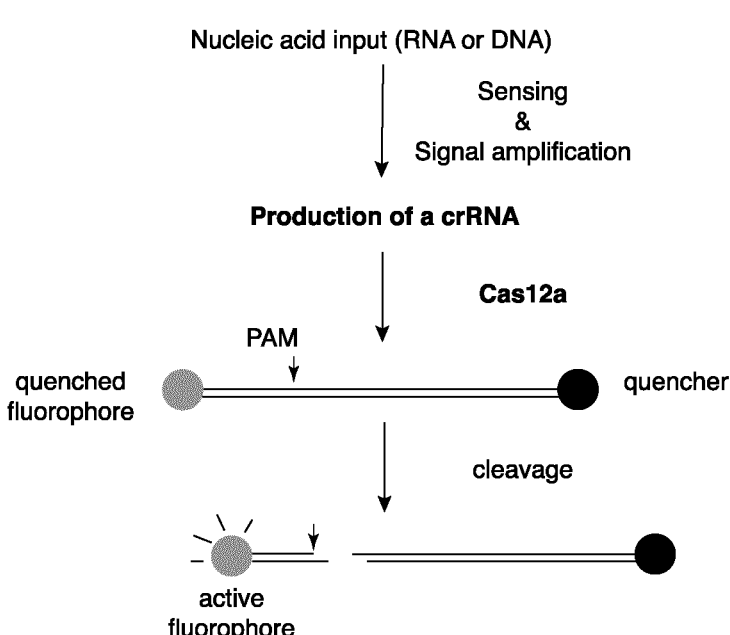
Figures 9B, 10:
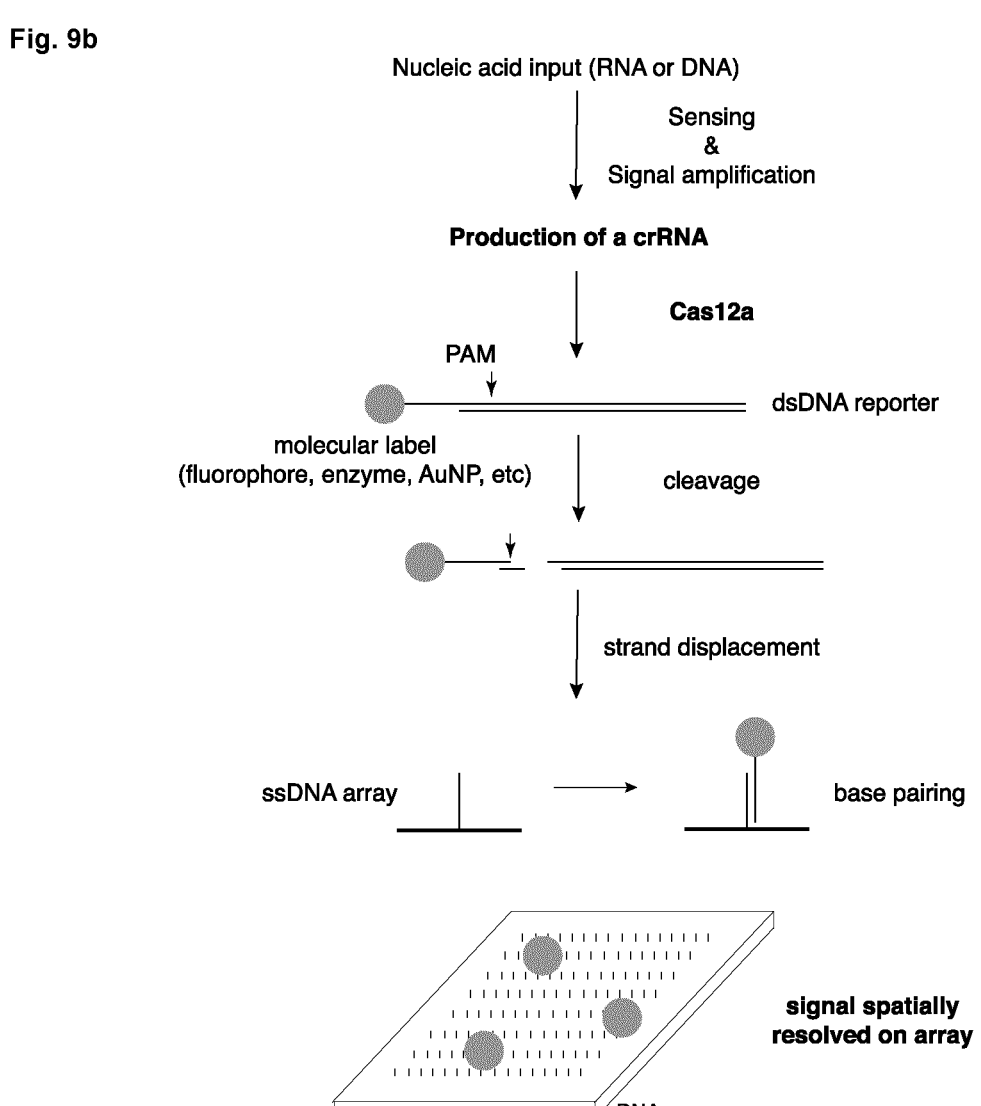

FIG. 9*a* is a schematic of cleavage-based signaling and FIG. 9*b* is a schematic of another cleavage-based signaling that also provides for signal spatially localized on an array, as described in Example 1. FIG. 9*a* describes a cleavage-based signal generating mechanism. Cas12a is loaded with RNA or ssDNA (via either option 1, 2 or 3 in FIG. 1), enabling cleavage of the dsDNA reporter.

FIG. 10 is a schematic of spatially resolved reporter format. Under this format, reporter signal from activation can be spatially localized to enable an additional layer of multiplexing. This format can be used to increase the complexity of DNA-barcoding systems (e.g. each spot is an additional point of confirmation) or to increase the capacity of diagnostics (e.g. each spot is a different disease).

Figure 11:
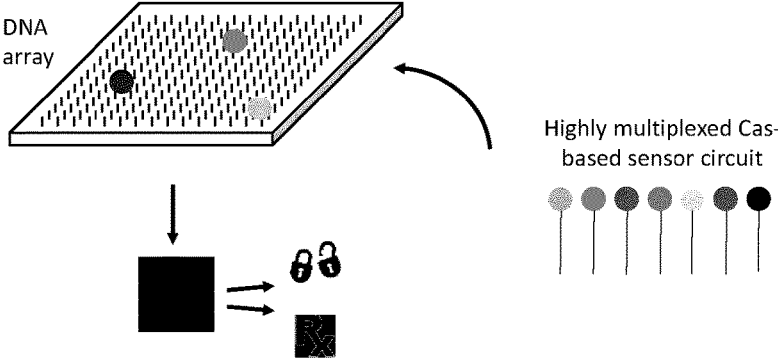

FIG. 11 is a schematic of high capacity circuit-electronic interface. This interface allows for increase multiplexing for diagnostics or barcoding, and provides for single deployable chip for comprehensive sensing.

Figure 12:
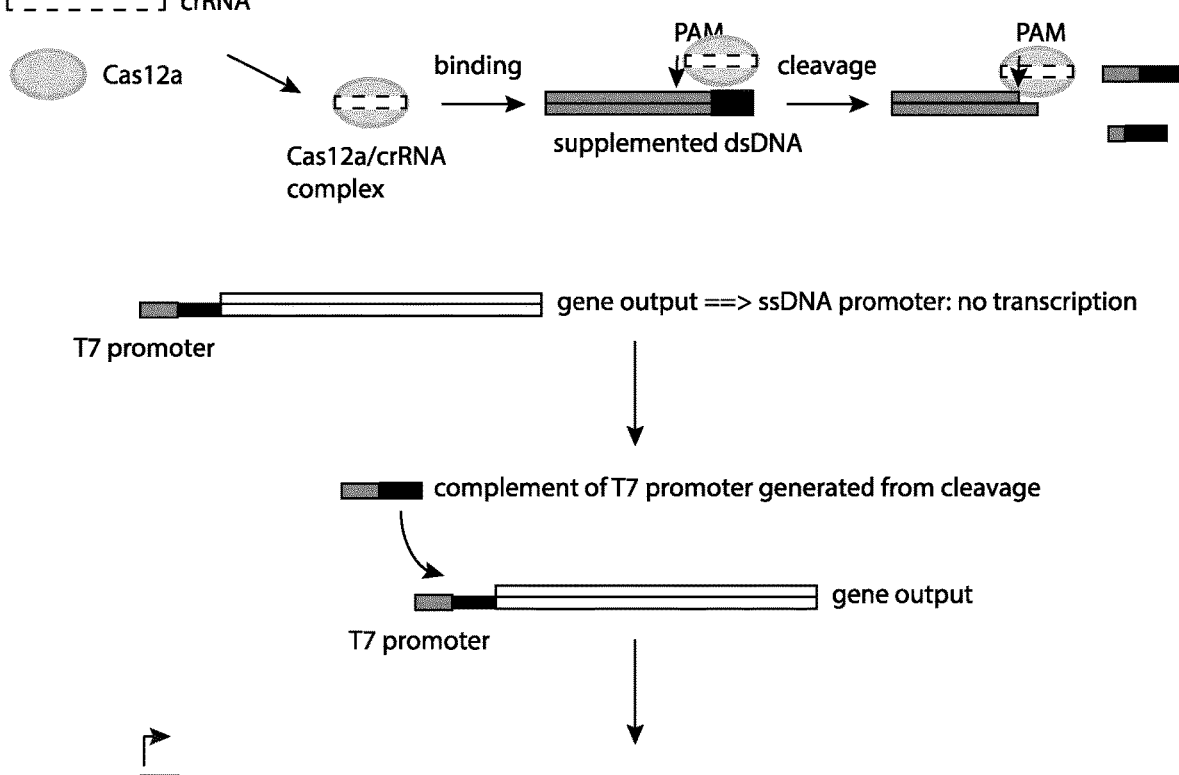

FIG. 12 is a schematic of strand replacement-based reporter system. Following production of the crRNA (dashed rectangle) and formation of the complex Cas/crRNA, supplemented dsDNA is bound by the complex and cleaved. Cas12a stays bound to the proximal dsDNA and the distal fragments are released. On one of the released fragments is the complement to the ssT7 promoter upstream the output gene. Following annealing, the T7 promoter is now dsDNA which allows correct transcription and translation of the output reporter.

Figure 13:
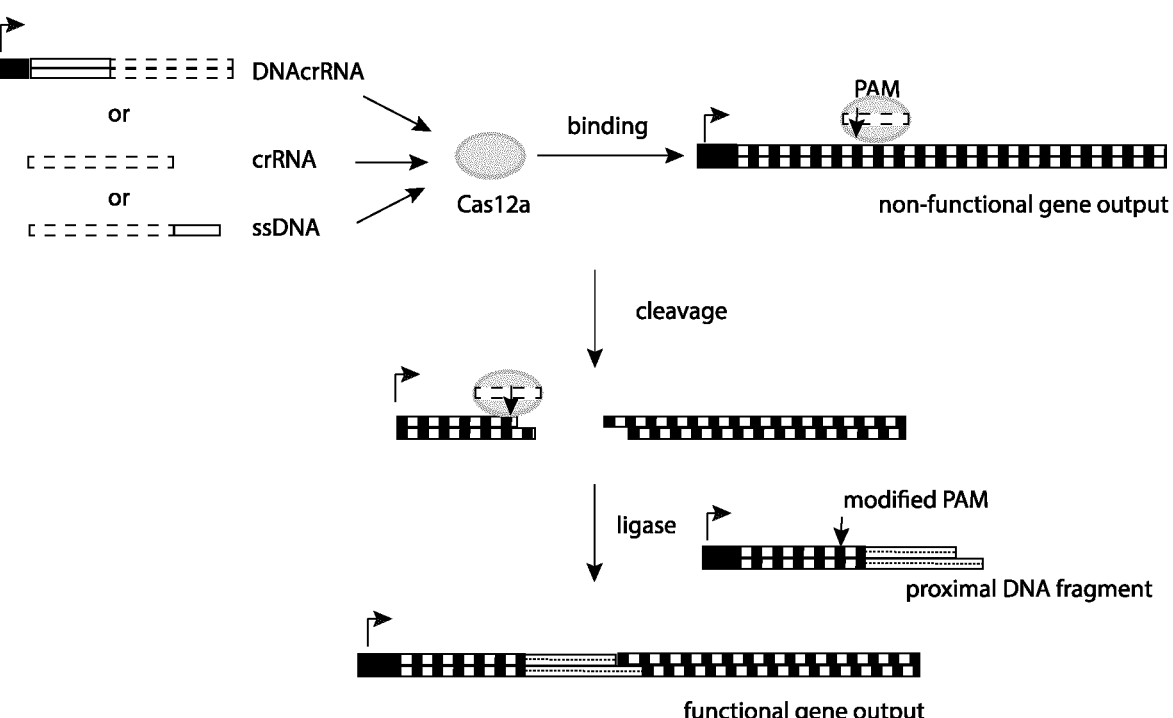
Figure 14A:
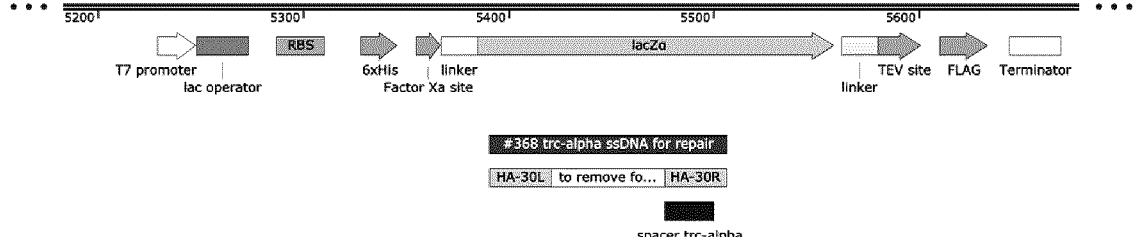

FIG. 13 is a schematic of cut-and-ligase based reporter system. Cas12a loaded with crRNA binds and cleaves a non-functional gene reporter. The distal DNA is released while the proximal fragment stays bound by Cas12a. Provided in the system is a ligase and a new proximal DNA fragment containing a modified PAM sequence for the new DNA to not be CRISPR sensitive, as well as the missing DNA to repair the gene (dotted rectangle). Once ligated together, the new proximal fragment and the distal one will form a functional gene output. Steps are explained in FIG. 1. Following the generation of a loaded/activated cas12 nuclease (via version ssDNA, crRNA or DNAcrRNA), the RePAIR process involves the cleavage of the non-functional DNA to enable DNA re-organization and ligation with the new proximal piece to form a functional gene FIG. 14a is a schematic of a map of pET15trcα used in the system described as Version 1;

FIG. 14b is a schematic of a map of pET15trc2α used in the system described as Version 1;

FIG. 14c is a schematic of a map of pET15trc3α used to generate the data shown in FIGS. 15h, 17h, 17i, 17j, 17k, 17l, 17n, 17o, 20a, 21a, 21b, 23a.

Figure 15E:
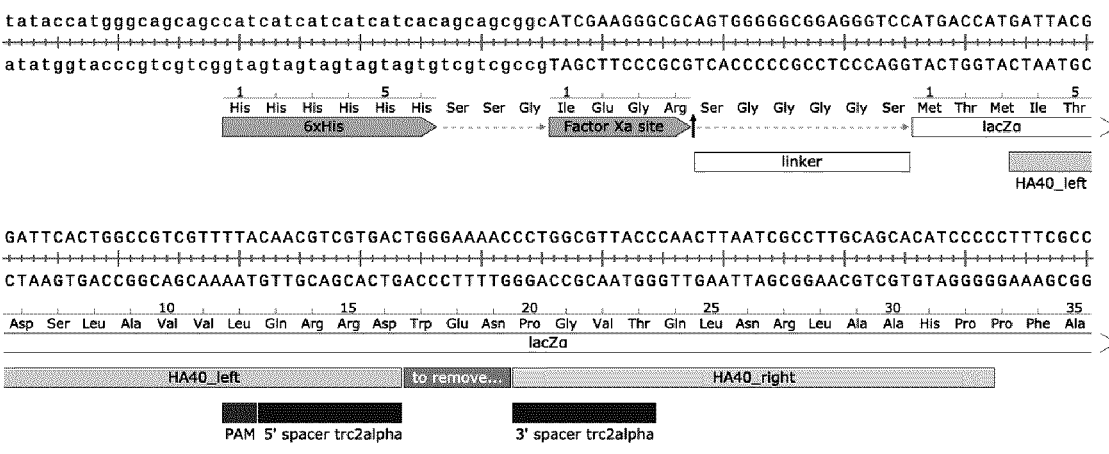
Figure 15F:
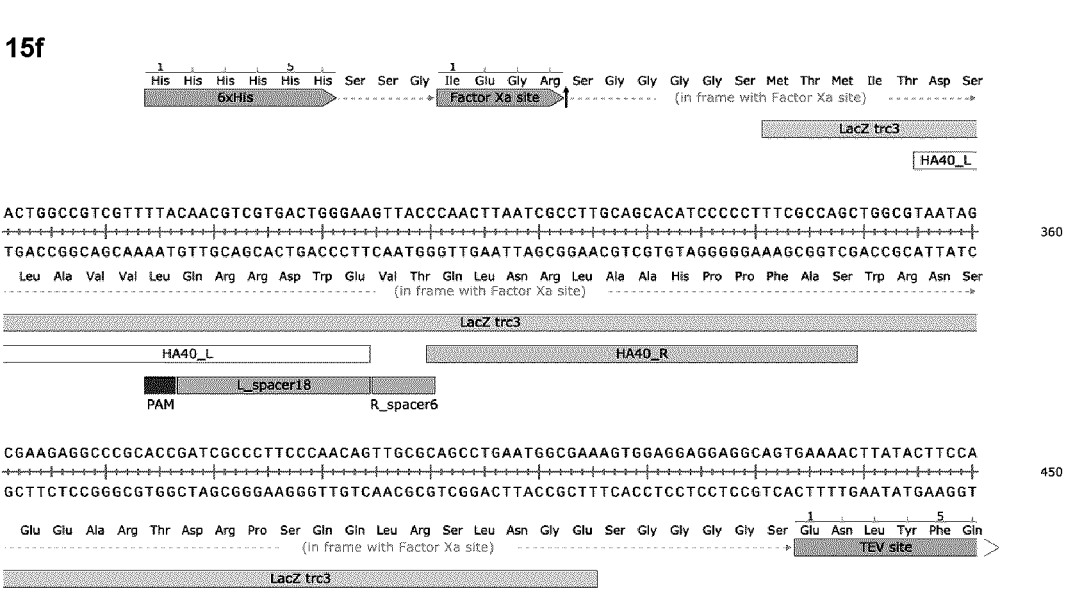
Figure 15G:
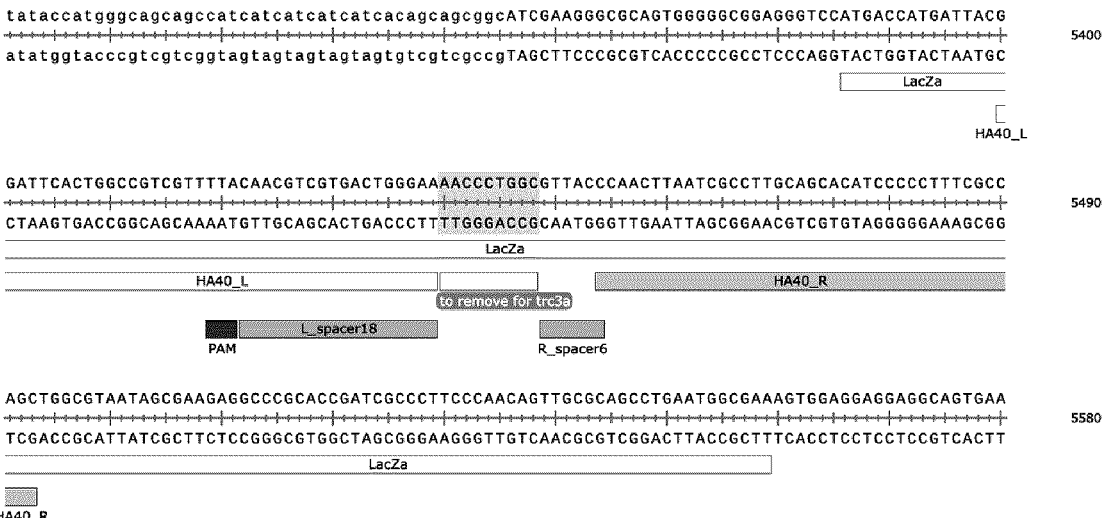
Figure 15H:
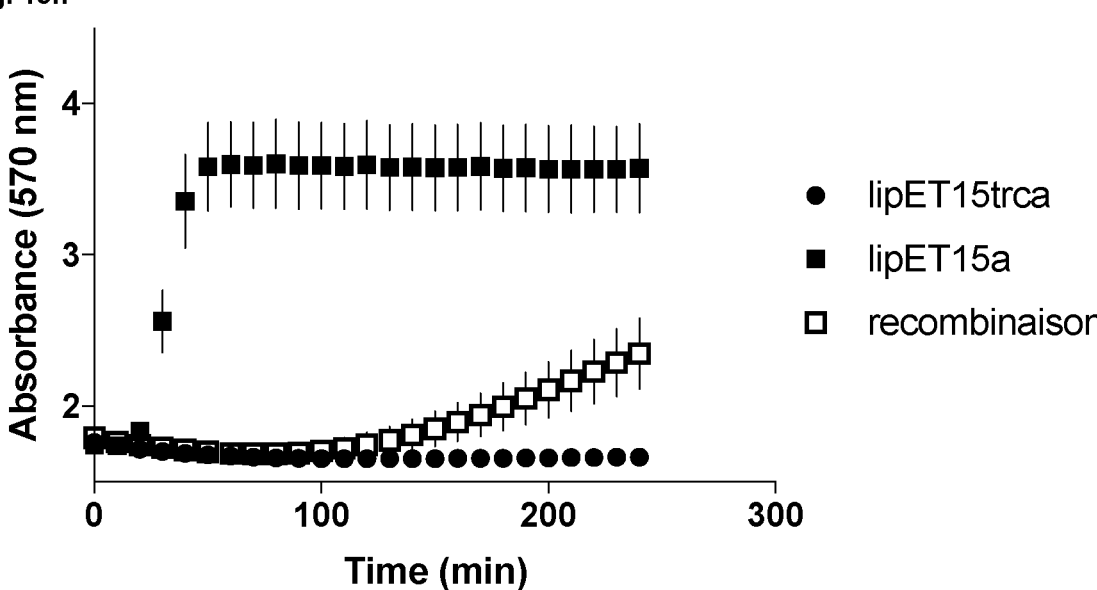
Figure 17A:
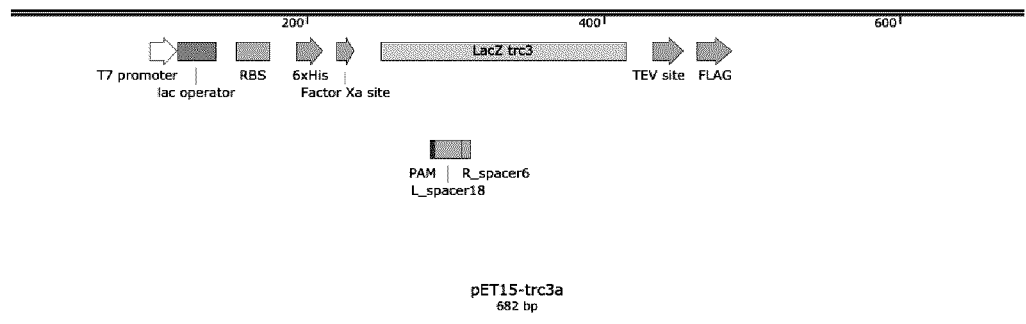
Figure 17B:
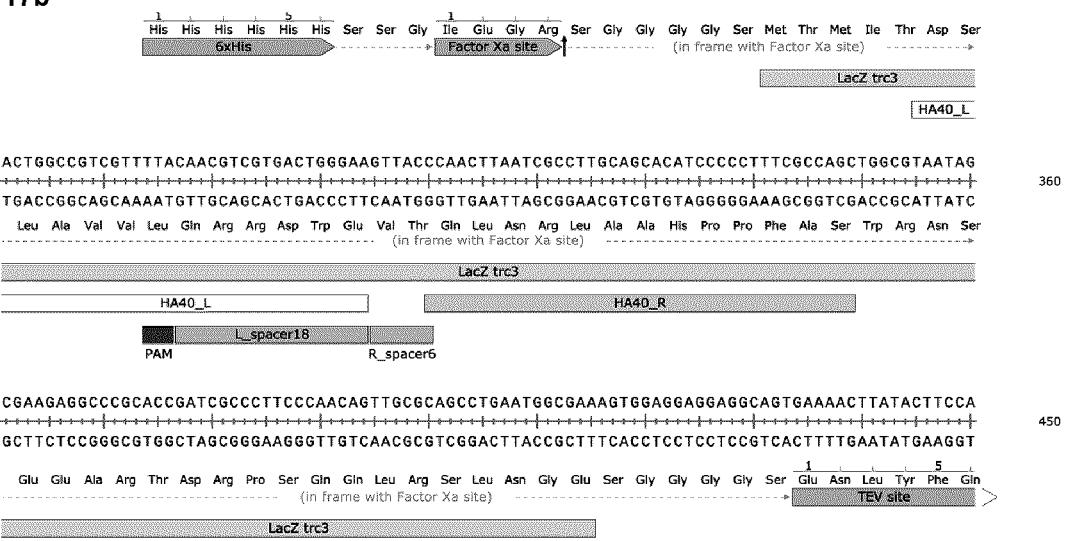
Figure 17C:
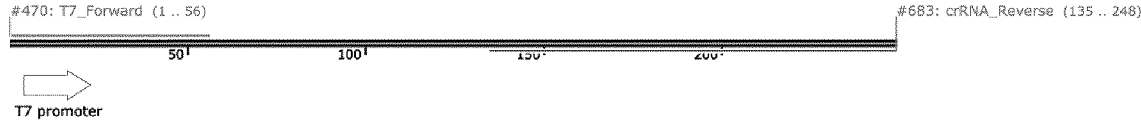
Figure 17G:
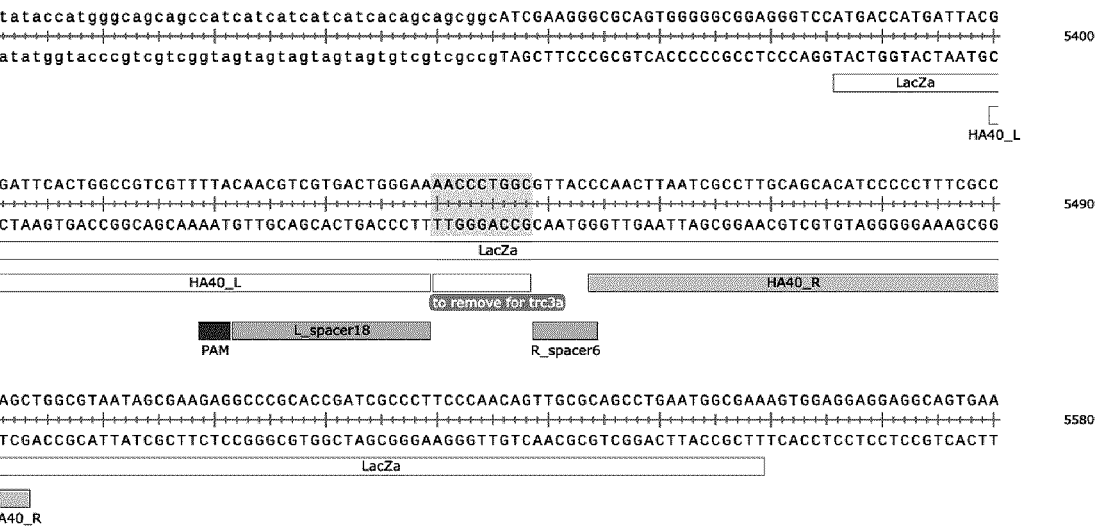
Figure 17H:
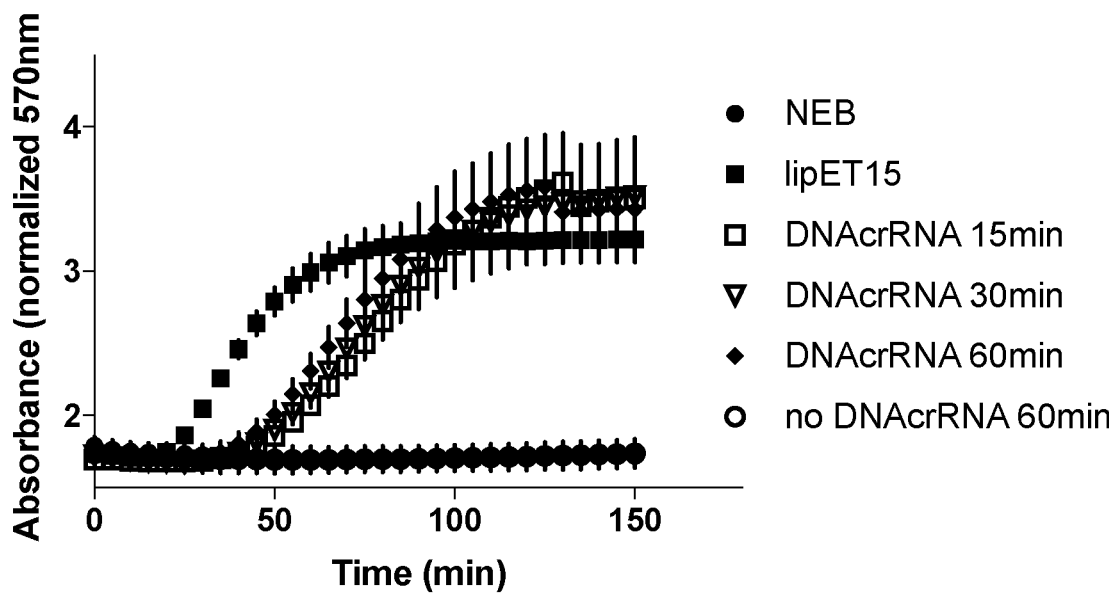

FIG. 15a is a schematic of the nucleotide sequence dsDNAcrRNAtrcα used in the system described as Version 1;

FIG. 15b is a schematic of the nucleotide sequence dsDNAcrRNAtrc2α used in the system described as Version 1;

FIG. 15c is a schematic of the nucleotide sequence dsDNAcrRNAtrc3α used to generate the data shown FIGS. 17h, 17n, and 17o;

FIG. 15d is a schematic of the nucleotide sequence to build pET15trcα used in the system described as Version 1;

FIG. 15e is a schematic of the nucleotide sequence to build pET15trc2α used in the system described as Version 1;

FIG. 15f is a schematic of the nucleotide sequence pET15trc3α used to generate the data shown in FIGS. 15h, 17h, 17i, 17j, 17k, 17l, 17n, 17o, 20a, 21a, 21b, 23a;

FIG. 15g is a schematic of the nucleotide sequence to build pET15trc3α used in the system described as Version 1;

FIG. 15h is a graph showing expression of LacZ and LacZ alpha reporters using ssDNA actuation of Cas12a.

Figure 16A:
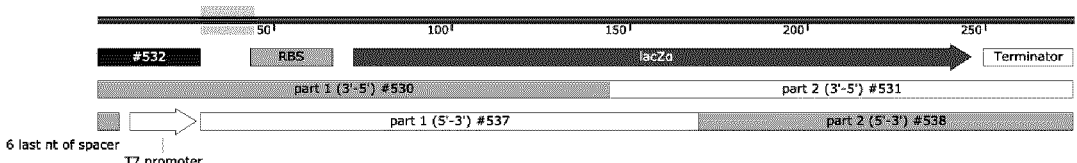
Figure 17I:
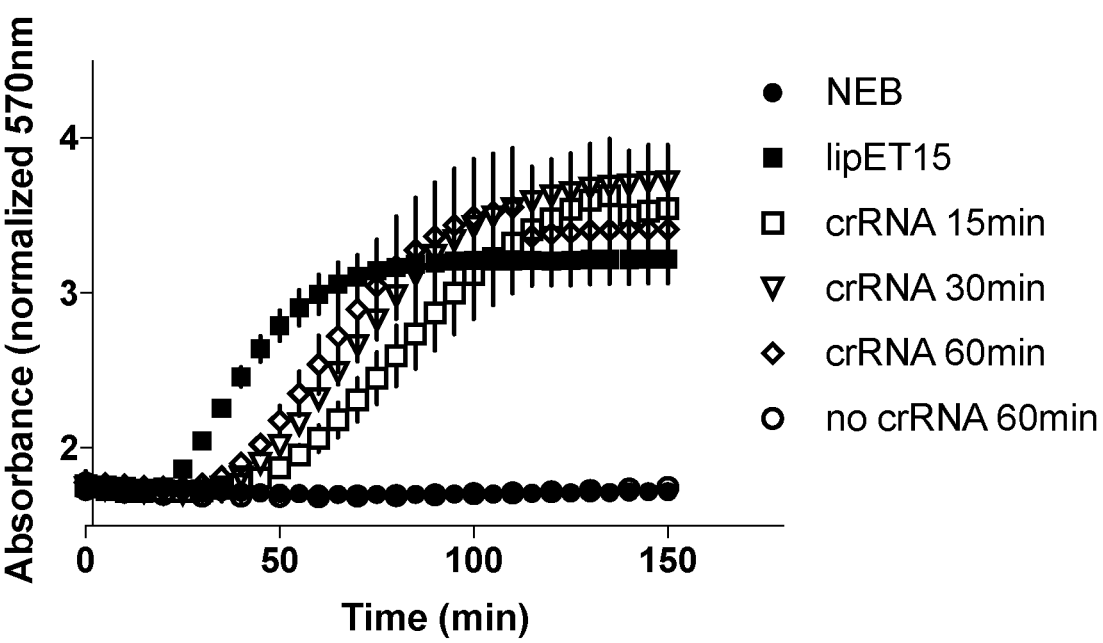
Figure 17J:
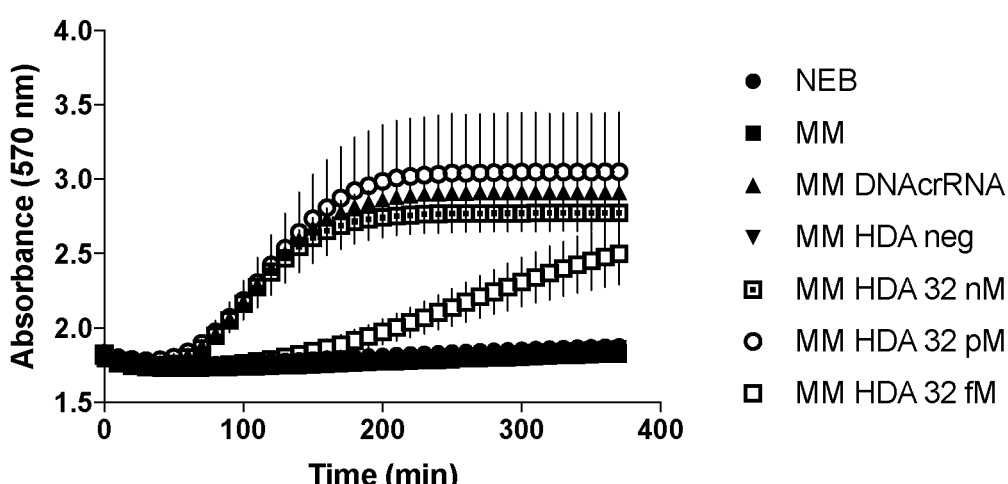

FIG. 16a is a schematic of a map of dsDNAalpha reporter used in the system described as Version 2;

FIG. 16b is a schematic of the nucleotide sequence dsDNAalpha used in the system described as Version 2;

FIG. 16c is a schematic of the dsDNAcrRNA synthetic sequence for use in the system described as Version 2;

FIG. 16d is a schematic of the supplemented dsDNA for displacement use in the system described as Version 2;

FIG. 17a is a schematic of the map pET15trc3α used in the system described as Version 3;

FIG. 17b is a schematic of the nucleotide sequence pET15trc3α used in the system described as Version 3;

FIG. 17c is a schematic of the map of amplification product pAz using #470-683 in the system described as Version 3;

FIG. 17d is a schematic of the nucleotide sequence of amplification product pAz using #470-683 in the system described as Version 3;

FIG. 17e is a schematic of the nucleotide sequence of proximal sequence (e.g. DNA repair fragment) used in the system described as Version 3;

FIG. 17f is a schematic of the nucleotide sequence dsDNAcrRNAtrc3α for use in the system described as Version 3;

FIG. 17g is a schematic of the nucleotide sequence to build pETtrc3α used in the system described as Version 3;

FIG. 17h is a graph of Signal ON with DNAcrRNAtrc3α detected using a RePAIR system described herein;

FIG. 17i is a graph of Signal ON with crRNAtrc3α detected using a RePAIR system described herein;

FIG. 17j is a graph of sensitivity for diagnostic DNA target using helicase-dependent amplification (HDA) amplification followed by detection using a RePAIR system described herein.

Figure 17K:
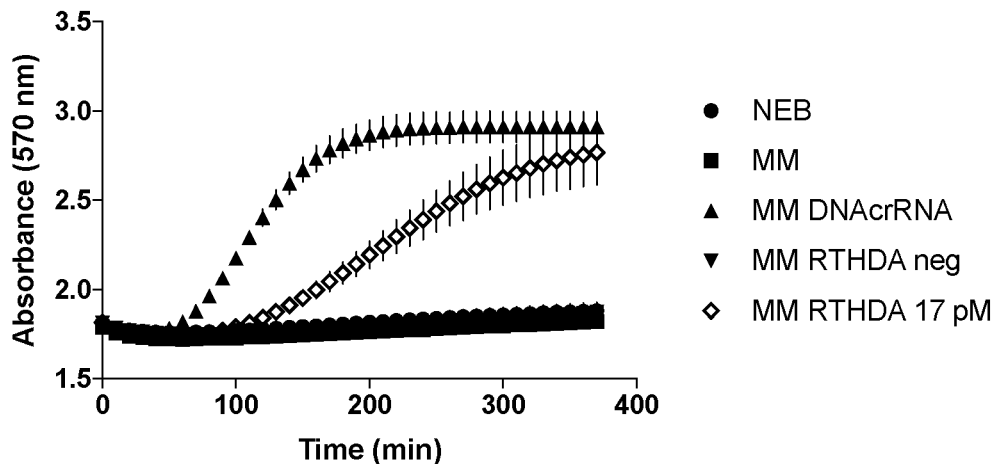

FIG. 17k is a graph of sensitivity for diagnostic target RNA using reverse transcription-helicase dependent amplification (RT-HDA) followed by detection using a RePAIR system described herein.

Figure 17L:
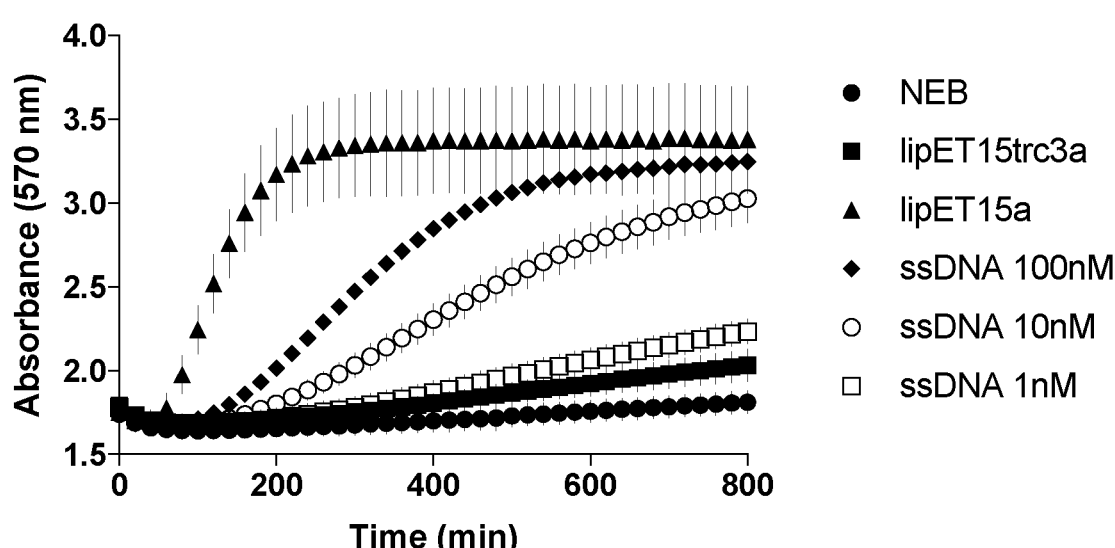

FIG. 17l is a graph of ssDNA involvement detected using a RePAIR system described herein; Varying concentrations of ssDNA #683 were used.

FIG. 17m is a schematic of nucleotide sequence #683.

FIG. 17n is a graph of sensitivity for dsDNAcrRNA with recombinase polymerase amplification (RPA) detected using a RePAIR system described herein.

FIG. 17o is a graph of sensitivity for dsDNAcrRNA with no RPA detected using a RePAIR system described herein.

FIG. 18 is a schematic of nucleotide sequence #518. Once a dsDNA is produced out of the amplification, crRNA is generated. The sequence of the spacer targets pET15a for signal OFF system.

FIG. 19a is a schematic of a molecular beacon (MB) for use in a cis-cleavage system.

Figure 19B:
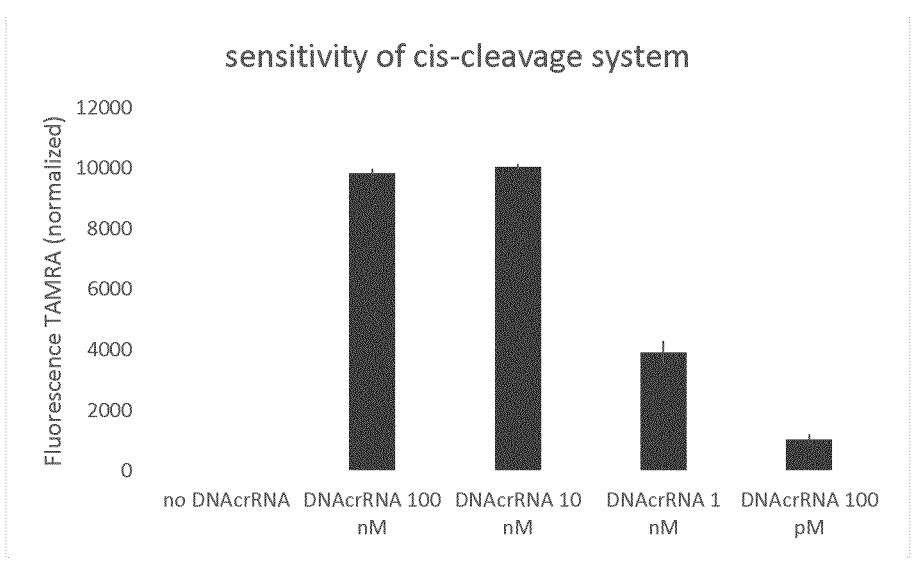

FIG. 19b is a graph of sensitivity of the cis-cleavage system demonstrating pM sensitivity using DNAcrRNA.

Figure 20A:
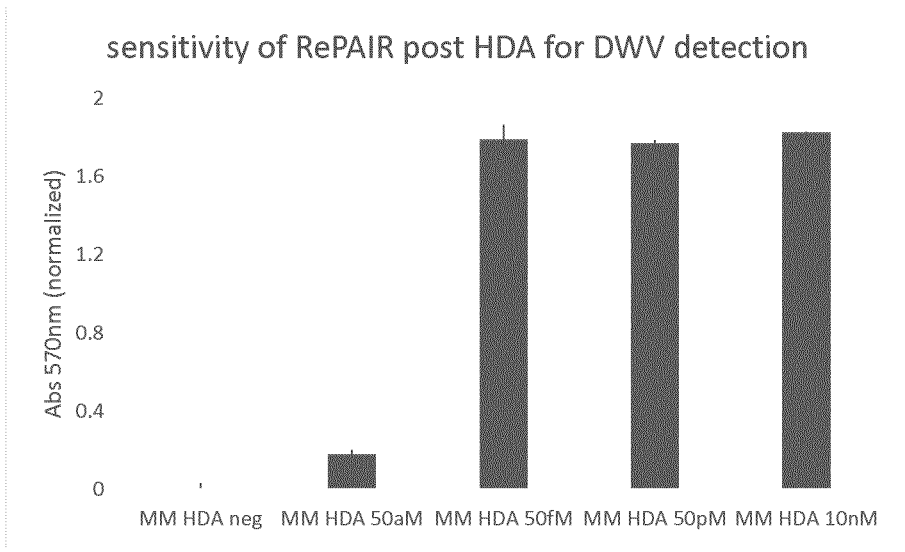

FIG. 20a is a graph of sensitivity of RePAIR for detection of DWV demonstrating aM sensitivity.

Figure 20B:
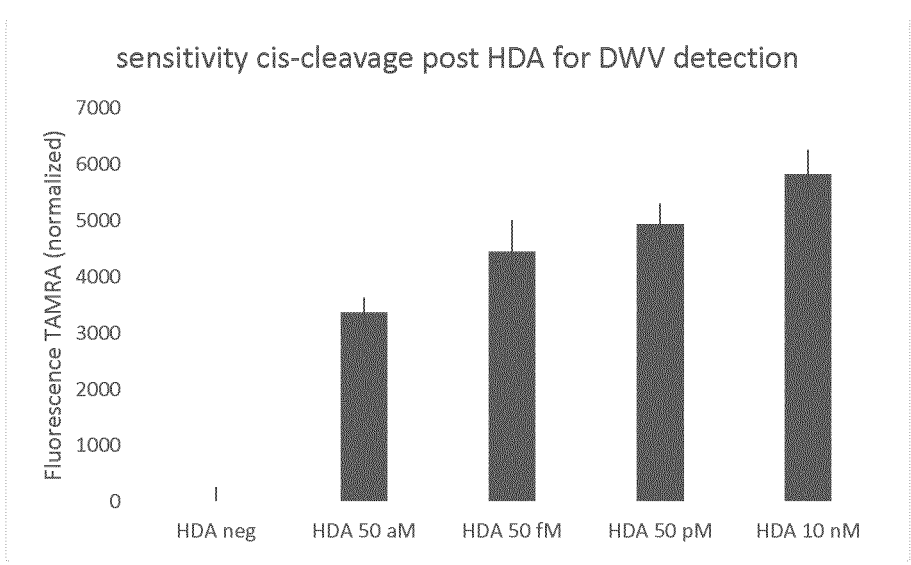

FIG. 20b is a graph of sensitivity of the cis-cleavage system for detecting synthetic DWV dsDNA demonstrating aM sensitivity.

Figure 21:
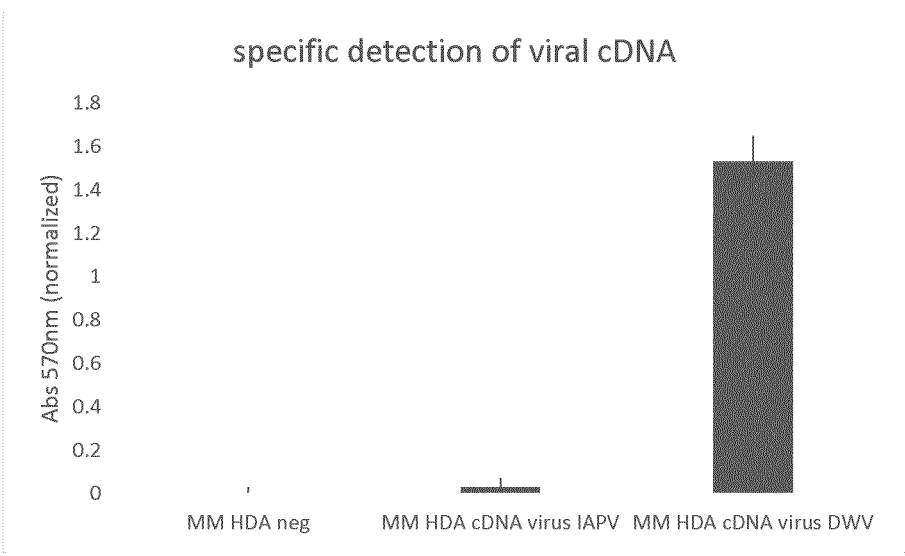

FIG. 21 is a graph of specificity of the RePAIR system for detecting DWV cDNA prepared from RNA extracted from cultured virus.

Figure 22:
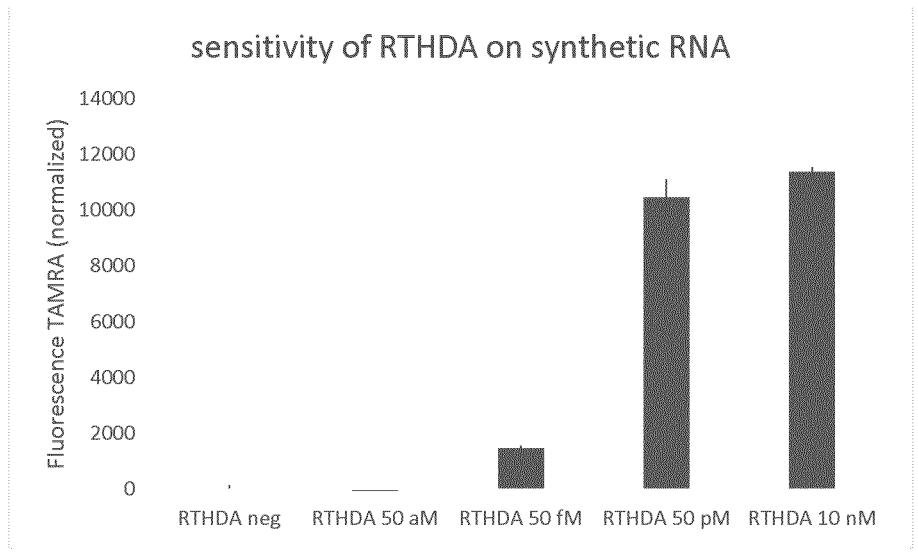

FIG. 22 is a graph of sensitivity of the cis-cleavage system using RT-HDA from synthetic RNA.

Figure 23A:
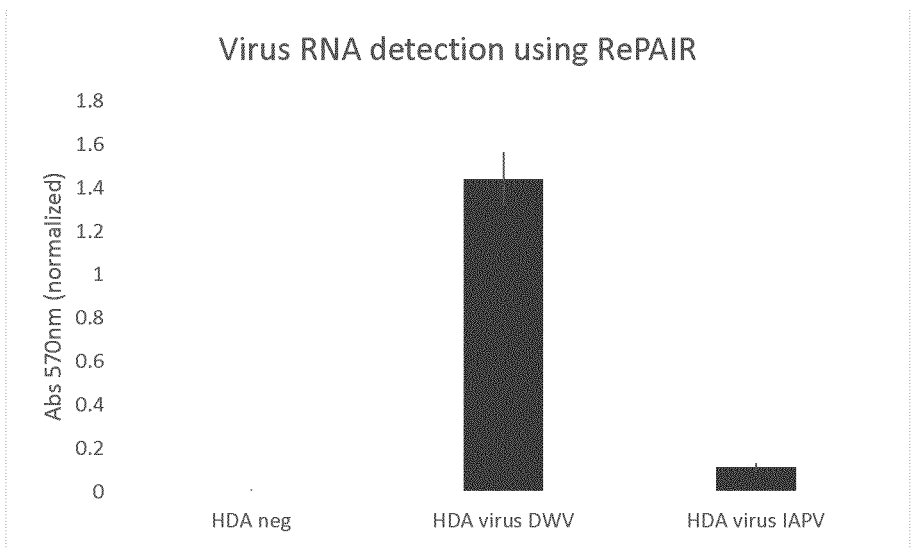

FIG. 23a is a graph of selectivity of the RePAIR system for detecting DWV using RT-HDA from RNA extracted from cultured virus.

Figure 23B:
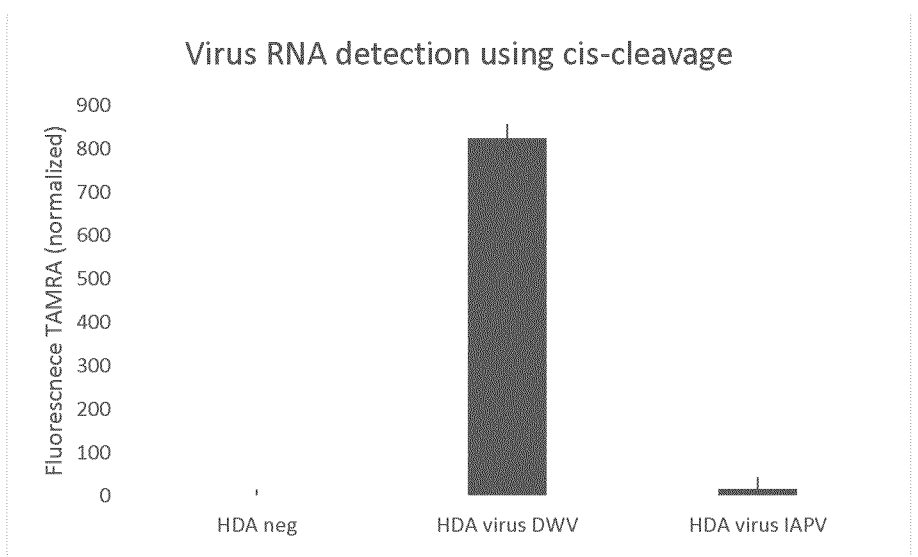

FIG. 23b is a graph of selectivity of the cis-cleavage system for detecting DWV using RT-HDA from RNA extracted from cultured virus.

Figure 24A:
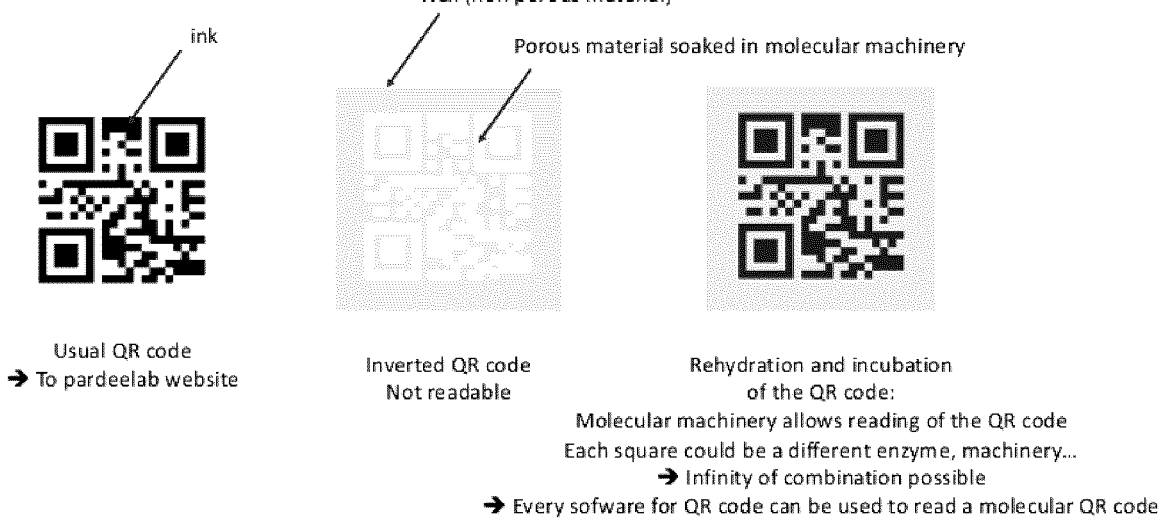

FIG. 24a shows a schematic of a molecular QR code.

Figure 24B:
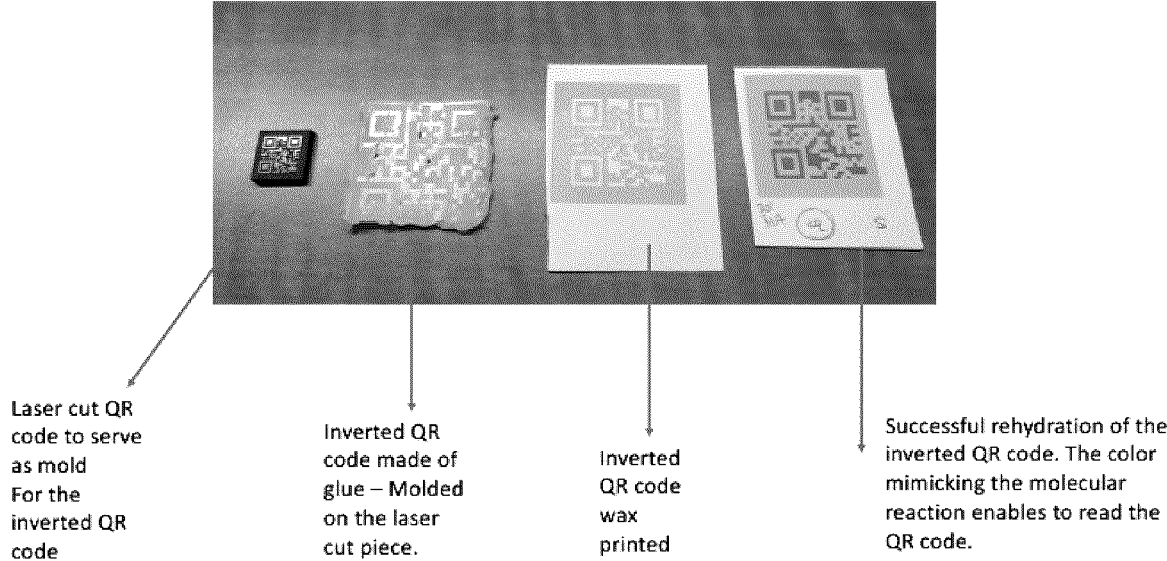

FIG. 24b shows different steps in generating a molecular QR code.

DESCRIPTION OF VARIOUS EMBODIMENTS

The following is a detailed description provided to aid those skilled in the art in practicing the present disclosure. Unless otherwise defined, all technical and scientific terms used herein have the same meaning as commonly understood by one of ordinary skill in the art to which this disclosure belongs. The terminology used in the description herein is for describing particular embodiments only and is not intended to be limiting of the disclosure. All publications, patent applications, patents, figures and other references mentioned herein are expressly incorporated by reference in their entirety.

I. DEFINITIONS

As used herein, the following terms may have meanings ascribed to them below, unless specified otherwise. However, it should be understood that other meanings that are known or understood by those having ordinary skill in the art are also possible, and within the scope of the present disclosure. All publications, patent applications, patents, and other references mentioned herein are incorporated by reference in their entirety. In the case of conflict, the present specification, including definitions, will control. In addition, the materials, methods, and examples are illustrative only and not intended to be limiting.

The terms "nucleic acid", "oligonucleotide", "primer" as used herein means two or more covalently linked nucleotides. Unless the context clearly indicates otherwise, the term generally includes, but is not limited to, deoxyribonucleic acid (DNA) and ribonucleic acid (RNA), which may be single-stranded (ss) or double stranded (ds). The nucleic acids can be any length depending upon the application, for example from 30 bp to 8 kb or longer, optionally up to 200 base pairs in length or for example up to 8 kb or longer, and may be single-stranded or double-stranded.

The term "primer" as used herein generally refers to single-stranded DNA for example from about 30 to up to 200 base pairs in length that can be used to produce an amplification product based on annealing to a segment of a target nucleic acid to be amplified. As will be understood by the skilled person, primers must be oriented in such a way as to permit amplification of the target sequence.

Primers may also be used to introduce a desired sequence into an amplification product. For example, inclusion of a desired sequence such as a promoter sequence or a sequence encoding a crRNA in the 5' end of a primer can be used to produce an amplification product having the promoter sequence or sequence encoding a crRNA at an end of the amplification product. Accordingly, the term "promoter primer" is used to describe a primer comprising, from 5' to 3', a promoter sequence, and a proximal detection target segment which has, or is complementary to, the sequence of a proximal portion of the target sequence. The term "crRNA primer" is used to describe a primer comprising, from 5' to 3', a sequence encoding a crRNA, and a distal detection target segment which has, or is complementary to (e.g. reverse complement of), the sequence of a distal portion of the target sequence.

The primer can also be arrayed as described herein.

The term "target nucleic acid" refers to a nucleic acid of interest and can include a nucleic acid being amplified or being detected such as a diagnostic target. For example, the target nucleic acid can be an organism-specific nucleic acid sequence useful for detecting the presence of an organism or group of organisms; a strain-specific nucleic acid sequence useful for distinguishing between different strains of an organism; a nucleic acid sequence associated with drug resistance; or a nucleic acid sequence present in a physiological or pathological condition. A target nucleic acid can be naturally occurring or synthetic (e.g. molecular barcode) and may include genomic DNA, circular DNA, messenger RNA, ribosomal RNA, or any other nucleic acid, and may be genomic DNA, circular DNA, messenger RNA, ribosomal RNA, or any other nucleic acid. Where the target nucleic acid is an RNA, the target RNA may be converted to for example cDNA before being amplified and/or detected. This may be accomplished for example by reverse transcription.

With reference to nucleic acids, the terms "anneal" and "hybridize" as used herein refer to the ability of a nucleic acid to non-covalently interact with another nucleic acid through base-pairing. The terms "complementary" or "complementary nucleic acid" refer to a nucleic acid or a portion of a nucleic acid that is able to anneal with a nucleic acid of a given sequence. In some cases this is referred to as the "reverse complement" of a given sequence.

The term "CRISPR-Cas" as used herein refers a CRISPR Clustered Regularly Interspaced Short Palandromic Repeats-CRISPR associated protein (CRISPR-Cas) protein that loads RNA and is targeted to a specific DNA sequence by the RNA to which it is bound. CRISPR-associated systems or Cas genes, code for Cas proteins which have helicase and nuclease activities (e.g. Cas9, Cas12a/CPF1, Cas13, Cas14). Cas proteins that are suitable for embodiments of the present disclosure have the feature of being RNA-guided nucleases, although ssDNA-guided nucleases are also suitable. In addition, in some embodiments the Cas protein(s) is able to load guide RNA from a larger RNA strand (in other embodiments, for example in the case of Cas9, the system is supplemented with a RNAseIII enzyme). Native Cas12a (also known as Cpf1) is capable of recognizing the crRNA when the spacer sequence is flanked by direct repeats, minimally for example having an upstream direct repeat, and can therefore load itself. Once loaded with the guide RNA, the addressable Cas protein associates with dsDNA complementary to the guide RNA and cleaves the dsDNA using its nuclease activity. The Cas protein can be a nickase, in that nuclease domains of the Cas nuclease is mutated independently of each other thereby creates DNA "nickases" capable of introducing a single-strand cut with the same specificity as a regular CRISPR-Cas nuclease. The use of Cas9 nickases or Cas12a nickases is essentially the same as the use of the fully functional enzyme, with the difference in that nickase introduces gRNA-targeted single-strand breaks in DNA instead of the double-strand breaks created by wild type Cas enzymes.

The terms "crRNA," "guide RNA", "gRNA", or "sgRNA" (single-guide RNA) as used herein refer to an RNA molecule that binds to the CRISPR-Cas protein and a specific DNA sequence. A crRNA comprises a protein binding segment (e.g. direct repeat) that binds the CRISPR-Cas protein, and a DNA-targeting sequence, or spacer sequence, that is complementary to a specific CRISPR target sequence. The nucleotide sequence of the spacer sequence determines the CRISPR target sequence and can be designed to target any desired CRISPR target site.

As used herein, the term "crRNA-encoding nucleic acid" means a nucleic acid molecule that can be used to generate a crRNA. The crRNA encoding nucleic acid can be a ssDNA that encodes a crRNA or a ssDNA that can be processed or functions as a crRNA. It can also be a DNAcrRNA where a "DNAcrRNA" is a double stranded DNA molecule minimally comprising a promoter—full direct repeat (DR)—spacer—$1^{st}$ half DR, and is a crRNA-encoding nucleic acid.

The various nucleic acids, for examples primer, oligonucleotide inserts, crRNA or DNA encoding crRNA can be provided in an array, for example, an array having multiple repeats of a primer. For example the array can comprise up to 8000 base pairs, up to 7000 base pairs, up to 6000, for example 200 base pairs comprising repeats of the primer or other nucleic acid. In such a case, an individual primer or other nucleic acid can be released from the array upon cleavage. The arrays in some embodiments comprise one or more direct repeats and spacers oriented to be processed by Cas enzymes releasing the primers.

For example the CRISPR DNA array can comprise $1^{st}$ halfDR-$2^{nd}$ halfDR-spacer-$1^{st}$ halfDR-$2^{nd}$ halfDR, where $1^{st}$ and $2^{nd}$ half of the DR makes a fullDR. A crRNA (i.e. processed from an array) is $2^{nd}$ halfDR-spacer-$1^{st}$ halfDR. It is the recognition of the fullDR by Cas12a that induces cleavage at halfDR. In a DNA array it is fullDR-spacerfullDR-spacer2-fullDR-spacer3-fullDR, which generates $2^{nd}$ halfDR-spacer1-$1^{st}$ halfDR and $2^{nd}$ halfDR-spacer2-$1^{st}$ halfDR. DNAcrRNA minimally comprises a promoter-fullDR-spacer-$1^{st}$ halfDR. When the RNA is produced, Cas12a binds to the fullDR and cleaves the RNA, while loading the processed crRNA. It recapitulates exactly what is happening for the primers containing the sequence of crRNA. In the absence of fullDR, the crRNA is not processed because Cas12a does not recognize the crRNA sequence. Several lengths can be designed for the spacer, for example 16 nt or 24 nt. The skilled person can readily recognize the appropriate space lengths for Cas9, Cas13, and Cas14. In some embodiments, concentration of DNAcrRNA in recombinase polymerase amplification (RPA) is from about 1 fM to about 100 nM, or about 10 fM to about 10 nM, or about 100 fm to about 5 nM. In some embodiments, concentration of DNAcrRNA in a method described herein is from about 1 fM to about 100 nM, or about 10 fM to about 10 nM, or about 100 fm to about 5 nM.

The terms "CRISPR target site" or "CRISPR-Cas target site" as used herein mean a nucleic acid sequence to which an activated CRISPR-Cas protein will bind. A CRISPR target site comprises a protospacer-adjacent motif (PAM) and a protospacer (CRISPR target sequence (i.e. complementary to the spacer sequence of the crRNA to which the activated CRISPR-Cas protein is bound)). The sequence and relative position of the PAM with respect to the CRISPR target sequence depends on the type of CRISPR-Cas protein. For example, Cas12a PAM sites are T-rich regions, such as "TTN". In comparison, Cas9 PAM sites are G-rich. However, alternate PAM sequences exist, as other Cas proteins may share the necessary features to carry out the mechanisms described in this disclosure. For Cas12a, the target sequence is 5'-PAM-protospacer-3', and depending on the Cas12a species, the PAM can be TTTN or TTN. For Cas9, the target sequence is 5'-protospacer-PAM-3', where PAM can be 5'-NGG-3'. For Cas13, the target sequence is also 5'-protospacer-PAM-3', where PAM is a single nucleotide A, U or C. Additional PAMs are known. The skilled person can readily recognize suitable and/or modified PAM to increase the ability of Cas for genome editing, including to prevent binding of Cas to a "repaired" nucleic acid.

The term "active CRISPR-Cas effector protein" as used herein refers to a CRISPR-Cas protein bound to a crRNA or crDNA and which is capable of binding and modifying a CRISPR target site. CRISPR-Cas proteins may modify the nucleic acid to which they are bound for example by cleaving one or more strands of the nucleic acid. The term "cleaving" or "cleavage" means breaking or severing the covalent bond between two adjacent nucleotides. In some cases this means breaking the covalent bond between two adjacent nucleotides in a single nucleic acid strand. In other cases this means breaking the covalent bond between two adjacent nucleotides in both strands of a double-stranded nucleic acid. Where cleavage occurs in both strands of a double stranded nucleic acid, the resulting ends may be blunt or may have overhanging ends. Accordingly, the term "CRISPR-sensitive" as used herein means a nucleic acid comprising a CRISPR target site that may be modified by an active CRISPR-Cas effector protein.

The term "signal-generating CRISPR-sensitive reporter" as used herein means any reporter that can generate a signal and is CRISPR sensitive including for example existing reporters such as molecular beacons and the CRISPR-sensitive DNA sensors described herein.

The term "molecular beacon" refers to a type of CRISPR-sensitive reporter comprising for example a fluorophore, a quencher, and a CRISPR-sensitive nucleic acid linker. Cleavage of the linker by activated Cas allows the fluorophore and quencher to separate, resulting in a detectable signal. The CRISPR sensitive nucleic acid linker can for example be double stranded, optionally a dsDNA, or a RNA:DNA hybrid. Further the fluorophore and the quencher can be opposite each other, for example with the quencher coupled to the 3' end of a strand and the fluorophore coupled to the 5' end of the complementary strand or vice versa. A variety of molecular beacons are known and can be used in the methods and in systems and other products described herein when the molecular beacon comprises a CRISPR-sensitive nucleic acid linker. For example the molecular beacon can be a non-functional DNA reporter construct comprising a double stranded linear DNA comprising a first DNA strand coupled to a fluorochrome at its 3' end and a second DNA strand hybridized to the first DNA strand and compromising a quencher molecule, the quencher molecule coupled to the 5' end of the second DNA strand, the double stranded linear DNA comprising a CRISPR site.

The term "promoter" or "promoter sequence" generally refers to a regulatory DNA sequence capable of being bound by an RNA polymerase to initiate transcription of a downstream (i.e. 3') sequence to generate an RNA. Suitable promoters may be derived from any organism and may be bound or recognized by any RNA polymerase. Exemplary promoters include, but are not limited to, a SP6 promoter, a T7 promoter, and a T3 promoter.

The term "reporter gene" also referred to as a "reporter cassette" as used herein means a DNA molecule that when transcribed, or, transcribed and translated produces a readily assayable molecule. The readily assayable molecule can for example be a non-coding RNA molecule such as a ribozyme, aptamer, or a crRNA or a protein. Suitable proteins include, but are not limited to, a fluorescent protein, a luminescent protein, a chromoprotein, an electrochemically active protein, an affinity protein, or an enzyme. Examples of reporter cassettes that produce color include enzymes such as beta-galactosidase, horseradish peroxidase, cytochrome B562, beta-glucuronidase, and alkaline phosphatase. Color can also be generated from chromogenic proteins such red fluorescent protein, cjBlue, aeBlue, amilGFP and amilCP. Common fluorescent proteins include Green fluorescent protein (GFP), mCherry, yellow fluorescent protein (YFP) and cyan fluorescent protein (CFP), among many others. Common luminescent proteins include firefly luciferase and renilla luciferase. Affinity proteins include a wide range of proteins that bind to target analytes, which include antibody/antigen and receptor/ligand interactions or streptavidin/biotin, among others. Enzymes as a general class could serve as reporter genes, which include those used routinely in assays, such as beta-galactosidase, horseradish peroxidase and alkaline phosphatase, as well as many others that catalyze observable signals, e.g. kinases, proteases, etc. Electrochemically active proteins that catalyze reactions that produce or consume electrons and include glucose oxidase and horseradish peroxidase, among others. Electrochemical outputs would include the generation of any redox enzyme (e.g. glucose oxidase, but many others) or cleavage event that causes an electrochemical signal on an electrode (e.g. DNA cleavage leads to recruitment of methylene blue to the surface of an electrode; see FIG. 3d in Mousavi et al. 2019).

The terms "expression cassette" as used herein refer to a reporter gene that is operably linked to a promoter (i.e. a functional expression cassette) or is a non-functional expression cassette.

The term "operably linked" as used herein refers to a relationship between two components that allows them to function in an intended manner. For example, where a reporter gene is operably linked to a promoter, the promoter actuates expression of the reporter gene.

The terms "non-functional expression cassette" and "non-functional reporter construct" respectively mean an expression cassette and a reporter construct in which a reporter gene is not operably linked to a promoter or which produces an expression product with that is not active, or that is missing a transcription factor (i.e. when crRNA is produced as a result of molecular barcode or presence of target nucleic acid, it is loaded into a dead Cas9 (dCas9) linked to a transcription factor; only then, would the dCas9 localize to the functional gene and allow transcription), or that is linked to a ssDNA promoter. It is not necessary that the promoter is always missing. The interruption of function could also be the result of a stop codon, non-sense sequence or missing sequence at other key sites in the construct or reporter protein or aptamer/ribozyme, etc. Examples of key sites include enzyme catalytic sites, structurally critical sequences or links between domains, binding domains of affinity proteins, or binding domains for ligands, prosthetic groups or small molecules. For example, the non-functional expression cassette may be missing the promoter sequence or portion thereof, or may be missing the reporter gene or a portion thereof. In one example the reporter gene may be missing a transcriptional start site. In another example, the reporter gene may encode a protein with a desired function, but be modified in such a way as to prevent the translation of a functional protein. Such modifications include, but are not limited to, the removal of the start codon, the introduction of a premature stop codon, the introduction of a frame-shift mutation, or the removal of the sequence encoding one or more amino acid residues required for protein function. A premature stop codon or frame-shift mutation can be introduced by the inclusion of a stretch of nucleic acids referred to herein as a "function-blocking region."

The term "function-restoring nucleic acid" means a nucleic acid having a sequence that can be used to restore function (e.g. through function restoring repair) to the non-functional expression cassette. For example, in a case where the non-functional expression cassette is missing a portion of the reporter gene, the function-restoring nucleic acid may comprise the missing portion. In a case where the reporter is repaired by homology directed repair (HDR), the function-restoring nucleic acid may further comprise an upstream homology arm and a downstream homology arm, having sequences that correspond to the sequence of the reporter gene upstream and downstream, respectively, of the missing portion. Homology arms may be any suitable length that allows for HDR, for example the homology arms may be 30 bp, 40 bp, 50 bp, or any other suitable number of base pairs in length.

The term "cell-free system" as used herein means a set of reagents that are necessary and sufficient to carry out a specified in vitro biochemical reaction or process. Such reactions may include, but are not limited to, transcription reactions, translation reactions, energy (ATP) regeneration, function restoring repair of DNA such as ligation, recombination, or strand-displacement repair. The cell free system could also include isothermal amplification reaction components (including but not limited to components for isothermal amplification method including NASBA, HDA, RPA, LAMP, etc), DNA polymerase (e.g. AMV-RT for NASBA), components for DNA repair (e.g. components for double strand break repair), etc. Accordingly, as used herein, "components for transcription" means a set of reagents that are necessary and sufficient to support a transcription reaction. Such reagents include ribonucleotides and a buffer system. Required components also include a promoter-containing DNA and an RNA polymerase where such components are not otherwise provided for. As used herein, "components for translation" means a set of reagents that are necessary and sufficient to support a translation reaction. Such reagents include ribosomes, aminoacyl transfer RNAs, translation factors, and a buffer system. Required components also include an RNA template where such components are not otherwise provided for. As used herein, "components for repairing" means a set of reagents that are necessary and sufficient to support DNA repair. In some cases DNA repair may be carried out using T4 DNA ligase, and the reagents include a T4 ligase and a buffer system. Different categories of reporter have been designed that can be used with the methods described herein. For example categories referred to as Version 1, Version 2 and Version 3 are described in greater detail in the Examples. Exemplary reagents and components for these versions are provided in Table 2.

The phrase "components for generating signal from the signal-generating CRISPR-sensitive reporter" refers to components necessary for generating signal from a signal-generating CRISPR-sensitive reporter that is known to a person skilled in the art. The components necessary to generate the reporter signal are varied and dependent on the mode of the reporter. For example: 1) when the reporter is GFP, a cell-free transcription and translation system would be used to convert the repaired reporter gene (DNA) into RNA and the GFP protein; 2) when the reporter is an enzyme (e.g. LacZ), a cell-free transcription and translation system to convert the repaired reporter gene (DNA) into RNA and the enzyme, and exposure to a substrate of the enzyme thereby generating the signal; 3) when the reporter is an RNA aptamer (e.g. Spinach), a cell-free enzyme for RNA transcription (e.g. T7 RNApol) would be used, along with the spinach dye (e.g. DFHBI).

A cell free system described herein may also include reagents for generating a detectable signal. For example, a signal-inducing sensor described herein may encode an enzyme such as beta-galactosidase, and the cell-free system may include a chemical substrate of beta-galactosidase.

The term "physical substrate" as used herein refers to a material on which a process can be conducted.

The physical substrate can for example comprise one or more components described herein necessary for performing an assay described herein compartmentalized on the surface of a physical substrate forming an array. For example as shown in FIG. 9b the array can comprise a plurality of target DNA (e.g. unique ssDNA) molecules spatially localized, the plurality of target DNA molecules comprising a plurality of known sequences that are complementary to different reporter signal sequences, allowing discrimination between multiple CRISPR sensing reactions. Such systems allow for example the monitoring of a large number of targets (e.g. diagnostic targets) and/or greater complexity for example of DNA barcoding systems, making such systems more secure.

The term "additional discrete reporter system" as used herein another reporter such as another signal-generating CRISPR-sensitive reporter where the signal in the another signal-generating CRISPR-sensitive reporter is different than any other signal produced by other signal-generating CRISPR-sensitive reporters being used, for example in multiplexing applications.

Where a range of values is provided, it is understood that each intervening value, to the tenth of the unit of the lower limit unless the context clearly dictates otherwise, between the upper and lower limit of that range and any other stated or intervening value in that stated range is encompassed within the description. Ranges from any lower limit to any upper limit are contemplated. The upper and lower limits of these smaller ranges which may independently be included in the smaller ranges is also encompassed within the description, subject to any specifically excluded limit in the stated range. Where the stated range includes one or both of the limits, ranges excluding either both of those included limits are also included in the description.

It must be noted that as used herein and in the appended claims, the singular forms "a", "an", and "the" include plural references unless the context clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

All numerical values within the detailed description and the claims herein are modified by "about" or "approximately" the indicated value, and take into account experimental error and variations that would be expected by a person having ordinary skill in the art.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The term "about" as used herein means plus or minus 0.1 to 15%, preferably between about 0.1-10%, for example about 5% of the number to which reference is being made It should also be understood that, in certain methods described herein that include more than one step or act, the order of the steps or acts of the method is not necessarily limited to the order in which the steps or acts of the method are recited unless the context indicates otherwise.

Although any methods and materials similar or equivalent to those described herein can also be used in the practice or testing of the present disclosure, the preferred methods and materials are now described.

II. METHODS

I. crRNA Production

CRISPR proteins are RNA-guided nucleases that use a bound RNA (crRNA) to direct the enzyme to target complementary DNA sequences. With other CRISPR-related sensors (e.g. SHERLOCK), crRNAs must be stored and distributed along with the diagnostic kit, which can pose a challenge to their practical implementation.

The methods described herein include embodiments comprising in vivo modification of a target gene. Such modification can provide for example synchronization of process to endogenous gene expression. For example, it can involve adding in the target gene's 3'UTR or any other non-coding RNA sequences a sequence encoding a crRNA (fullDR-spacer-halfDR), thereby allowing production of a composite RNA which contains the target RNA and the crRNA. The composite RNA would in the presence of a Cas enzyme be recognized and loaded for downstream applications, for example, in vivo monitoring of processes. For instance, when a target is produced, crRNA is generated, which allows cleavage and repair of, for example, a GFP gene. Therefore, in this example when GFP is detected, target was produced. Several in vivo applications are described in the Examples. For example, a crRNA can be designed to target a gene necessary for a particular differentiation pathway, or a gene that would be overexpressed in cancer lines. Upon in vivo dsDNA break repair, in the absence of DNA template to repair the induced break, the non-homologous end joining (NHEJ) pathway introduces indel errors into the coding sequence, which inhibits the expression of the gene. If a dsDNA template is provided for the repair of the induced break, homologous recombination such as the "Version 1" system described herein could be employed, and in vivo expression would be produced with a repaired gene, for example, GFP. Also, sequential activation of gene expression allows for production of a first gene and then the repairing of a second gene based upon the production of the first gene.

Figure 1:
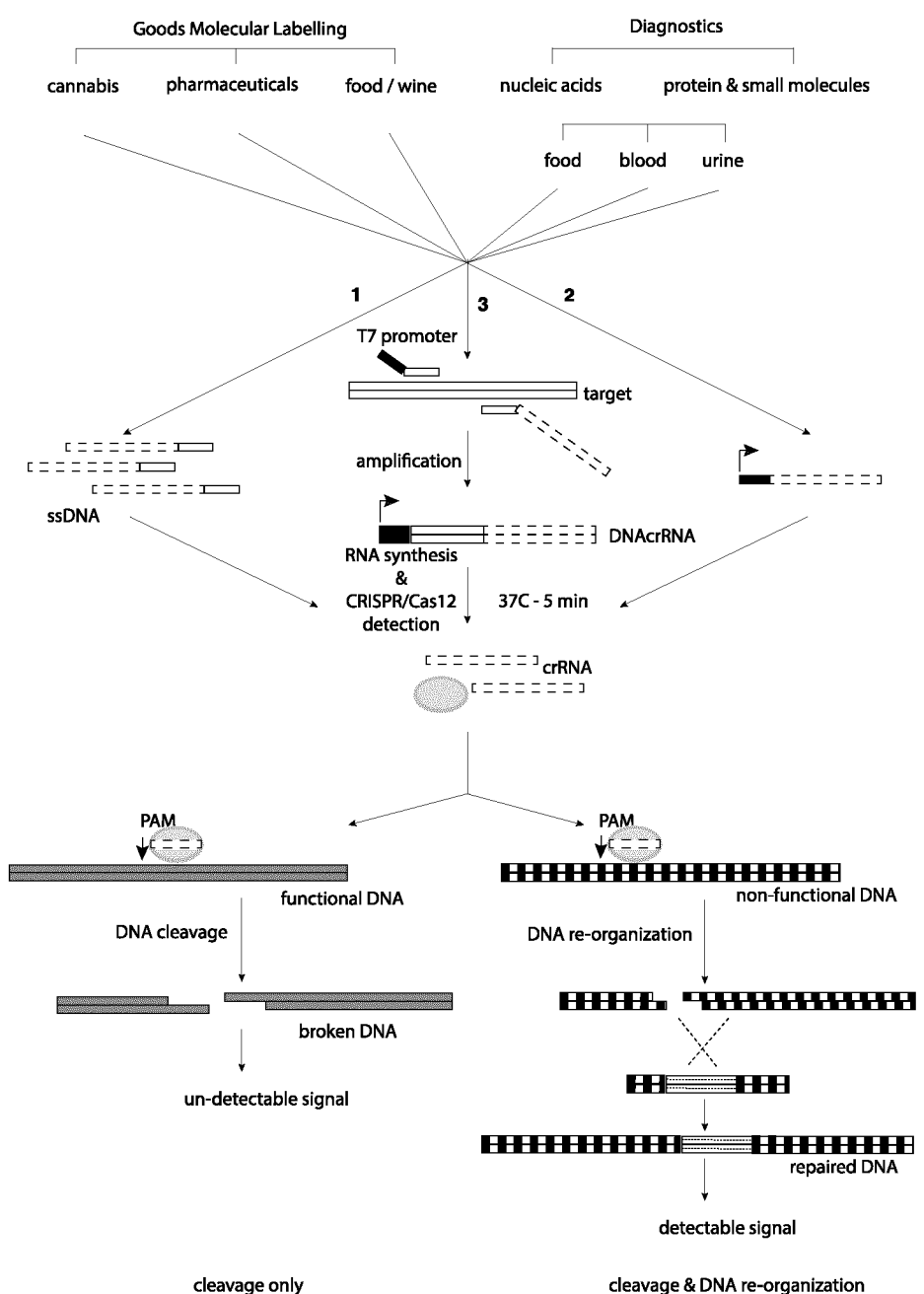

As demonstrated herein, DNA or RNA amplification methods such as isothermal amplification is used in a method to generate crRNAs in a target-dependent manner (FIG. 1). This was done by adding extensions, which encode crRNAs, to the primers used to direct amplification. As demonstrated, the method generated large quantities of DNAcrRNA that when transcribed produces specific composite RNA that is then processed into crRNA by a Cas protein.

As mentioned, the composite RNA is processed into crRNA, and the large quantities of crRNA catalyze the next CRISPR-based step, but only in the presence of the diagnostic target (e.g. primer-target hybridization required). Because crRNA generation is sequence-specific, this process can be multiplexed and therefore allows each target pathogen sequences to catalyze a unique signal, for instance a pre-defined color or electrochemical signal.

The amplification relies on two primers, one carrying a promoter and an annealing portion the second one encoding the crRNA and comprising an annealing portion. With this primer design, non-specific production of the crRNA is minimized and/or avoided.

Accordingly, an aspect provides an oligonucleotide primer pair comprising: a promoter primer comprising, from 5' to 3', a transcriptional promoter, and a proximal detection target segment that has, or is complementary to (e.g. reverse complement), the sequence of a proximal portion of a detection target nucleic acid; and a crRNA primer comprising, from 5' to 3', a crRNA-encoding segment that is sequence encoding a crRNA or the reverse complement of a sequence encoding a crRNA, and a distal detection target segment that has or is complementary to the sequence of a distal portion of the detection target nucleic acid, wherein the target segments in each primer permit amplification from the detection target nucleic acid.

Any suitable transcriptional promoter can be used. For example, any promoter recruiting an RNA polymerase is suitable and can be used, which may include mammalian RNA polymerase using a mammalian promoter. In some embodiments, a promoter that recruits an RNA polymerase is used. In some embodiments, a mammalian promoter that recruits a mammalian RNA polymerase is used. In some embodiments a SP6 promoter, a T7 promoter or a T3 promoter is used. The crRNA primer can be any suitable length. In one embodiment, the crRNA primer is between 30 and 8000 base pairs in length. In another embodiment, the crRNA primer is between 30 and 200 base pairs in length. In addition, when the crRNA is generated from ssDNA (arrow 1, FIG. 1), promoters are not necessary, and any RNA polymerase can be used, for example, SP6, T7, *E. Coli* holoenzyme, and T3.

The primer pairs including multiple primer pairs for multiplexing applications, can be provided in a system for target-specific generation of crRNA-encoding DNA further comprising a DNA polymerase and components for DNA amplification. The system of target-specific generation of a crRNA is agnostic of the amplification method and could be used in conjunction with any suitable DNA or RNA amplification method including PCR, RT-PCR, and isothermal amplification such as using an isothermal amplification method including LAMP, NASBA, RT-RPA, RPA, HDA, RT-HDA, NEAR, Bsu, or IsoPol. In one embodiment the system comprises an isothermal polymerase from an isothermal amplification method such as LAMP, HDA, RT- HDA, NASBA, RT-RPA, RPA, NEAR, Bsu, or IsoPol. In another embodiment, the system comprises a DNA polymerase. In some embodiments, the DNA polymerase is AMV-RT. In another embodiment, the isothermal amplification method is NASBA and the DNA polymerase is AMV-RT.

The primers pairs can be used in a method of target-nucleic acid-specific generation of a crRNA-encoding nucleic acid molecule, optionally a DNA molecule, an embodiment of the method comprising: a) contacting the system of target-specific generation of a crRNA described herein with a sample containing the target nucleic acid; and b) incubating the system contacted with sample of step a) under conditions for target-specific amplification of the target sequence to generate a crRNA-encoding DNA molecule. For example for NASBA, target-specific amplification can be carried out at about 41° C. For RPA and RT-RPA for example, target-specific amplification can be carried out at about 37° C. For HDA and RT-HDA, target-specific amplification can be carried out at about 65° C. For PCR, the skilled person can readily recognize the condition for target-specific amplification including DNA polymerase cycling temperatures.

Polymerases and other components of the amplification reaction can optionally be removed or degraded prior to subsequent steps (e.g. crRNA generation and detection). For example, proteinase K or other proteinase can be added to the reaction mix prior to RePAIR.

The primers pairs can also be used in a method of detecting a target nucleic acid in a sample. In an embodiment, the method comprises: a) providing a sample to be tested for the presence of the target nucleic acid; b) contacting the system of target-specific generation of a crRNA described herein with the sample; c) incubating the system under suitable conditions for target-specific amplification of the target sequence to generate a crRNA-encoding nucleic acid optionally DNA, molecule; d) optionally, separating the crRNA-encoding nucleic acid (e.g. DNA molecule) from remaining primers; e) contacting the crRNA-encoding DNA molecule with an RNA polymerase and components for transcription; f) incubating the crRNA-encoding DNA molecule, RNA polymerase and components for transcription under suitable conditions for generating crRNA; g) contacting the crRNA with a CRISPR-Cas protein; h) incubating the crRNA and CRISPR-Cas protein under suitable conditions for binding of the crRNA to the CRISPR-Cas protein and generating an active CRISPR-Cas effector protein; i) contacting the active CRISPR-Cas effector protein with a signal-generating CRISPR-sensitive reporter, thereby producing a functional signal-generating reporter; j) contacting the functional signal-generating (e.g. previously CRISPR-sensitive) reporter with components for generating signal from the signal-generating reporter; k) incubating the system under suitable conditions for generating a signal from the functional signal-generating reporter; and l) detecting the presence or absence of the signal. In an embodiment, suitable conditions in step c), step e) and/or step f) comprise incubating from about 30° C. to about 70° C., from about 32° C. to about 45° C., or about 35° C. to about 43° C.; or about 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C. In an embodiment, suitable conditions in step g) comprise incubating from about 20° C. to about 45° C., about 25° C. to about 40° C., or about 35° C. to about 43° C.; or about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. In embodiment, components for transcription in step e), and/or step f) comprise buffer, salts, ATP solution, CTP solution, GTP solution, or UTP solution. In an embodiment, step d) comprises using Exonuclease I or VII, at about 37° C. or using ExoSAP or Nuclease S1. One or more steps can be performed together. For example steps a+b+c described above can be performed together followed by d (using for example Exonuclease I or VII or ExoSAP or Nuclease S1, for example at 37° C.), followed by steps e+f+g+h+i then j+k+l can for example one or more of the steps can be performed together (see for example Table 1 and/or 2). As used herein "performed together" means that the all components for each of the listed steps can be included in the same reaction and incubated together.

In one embodiment, separating the crRNA from remaining primers comprises isolating the crRNA-encoding nucleic acid optionally DNA, from the system. In one embodiment, separating the crRNA from remaining primers comprises removing or inactivating the primers.

In one embodiment, the promoter primer comprises a T7 promoter and the RNA polymerase is T7 polymerase. In one embodiment, the promoter primer comprises a T3 promoter and the RNA polymerase is T3 polymerase. In one embodiment, the promoter primer comprises a SP6 promoter and the RNA polymerase is SP6 polymerase. In another embodiment the CRISPR-Cas protein is Cas12a. In an embodiment, the Cas12a is a Cas12a nickase. In another embodiment the crRNA is generated at time of use. In another embodiment, the amplification is isothermal amplification.

In another embodiment, the sample is a biological sample. The biological sample may be obtained for example from a tissue sample, saliva, blood, plasma, sera, stool, urine, semen, sputum, mucous, lymph, synovial fluid, cerebrospinal fluid, ascites, pleural effusion, seroma, pus, skin swab, or mucosal membrane surface.

In another embodiment the sample is an environmental sample. The environmental sample may be, or may be obtained from, a variety of sources including, but not limited to, a food sample, a beverage sample, a surface, a soil sample, a water sample, exposure to atmospheric air or other gas sample, or a combination thereof.

In another embodiment, the target nucleic acid is unpurified or unamplified from the sample prior to the application of the method.

The primer pairs including multiple primer pairs for multiplexing applications can be provided in a kit for detecting a target nucleic acid in a sample. The kit may comprise additional components. In one embodiment, the kit comprises components to isolate a crRNA. In one embodiment, the kit comprises components to remove or inactivate oligonucleotide primers. In one embodiment, the kit comprises a DNA polymerase such as an isothermal polymerase, where the isothermal polymerase is for use in an isothermal amplification method, including, but not limited to HDA, LAMP, NASBA, RPA, NEAR, Bsu, and IsoPol. In another embodiment, the DNA polymerase is AMV-RT. In another embodiment, the isothermal amplification method is NASBA and the DNA polymerase is AMV-RT. In another embodiment, the kit comprises an RNA polymerase and components for transcription. In another embodiment, the kit comprises a CRISPR-Cas protein or a nucleic acid encoding a CRISPR-Cas protein and components for generating a CRISPR-Cas protein. In another embodiment, the kit comprises comprising a signal-generating CRISPR-sensitive reporter and components for generating signal from the signal-generating CRISPR-sensitive reporter. In a further embodiment, the kit comprises the signal-generating CRISPR-sensitive reporter as described herein.

Table 1 includes exemplary components for generating crRNA as further described in the Examples.

II. CRISPR-Mediated Reporting

Figure 3:
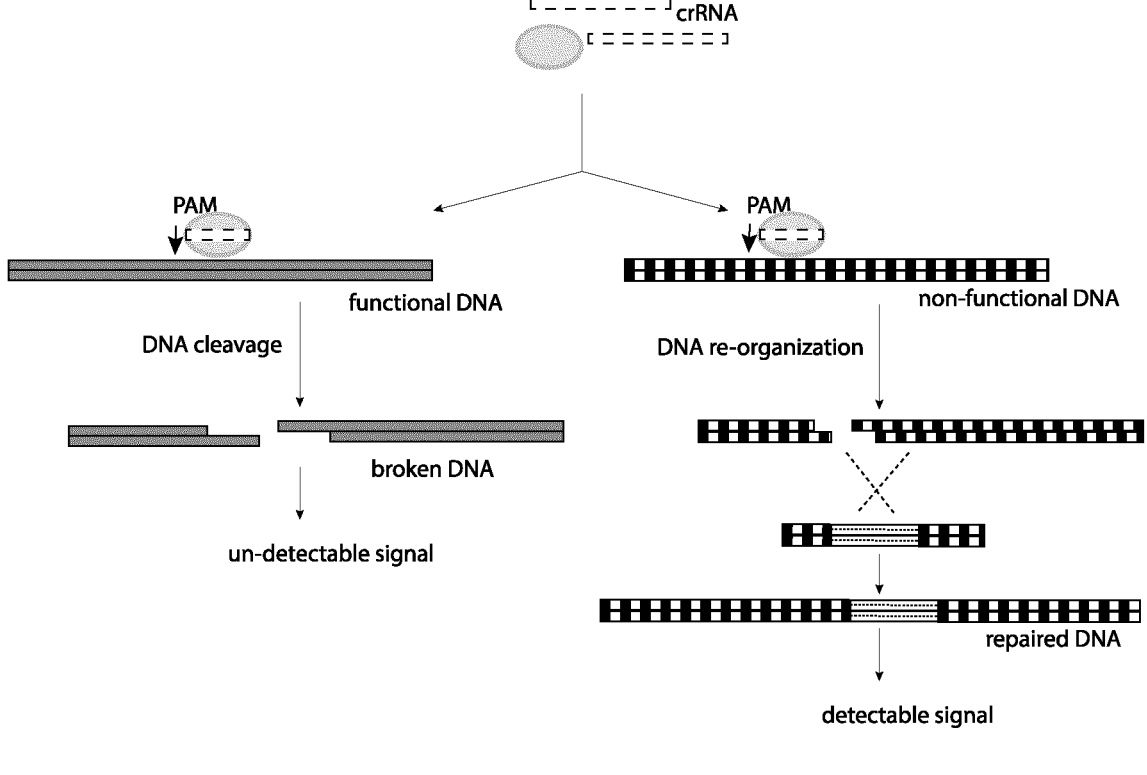

As demonstrated herein, the technology described uses in an embodiment a CRISPR protein called Cas12a (or Cpf1) to catalyze variety of reporting mechanisms. For example, Cas12a has the ability to extract its own crRNA from the longer RNA products generated for example during isothermal amplification. The inventors have exploited this such that the molecular sensors described herein can be stored and distributed using stable DNA encoded tools. Once loaded with the crRNA, Cas12a goes onto to catalyze DNA-based reporters described herein. Examples of two reporter systems are shown in FIG. 3.

Accordingly, another aspect includes a signal-inducing CRISPR-sensitive DNA sensor, the sensor comprising: a non-functional CRISPR-sensitive DNA reporter construct comprising a non-functional expression cassette with at least one CRISPR target site present in the expression cassette, the non-functional expression cassette having a reporter construct upstream-end upstream of the CRISPR target site and a reporter construct downstream-end downstream of the CRISPR target site, and a function-restoring nucleic acid, the function-restoring nucleic acid comprising an upstream flanking end, a function restoring repair insert and a downstream flanking end, wherein the upstream flanking end interfaces with reporter construct upstream end and/or the downstream flanking end interfaces with the reporter construct downstream end and one or both of the flanking ends permit insertion or ligation of the function restoring repair insert into the reporter construct when the CRISPR target site is actuated under sensing condition, thereby producing a functional DNA reporter construct and sensor signal.

The sensor can also comprise at least one function-restoring nucleic acid, the function-restoring nucleic acid comprising a downstream flanking end and a function restoring repair insert, optionally further comprising an upstream flanking end, The CRISPR target site can be inserted or naturally present in the expression cassette.

The function-restoring nucleic acid (e.g. comprising a repair insert) can induce functional repair by various methods. For example, the function-restoring nucleic acid or a portion thereof can interface with the reporter construct by ligation in the presence of a ligase, by recombination, or by strand-displacement repair. The function-restoring nucleic acid can be single stranded or double-stranded depending the reporter system.

Exemplary versions of these reporter systems are shown in Example 2. Elements relating to 3 exemplary versions numbered 1-3 reporter system and referred to in FIGS. 14a-14c, 15a-15g, 16a-16d, and 17a-17g and are further described in Table 2.

In one embodiment, the function-restoring nucleic acid is a ssDNA. The upstream flanking end may hybridize or ligate with the reporter construct upstream end and/or the downstream flanking end may hybridize or ligate with the reporter construct downstream end. In an embodiment, the CRISPR-Cas protein is a nickase.

In another embodiment the function-restoring nucleic acid is a dsDNA.

Another aspect includes a signal-inducing CRISPR-sensitive DNA sensor, wherein the sensor is a non-functional CRISPR-sensitive DNA reporter construct comprising: a promoter; a reporter gene; and a function-blocking region that is flanked by CRISPR-Cas target sites, the non-functional reporter construct having an upstream-end upstream of the function-blocking region and a downstream-end downstream of the function-blocking region, wherein the upstream end interfaces with the downstream end to permit function-restoring repair of the reporter construct when the CRISPR target site is actuated under sensing condition, thereby producing a functional DNA reporter construct and sensor signal.

Another aspect includes a system for detecting a crRNA comprising a signal-inducing DNA sensor described herein as described above; a CRISPR-Cas protein or a nucleic acid encoding a CRISPR-Cas protein and components for generating a CRISPR-Cas protein; and components for repairing the signal-inducing DNA sensor. In one embodiment, the function-restoring nucleic acid is a ssDNA and the components for repair of the sensor comprise an exonuclease, a ligase, and a DNA polymerase. In another embodiment, the function-restoring nucleic acid is a ssDNA and the components for repair of the sensor comprise a DNA polymerase. In one embodiment, the upstream flanking end hybridizes or ligates with the reporter construct upstream end and/or the downstream flanking end hybridizes or ligates with the reporter construct downstream end, and the components for repair of the sensor comprise a DNA ligase and/or the CRISPR-Cas protein is Cas12a.

In one embodiment, the signal-inducing DNA sensor encodes a ribozyme or aptamer and the system further comprises components for transcription.

In another embodiment the signal-inducing DNA sensor encodes a protein and the system further comprises components for transcription and translation. The protein may be selected from a fluorescent protein, preferably green fluorescent protein; a luminescent protein; a chromoprotein; an electrochemically active protein; an affinity protein; and an enzyme, preferably beta-galactosidase.

Another aspect includes a method of detecting a crRNA in a sample, the method comprising: a) exposing the system for detecting a crRNA described herein to the sample; b) incubating the system under suitable conditions for binding of the crRNA to the CRISPR-Cas protein and generating an active CRISPR-Cas effector protein; c) incubating the system under suitable conditions for modification (e.g. cleavage) and repair of the signal-inducing CRISPR-sensitive sensor; d) incubating the system under suitable conditions for expressing the reporter cassette; and e) detecting the presence or absence of signal.

In one embodiment the DNA sensor encodes beta-galactosidase and the signal being detected is a colorimetric signal. In another embodiment the DNA sensor encodes beta-galactosidase and the signal being detected is an electrochemical signal. In another embodiment the DNA sensor encodes a fluorescent protein and the signal being detected is a fluorescent signal. In another embodiment the DNA sensor encodes a luminescent protein and the signal being detected is a luminescent signal.

The signal-inducing DNA sensor described herein can be provided in a kit for detecting a crRNA in a sample. The kit may comprise the cell-free system for detecting a crRNA described herein. The kit may comprise additional components. In one embodiment, the kit comprises a physical substrate and the DNA sensor is applied to the physical substrate. In one embodiment the physical substrate is a porous substrate or flexible materials substrate such as a paper substrate, a fabric substrate, or a flexible polymer-based substrate. In another embodiment the physical substrate is a microtube or chamber. In one embodiment, the system is applied to the physical substrate in a molecular matrix barcode such as a QR-code printed pattern. The QR code approach can involve spatially resolving the optical signal generated by the RePAIR process into a QR code pattern. The pattern may be generated by 1 or multiple reporters.

For example, unique QR codes or other unique patterns can be generated and used to create a mold. For example, as shown in FIG. 23 a laser cut QR code can be cut into a block to serve as a mold for creating an inverted QR code pattern. A liquid setting agent such as glue can be used to fill in the mold and a backing layer that binds to the liquid setting agent either prior to or after setting, can be used to create an inverted QR code pattern. A wax or other hydrophobic material that is generally impermeable to aqueous solutions can be used to create the QR pattern on a suitable reaction substrate, such as a porous filter disk (e.g. polyethylene).

The components for performing a RePAIR (e.g. the non-functional reporter or the function restoring nucleic acid) or for producing crRNA encoding nucleic acid or crRNA can be embedded in the reaction substrate (e.g. the filter paper). Optionally they can be embedded prior to the QR code patterning or more commonly, the components can be embedded subsequent to the application of the wax or hydrophobic material to limit the amount of each component needed. It is possible to position the components as individual components at specific and separate locations on the filter disk such that they are compartmentalized, preventing the components from combining prior to rehydration. The penetration of the components into the pores of the filter disk may also provide better protection against environmental factors. After the needed components have been applied on the porous filter disk, the components are dried (e.g. incubation at 37° C. for 1 hour) or are lyophilized. Thereafter the QR code patterned filter disk can be added onto a variety of surfaces, including for example packaging or onto a product for tracking or ensuring authenticity.

The release of the applied reaction components takes place by adding to the filter disk an aqueous solution that contains all further reaction components needed for the RePAIR and/or crRNA.

This aqueous solution may already also contain the RePAIR nucleic acid or non-functional reporter for completing the RePAIR and/or crRNA encoding nucleic acid or crRNA, depending or what components and/or sensor is included on the filter disc. For example, as shown in Example 16, a RePAIR reporter such as version 3 comprising a non-functional LacZ gene that was embedded in a QR code patterned filter disk and other reagents is successfully rehydrated to produce a positive signal in the presence of the function restoring nucleic acid and LacZ substrate.

A detergent or additive can be added to the aqueous solution. A detergent can for example improve the release of the components present on the filter disk.

The non-functional reporter or function restoring nucleic acid, and optionally the crRNA encoding nucleic acid etc can be embedded. If the non-functional reporter is embedded, the function restoring nucleic acid and/or crRNA encoding nucleic acid which restores function can be used to reveal if the non-functional reporter is indeed embedded and vice versa. The components can be designed for a particular user or entity allowing for anti-counterfeiting and other tracings to be performed.

Also provided in another embodiment, an affixable tracking article, optionally a QR code printed article comprising:
    a reaction substrate;
    a hydrophobic material imprinted on the reaction substrate, optionally in an inverted QR code pattern;
    a CRISPR sensitive reporter, non-functional reporter, a function restoring nucleic acid, sensor, primer, primer pair, ssDNA, and/or DNAcrRNA described herein embedded on the reaction substrate;
    optionally components for performing nucleic acid amplification or function-restoring repair of the signal generating reporter for example one or more components in Table A, 1, 2, 3, and/or 4, wherein the components are dried or lyophilized.

A further aspect includes a package comprising the affixable tracking article of described herein optionally the QR code printed article and the corresponding component for performing a method described herein.

The affixable tracking can comprise a reaction substrate which is a filter disk and a hydrophobic material that is wax.

Multiple systems can be used in combination and/or a pattern where a system is applied to discrete locations can be used.

In one embodiment, the system is applied to multiple discrete locations on the physical substrate. In one embodiment, the kit further comprises one or more additional discrete reporter systems for detecting a crRNA in a sample. The one or more additional systems may be applied to one or more discrete locations on the physical substrate. In one embodiment, a reader detects the crRNA in a sample. In one embodiment, a reader detects the system. In one embodiment, a reader detects the molecular matrix barcode, optionally QR-code printed pattern. In one embodiment, the reader is a smartphone, a webcam, a QR code reader, or any device equipped with a QR-code reader application.

Also provided is a composition comprising any of the components described herein.

In one embodiment, the composition comprises any one of or combinations of any two or more of an oligonucleotide primer or primer pair described herein, a system described herein or any of its components, optionally where the compositions comprises components for effecting a method step described herein, a signal inducing CRISPR-sensitive DNA, nucleic acid, DNAcrRNA, or a molecular barcode described herein.

The composition can comprise one or more components described herein for example in one or more components in Table A, 1, 2, 3 or 4.

Applications

Diagnostics and Sensors

An application of this technology is as a diagnostic. Inventors have shown sensitivity to at least femtomolar range, which exceeds the sensitivity required for most clinical applications. Other related technologies such as toehold switches and CRISPR-based diagnostics (DE-TECTR; SHERLOCK) are generating significant commercialization interest in a bid to serve the growing point-of-care diagnostics market. The method presented here represents a technical improvement over these methods (e.g. DNA-based deployment), can be multiplexed inexpensively and can output to any signal mode (e.g. color, fluorescent, luminescent, electrochemical, enzymatic), and include rapid transcription-only reporters.

The rational design of each sensor translates to a low development cost for sensors and concomitantly opens up a wide range of potential applications. Within health care this could include conventional diagnostic needs, but also includes personalized medicine and orphan diseases. The rational design of sensors also means that new capabilities can be developed rapidly, making this platform ideal for response to outbreaks of emerging and infectious disease. A similar use case of these features can be made for other applications where decentralized sensing would provide an advantage, such agriculture, industry and national security, among others.

Molecular Barcoding

As with diagnostics, the capacity for sequence-specific detection of nucleic acids at the point-of-need can be used to read DNA barcodes embedded into products. Here, much like the optical barcodes used to track consumer goods, the inventors have developed molecular labels to do the same. These invisible labels can be used to tag goods/crates/containers to ensure a secure supply chain. Importantly, these molecular labels can be embedded throughout products to prevent counterfeiting of high value commodities (e.g. drugs), certification of origin (e.g. *cannabis*) and allow for downstream auditing or forensics of contraband. In conjunction with a secure online interface, these tags could carry information to not only authenticate products, but also rapidly provide product manufacturing and shipping details or any number of other features related to the history of the item.

Potential applications include, but are not limited to, the following:
    1. Regulation and compliance. Molecular barcodes provide a physical tag that can be easily linked to an immutable online transaction ledger. Potential markets include tracking legitimate *cannabis*, hazardous waste management or ensuring end-to-end tracking of commodities where black market adulteration is a problem (e.g. conflict oil).
    2. Covert labeling for police and national security applications. Here high-risk and high-value materials (e.g. explosives, money) can be tracked. This also potentially includes labeling of events.

Accordingly, one aspect of the disclosure is a crRNA-encoding single stranded nucleic acid optionally single stranded DNA (ssDNA) molecule comprising a sequence that is the reverse complement of a crRNA molecule. In one embodiment, the crRNA-encoding ssDNA further comprises at its 3' end a detection target segment that has the sequence or is complementary to (e.g. reverse complement) the sequence of a detection target nucleic acid.

Another aspect of the disclosure is a method of generating a crRNA molecule comprising introducing the crRNA-encoding ssDNA into a cell free system comprising components for transcription or into a cell, under suitable conditions for transcription and incubating the system or cell under said conditions to make the CRISPR RNA molecule.

Another aspect of the disclosure is a molecular barcode comprising a crRNA-encoding nucleic acid, optionally DNA molecule, optionally for use in labeling a physical good or material, a location, or an event.

In one embodiment, the crRNA-encoding nucleic acid, optionally DNA, molecule is a ssDNA molecule. In one embodiment the ssDNA is from 30 to 200 bp in length. The ssDNA can also be longer for example when arrayed, for example up to 8 kb in length.

In another embodiment, the crRNA-encoding DNA molecule is a dsDNA molecule and the dsDNA molecule further comprises a transcriptional promoter, such as a T7 promoter, and the promoter is operably linked to the crRNA-encoding DNA. In another embodiment, the transcriptional promoter is a T3 promoter, and the promoter is operably linked to the crRNA-encoding DNA. In another embodiment, the transcriptional promoter is a SP6 promoter, and the promoter is operably linked to the crRNA-encoding DNA.

The crRNA-encoding nucleic acid, optionally DNA, molecule can be ligase-resistant. By using any type of modification at the 5'-OH of the oligonucleotide, phosphorylation of the DNA molecule is impaired, and therefore ligation is impaired. If ligation is impaired, sequencing of oligonucleotides may also be impaired. In another embodiment, the crRNA-encoding nucleic acid molecule, optionally DNA molecule, is ligase-resistant. In another embodiment, the crRNA-encoding nucleic acid, optionally DNA molecule is modified at the 5'-OH of the nucleic acid, optionally DNA, molecule. In another embodiment, the crRNA-encoding nucleic acid, optionally DNA molecule, is ligase-resistant, optionally the crRNA-encoding nucleic acid, optionally DNA molecule is modified at its 5'-OH end.

In one embodiment, the physical good or material is a consumer product or consumer product packaging. The consumer product may include, but is not limited to, *cannabis*, a pharmaceutical drug, a food, a beverage, a fuel, a lubricant, a cosmetic, a perfume, or a gemstone.

In one embodiment, the physical good or material is selected from an explosive, a biological material, a hazardous chemical, hazardous waste, and currency.

Another aspect of the disclosure includes a method for labeling a physical good or material, a location, or an event comprising adding a molecular barcode described herein to a physical good or material, a location, or an event, wherein the molecular barcode is a CRISPR-encoding DNA molecule and the adding comprises applying, embedding, or dispersing. In one embodiment, the molecular barcode is applied to or printed on the surface of the physical good or material. The molecular barcode may be applied to or printed on the surface of the physical good or material, and may be applied to or printed on the surface of the physical good or material in a QR-code printed pattern. In one embodiment the molecular barcode is embedded in the physical good or material.

Another aspect of the disclosure includes a cell-free system for detecting a molecular barcode described herein comprising: a) a RNA polymerase and components for transcription; b) a CRISPR-Cas protein or a nucleic acid encoding a CRISPR-Cas protein and components for generating a CRISPR-Cas protein; c) a signal-generating CRISPR-sensitive reporter; and d) components for generating signal from the signal-generating CRISPR-sensitive reporter, including for example a function restoring repair insert/fragment. The function restoring repair insert can be single stranded or double stranded DNA. Further the function restoring repair insert can be a "supplemented" dsDNA that is provided and processed by the CRISPR-Cas protein and crRNA to provide a single stranded DNA that complements and restores function of a reporter gene as for example shown in the category described as Version 2 (see FIG. 12). In another embodiment, the function restoring repair insert is doubled stranded nucleic acid that when inserted into the non-functional reporter construct, restores activity as for example shown in the category described as Version 3 (see for example FIG. 13).

In one embodiment the RNA polymerase is T7 polymerase. In one embodiment the RNA polymerase is T3 polymerase. In one embodiment the RNA polymerase is SP6 polymerase. In one embodiment the CRISPR-Cas protein is Cas12a. In one embodiment the signal-generating CRISPR-sensitive reporter is the signal-generating CRISPR-sensitive reporter of the disclosure.

In an embodiment, one or more of the RNA polymerase, components for transcription or components for translation and/or one or more of the components are freeze dried. For example, in embodiments where any of the foregoing are provided in a kit, or on a substrate such as a flexible substrate, the foregoing may be provided in freeze dried format. Components could be embedded into a piece of paper disc or substrate in a spatial pattern that is separated by a wax barrier or other hydrophobic materials. Alternatively, the components could be evenly distributed over the substrate, but the reporter result is spatially resolved and concentrated as illustrated in FIG. 10 and optionally arranged as for example, a QR code.

Another aspect of the disclosure includes a method of detecting a molecular barcode described herein, the method comprising: a) providing a sample to be tested for the presence of the molecular barcode; b) contacting the sample with a system for detecting a molecular barcode described herein; c) incubating the sample under conditions to allow transcription of a crRNA from the molecular barcode; d) incubating the sample under conditions to allow binding of the crRNA to the CRISPR-Cas protein to generate an active CRISPR-Cas effector protein; e) incubating the sample under conditions to allow generation of signal from the signal-generating CRISPR-sensitive reporter; and f) detecting the presence or absence of signal. In one embodiment the crRNA is generated at time of use.

Incubating the sample under conditions to allow generation of signal from the signal-generating CRISPR-sensitive reporter, includes for example embodiments using a function restoring repair insert which can be single or doubled stranded DNA.

In one embodiment the sample is an environmental sample. In one embodiment the environmental sample is or is obtained from a food sample, a beverage sample, a surface, a soil sample, a water sample, exposure to atmospheric air or other gas sample, or a combination thereof.

A further aspect of the disclosure is a kit for detecting a molecular barcode described herein. The kit may comprise the cell-free system for detecting a molecular barcode described herein. For molecular barcode applications, kits would be supplied without one or more than one DNA encoded components (X, see table A, below, showing possible kit combinations). In some embodiments, this "missing piece(s)" would be included on the product of interest and would serve as the "key" to authenticate the product.

TABLE A

Possible molecular barcode application kit combinations and or combinations for use in methods, systems compositions, products described herein

| | Kit 1 | Kit 2 | Kit 3 | Kit 4 | Kit 5 | Kit 6 | Kit 7 |
|---|---|---|---|---|---|---|---|
| Target DNA to be detected | X | ✓ | ✓ | ✓ | ✓ | ✓ | ✓ |
| Promoter primer | ✓ | X | ✓ | ✓ | ✓ | ✓ | ✓ |

TABLE A-continued

Possible molecular barcode application kit combinations
and or combinations for use in methods, systems
compositions, products described herein

| | Kit 1 | Kit 2 | Kit 3 | Kit 4 | Kit 5 | Kit 6 | Kit 7 |
|---|---|---|---|---|---|---|---|
| crRNA primer | ✓ | ✓ | X | ✓ | ✓ | ✓ | ✓ |
| Non-functional expression cassette | ✓ | ✓ | ✓ | X | ✓ | ✓ | ✓ |
| Function-restoring nucleic acid | ✓ | ✓ | ✓ | ✓ | X | ✓ | ✓ |
| crRNA encoding ssDNA which can be processed as crRNA or crDNA | ✓ | ✓ | ✓ | ✓ | ✓ | X | ✓ |
| crRNA-encoding nucleic acid e.g. DNAcrRNA | ✓ | ✓ | ✓ | ✓ | ✓ | ✓ | X |

The molecular barcode can for example be any of the "X" pieces not included in the kit.

Each kit can also contain other components such as one or more of RNA pol, Cas, NTPs, a buffer, etc or other component described herein.

In one embodiment, the kit further comprises a physical substrate to which the cell-free system is applied. In one embodiment the physical substrate is a porous substrate or flexible materials substrate such as a paper substrate, a fabric substrate, a flexible polymer-based substrate, or a rigid material. In an embodiment, the rigid material comprises an acrylic chip or glass. In one embodiment, the physical substrate is a microtube or chamber. In one embodiment the system is applied to the physical substrate in a molecular QR-code printed pattern. In one embodiment the system is applied to multiple discrete locations on the physical substrate.

In one embodiment the kit may further comprise one or more additional discrete reporter systems for detecting a crRNA in a sample. The one or more additional systems may be applied to one or more discrete locations on the physical substrate. In one embodiment, the kit further comprises one or more additional discrete reporter systems for detecting a molecular barcode in a sample. The one or more additional systems may be applied to one or more discrete locations on the physical substrate.

The above disclosure generally describes the present application. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

III. EXAMPLES

Example 1. CRISPR-Mediated Reporting a. Cleavage-Only

Figure 2:
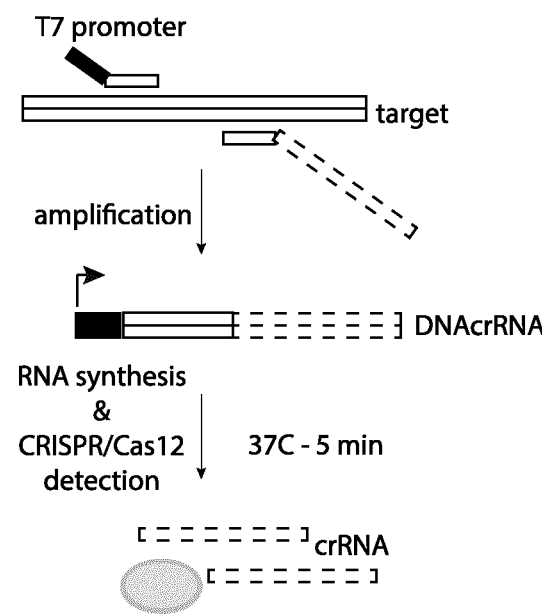

The present Example describes a cleavage-only system embodiment where sequence-specific Cas12a nuclease activity is used to actuate reporters. Here the inventors demonstrate a cleavage-only approach with a signal OFF configuration where crRNA-loaded Cas12a is used to disrupt the expression of a conventional reporter protein (FIG. 4) (see also FIGS. 9 and 10). As schematically shown in FIG. 9A, upon "sensing" of a target nucleic acid and production of a crRNA (see for example FIGS. 1 and 2), the complex Cas/crRNA binds and cleaves a dsDNA reporter labelled to a quencher and a fluorophore. Due to the proximity between these two molecules, fluorescence cannot be detected. After cleavage, the distance between the fluorophore and quencher increases, and fluorescence is now detectable. In FIG. 9b, upon "sensing" of a target nucleic acid and production of a crRNA (see for example FIGS. 1 and 2), the complex Cas/crRNA binds and cleaves a dsDNA reporter labelled to a molecule (fluorophore, gold nanoparticle, enzyme, etc). The DNA fragment carrying the molecule is complementary in sequence to a ssDNA in a ssDNA array. The released DNA binds to the ssDNA in the array, in a sequence specific and localized manner. This system allows resolution of multiplexing on the spatial level.

b. Cleavage and DNA Re-Structuring

Another system embodiment pairs Cas12a cleavage with a DNA re-structuring mechanism. For example, a kit may provide a reporter that has a downstream end comprising a distal portion of a reporter gene, and an upstream end comprising a Cas12a cut site, but lacking a promoter and optionally a proximal portion of the reporter gene (referred to also as a reporter cassette), making it nonfunctional. In the absence of a promoter, RNA polymerase such as T7 RNA polymerase (T7 RNAP), T3 RNA polymerase (T3 RNAP) and SP6 RNA polymerase (SP6 RNAP), cannot bind to initiate transcription and translation, and furthermore the DNA optionally does not code for a functional protein.

The reporter is converted to its functional form through Cas12a-mediated cleavage. Here, crRNA guides Cas12a with its single base pair-resolution to the Cas12a cut site which separates the upstream end from the distal portion of the reporter gene, leaving for example, an overhang for example a 4 or 5 bp overhang. The surrounding molecular solution contains a pre-existing (function restoring) piece of DNA comprising a promoter and optionally a proximal portion of the reporter gene, and having a complementary overhang that can now bind to the overhang and complete the reporter, as well as a T4 ligase to covalently link the modules. With the reporter DNA "repaired", T7 RNAP (or T3 RNAP or SP6 RNAP, depending on the corresponding promoter) can now drive a number of types of optical, enzymatic or electrochemical reporter signals or other downstream processes.

The Cas12a can stay bound to the upstream end preventing re-ligation of the upstream end to the distal portion. The function restoring piece of DNA can comprise a modified PAM sequence or lack a CRISPR target site to prevent re-cutting of the repaired reporter.

As a demonstration of this mechanism the inventors have developed a signal ON system using a colorimetric reporter based on LacZ, which can be read by the naked eye. Here the reporter system is by default non-functional and requires Cas12a cleavage, driven by specific crRNAs, to be made active (FIG. 5). Importantly, this system can be extended, without wishing to be bound by theory, to a very high level of multiplexing, especially using electrochemical outputs.

Moreover, by using a crRNA which targets a different cleavage site within the reporter in combination with a suitable repair piece, the sample reporter gene can be securely re-purposed for molecular barcode applications. For example, in a hypothetical reporter gene that is 250 bp in length, in one example, the crRNA could be designed to target and cleave at residue 25 of the reporter gene and the repair piece would comprise a promoter and residues 1-25 of the reporter gene. In a second example, the crRNA could be designed to target and cleave at residue 50 and the repair piece would comprise a promoter and residues 1-50 of the reporter gene. A signal will only be generated when the correct combination of crRNA and repair piece is used.

The following reaction mix was used for the cleavage repair reaction: Output DNA (e.g. non-functional reporter gene) 20 nM, Proximal DNA 60 nM (e.g. the pre-existing complementary piece of DNA or repair DNA or function restoring DNA), Cas12a 2 uM, MgCl2 10 mM, T4 ligase 0.25 uL (1/40 volume), T4 buffer 0.5 uL (1/10 volume). If producing RNA from DNAcrRNA, add to the same mix: T7 RNA polymerase, NTPs 2 mM, RNASe inhibitor.

Example 2

Exemplary versions of reporter are described that are useful for molecular barcoding applications. All these versions of reporter are useful for diagnostic applications.

In this example, the coding sequence of LacZα present is modified for example by a truncation or an internal deletion to generate a truncated LacZα (trcα). Different truncations are denoted for example as trcα, trc2α, or trc3α, and similar notations are used to denote components related to the indicated truncation e.g. pET15trc3α denotes a pET15 vector comprising the trc3α modification.

A version of the system, herein referred to as "Version 1" is uses homologous direct recombination (HDR; see FIG. 1 bottom right). Components may include a non-functional gene (e.g. the reporter DNA), Cas12a, crRNAtrcα or any of its modifications, a dsDNA to repair, and High-Fidelity (HiFi) Assembly mix (from NEB). The non-functional gene can be pET15trcα or any of its modifications (pET15trc2α, pET15trc3α; see FIGS. 14*a-c*; FIGS. 15*d-g*) which includes a modified reporter gene, the gene could also include other features that make it non-functional, for example, a premature stop codon, etc). The crRNAtrcα or any of its modifications (e.g. crRNAtrc2α and crRNAtrc3α) can be synthesized from a dsDNA encoding the crRNA, for example, dsDNAcrRNAtrcα (see FIG. 15*a*), dsDNAcrRNAtrc2α (see FIG. 15*b*) or dsDNAcrRNAtrc3α (see FIG. 15*c*). The dsDNA to use for repair (e.g. the function restoring nucleic acid) can be, for example, HA40trcα or any of its modification (HA for homologous arms; 40 for the length of the homology arms; and trcα or any of its modification for the gene it is going to repair; see FIG. 15*e* and FIG. 15*g*). The HA40trcα sequence starts on average 40 bp upstream of the cut site, and includes the truncated nucleotides removed from the non-functional gene (e.g. LacZα in the example below) coding sequence, and ends an average 40 bp downstream of the cut. The HiFi Assembly mix is from NEB, e.g. enzymes for Gibson Assembly® which can also be purchased from NEB. Other mixes comprising similar components can also be used. The Version 1 reporter construct can be configured in many different ways, several examples of which are as follows.

pET15trcα: In this embodiment, the coding sequence of LacZα is modified by internal deletion of 55 bp. HA40trcα is a dsDNA that contains the missing 55 bp and 40 bp homology on each side to allow recombination. 30 bp and 50 bp homology on each side also provides for successful recombination. Following a dsDNA break (pET15trcα cut by Cas12a and crRNAtrcα complex) HA40trcα is used for homology directed recombination (see FIG. 14*a*).

pET15trc2α: In this embodiment, the coding sequence of LacZα is modified by internal deletion of 9 bp. The dsDNA used to repair is HA40trc2α and the correcting crRNA is crRNAtrc2α. See FIG. 14*b*.

pET15trc3α: In this embodiment, the coding sequence of LacZα is also modified by internal deletion of 9 bp but at a different position in the coding sequence than in pET15trc2α. The dsDNA used to repair is HA40trc3α and the correcting crRNA is crRNAtrc3α.

The "Version 1" can also be used with Cas12a nickase. For example, recombination may involve a ssDNA that has the same sequence that the HA40trc2α but because it is a ssDNA, the recombination uses either the lagging strand or the non-lagging strand.

Without wishing to be bound by theory, if dsDNAcrRNA is used in this "Version 1" system in the presence of NTPs and T7 RNA polymerase, crRNA would be synthesized, loaded into a Cas protein such as Cas12a, and cleavage followed by recombination would happen (see FIG. 1, arrows 2 and 3).

Another version of reporter system uses strand displacement. A schematic of this version is shown in FIG. 12. As above, "Version 2" can be configured to function in large number of combinations. The components of "Version 2" can include (see also Table 2):

Non-functional gene: such as pET15a, whose coding sequence (white rectangle in the schematic) is fully present but is partially ssDNA in the promoter (black in the schematic). Because of being ssDNA on the promoter region, the coding sequence of LacZα cannot be transcribed and therefore, no protein can be expressed. As shown in FIG. 16*a* and FIG. 16*b*, the region represented by the number #532 is the part that is ssDNA;

crRNA: designed to bind the supplemented dsDNA fragment (described below). When loaded in Cas12a, it releases the exact sequence that will complement the ssDNA portion of the promoter, in this embodiment, the T7 promoter (grey and black on FIG. 12). Exemplary sequences that can be used to synthesize the crRNA are shown in FIG. 16*c*;

Cas12a;

Supplemented dsDNA (grey and black rectangle dsDNA in FIG. 12): upon cleavage of this dsDNA by the crRNA, ssDNA strand is displaced and will complement the non-functional gene (see FIG. 16*d*).

A third version of reporter system is based on the principle of cut and ligate to another DNA (see FIG. 13). The components of "Version 3" can be as shown in Table 2 and they can include:

Non-functional gene: pET15trc3α (non-functional CRISPR-sensitive DNA reporter construct); Cas12a; crRNAtrc3α; proximal DNA fragment for repair (function restoring nucleic acid): includes the 5' coding sequence of LacZα, with the missing piece and an overhang that matched the cleavage generated by Cas12a on the non-functional gene (see FIG. 13); and Ligase: for example commercially available ligase including T4 DNA ligase, Taq ligase, Instant sticky end ligase master mix NEB, all of which can ligate the proximal DNA fragment for repair (function restoring nucleic acid) to the distal DNA (e.g. reporter construct downstream end) resulting in the production of a functional DNA reporter construct and allowing production of a sensor signal, e.g. LacZα.

This system was also demonstrated using DNAcrRNAtrc3α instead of crRNAα, when supplemented with: T7 RNA polymerase; NTPs; and RNASe inhibitors (NEB).

Once the non-functional gene pET15trc3α is cleaved by Cas12a loaded with crRNAtrc3α, the proximal non-functional gene (left part or upstream end of pET15trc3α) stays bound to Cas12a, while the distal side (right part or downstream end of pET15trc3α) is released (FIG. 13). The proximal "repair" fragment can then be ligated to form a functional pET15α.

Recombination with DNAcrRNAtrc3α or directly crRNAtrc3α is shown in FIG. 17*h* and FIG. 17*i*. FIG. 17*h* shows recombination using Version 3 of re-paired in presence of DNAcrRNA. This recombination was carried at 37° C. for 15, 30 or 60 minutes. FIG. 17*i* shows recombination using Version 3 of re-paired in presence of crRNA. This recombination was carried at 37° C. for 15, 30 or 60 minutes. Exemplary components and conditions used are described in Table 2. Sensitivity experiments on DNA-crRNA were carried out at 37° C. (FIG. 17*n* and FIG. 17*o*). In FIG. 17*n*, DNAcrRNA was subjected to RPA. Concentration of DNAcrRNA used in the RPA mix are indicated in the legend, ranging from 173 fM to 1.73 nM. Following RPA, 0.25 uL of the reaction was added to the recombination mix for 1 hr at 37° C. Reading was performed by mixing 0.25 uL of the recombination mix to cell free and read overnight in a plate reader. Maximal sensitivity detected in this experiment was 173 fM. In FIG. 17*o*, same experiment was carried out but without the RPA amplification step. Sensitivity in this assay was about 17.3 pM.

For the recombination system, all the components (see Table 2 below) are mixed in a single tube and incubated between 5 min and 1 hr, typically at 3700, but incubation at room temperature and 5000 can also result in successful recombination.

After the Incubation Time:

An aliquot such as 0.25 uL of the recombination mix is pipetted into the cell free reaction (supplemented with LacZω). The absorbance at 570 nm is monitored over time as an indication of LacZα production (when LacZα is produced it is complemented with LacZω, inducing cleavage of beta-galactosidase as determined, for example, by beta-galactosidase assay (CPRG)).

TABLE 1

| Exemplary components for generating crRNA | |
|---|---|
| Name | Description |
| #470 (ssDNA) SEQ ID NO: 1 | Forward primer "promoter primer": sequence specific to the target pAz and includes a T7 promoter sequence overhang in 5'. See also FIG. 6 top sequence. |
| #683 (ssDNA) SEQ ID NO: 17 | Reverse primer "crRNA primer": sequence specific to the target pAz and includes an overhang sequence in 5' containing the sequence of the spacer targeting pET15trc3a. See also FIG. 7. Once a dsDNA is produced out of the amplification (map and sequence "amplification product pAz using #470-683), in the presence of T7 RNA polymerase and NTPs, a RNA is generated. Because this RNA carries in its sequence the direct repeat, it is cleaved by Cas12a as a crRNA. The 24 nt after the direct repeat are considered as the spacer. The spacer trc3a has the sequence to target pET15trc3a non-functional gene. The crRNA generated by #683 is therefore crRNAtrc3a. |
| crRNA-trc3α | crRNA targeting pET 15trc3a. dsDNAcrRNAtrc3a is the dsDNA that can in vitro produce crRNAtrc3a. In this system, the DNA encoding for the crRNA can come from two different origins. The first one: synthesized by a company such as IDT, dsDNA encoding for the crRNA (see FIG. 17f). The second one: DNAcrRNA can be generated by amplification e.g. DNA coding for crRNAtr3a can be 1) chemically synthesized by a company or 2) generated using PCR from a template that was originally chemically synthesized |
| #518 (ssDNA) | Reverse primer "crRNA primer": sequence specific to the target pAz and includes an overhang sequence in 5' containing the sequence of the spacer targeting pET15a. Once a dsDNA is produced out of the amplification, crRNA is generated. Here the sequence of the spacer targets pET15a for a signal OFF. See FIG. 18. |
| pET 15-trc3α | non-functional reporter missing internal sequence 5'-AACCCTGGC-3' of LacZ for Versions 1 and 3. (SEQ ID NO: 28) |

TABLE 2

Exemplary compositions which can be used with the reporter system versions disclosed herein. Certain components may be omitted for some applications. For example, if producing crRNA from DNAcrRNA, crRNA may be omitted from the composition.

|  | Concentration | Version 1 | Version 2 | Version 3 |
|---|---|---|---|---|
| pET15trc (e.g. α, 2α, 3α) | 20 nM | yes | yes | yes |
| Cas12 | 2 uM | yes | yes | yes |
| MgCl2 | 10 mM | yes | yes | yes |
| crRNA | 6 uM | yes | yes | yes |
| DNAcrRNA | 100 ng | no | no | yes |
| Hifi (NEB) | 25% | yes | no | no |
| ligase | 20 U/uL | no | no | yes |
| KGB (e.g. Table 3) | to final volume | yes | yes | yes |
| HA40trc (e.g. trcα etc) | 60 nM | yes | no | no |
| supplemented dsDNA | 60 nM | no | yes | no |

TABLE 2-continued

Exemplary compositions which can be used with the reporter system
versions disclosed herein. Certain components may be omitted
for some applications. For example, if producing crRNA from
DNAcrRNA, crRNA may be omitted from the composition.

| | Concentration | Version 1 | Version 2 | Version 3 |
|---|---|---|---|---|
| proximal dsDNA | 60 nM | no | no | yes |
| T7 RNA polymerase | 1 uL/50 uL final reaction volume | no | no | yes |
| NTPs | 2 mM | no | no | yes |
| RNAse inhibitors | 1 U/uL | yes | yes | yes |
| Temperature | | 37° C. and 50° C. | 37° C. | RT and 37° C. |

Supplemented dsDNA carries the ssDNA that will bind to ssDNA promoter on the reporter gene. Proximal DNA is going to ligate (and provide repair).

HAtrc is inserting itself in the reporter gene.

TABLE 3 composition of KGB buffer

| Components | Concentration |
|---|---|
| Potassium glutamate | 100 mM |
| Tris acetate | 25 mM |

TABLE 3-continued composition of KGB buffer

| Components | Concentration |
|---|---|
| Beta-mercaptoethanol | 500 uM |
| BSA | 10 mg/mL |

The sequences of nucleic acid of the resent disclosure is shown in Table 4.

TABLE 4

Sequences

Figure 8:
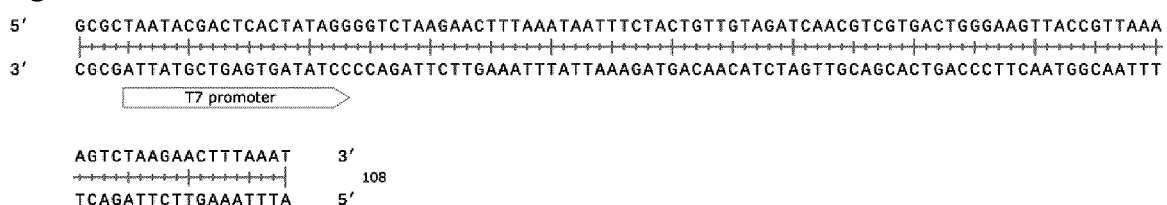
FIG. 8 is a schematic of a dsDNA barcode comprising a T7 promoter operably linked to a crRNA-encoding DNA used to generate the data shown FIGS. 17*h*, 17*n*, and 17*o*, as described in Example 2.

| SEQ ID NO: | Description | Sequence |
|---|---|---|
| 1 | primer binding the target small pAz (See FIG. 6 top sequence) | GCGCTAATACGACTCACTATAGGGCGAAGTTCATATGCTCAACAAGG GCGCCGAGG |
| 2 | primer binding the target small pAz (See FIG. 6 bot sequence) | GCGCTAATACGACTCACTATAGGGCCCGGCGACACGGTCACCTTTA TTCCAGTG |
| 3 | Sequence from FIG. 8, FIG. 15c and FIG. 17f | GCGCTAATACGACTCACTATAGGGGTCTAAGAACTTTAAATAATTTCT ACTGTTGTAGATCAACGTCGTGACTGGGAAGTTACCGTTAAAAGTCT AAGAACTTTAAAT |
| 4 | Sequence from FIG. 15a | GCGCTAATACGACTCACTATAGGGGTCTAAGAACTTTAAATAATTTCT ACTGTTGTAGATATCCCCCTTTCGCCAGCTGGCGTA |
| 5 | Sequence from FIG. 15b | GCGCTAATACGACTCACTATAGGGGTCTAAGAACTTTAAATAATTTCT ACTGTTGTAGATCAACGTCGTGACCCTGGCGTTACCGTTAAAAGTCT AAGAACTTTAAAT |
| 6 | Sequence from FIG. 15 d | tataccatgggcagcagccatcatcatcatcatcacagcagcggcATCGAAGGGCGCAG TGGGGGGGGAGGGTCCATGACCATGATTACGGATTCACTGGCCGTC GTTTTACAACGTCGTGACTGGGAAAACCCTGGCGTTACCCAACTTAA TCGCCTTGCAGCACATCCCCCTTTCGCCGATTCACTGGCCGTCGTTT TCAACGTCGTGACTGGGAAAACCCTGGCGTTACCCAACTTAATCGC CTTGCAGCACATCCCCCTTTCGCCAGCTGGCGTAATAGCGAAGAGG CCCGCACCGATCGCCCTTCCCAACAGTTGCGCAGCCTGAATGGCGA ATGGAGTGGAGGAGGAGGCAGT |
| 7 | Sequence from FIG. 15 e | tataccatgggcagcagccatcatcatcatcatcacagcagcggcATCGAAGGGCGCAG TGGGGGGGGAGGGTCCATGACCATGATTACGGATTCACTGGCCGTC GTTTTACAACGTCGTGACTGGGAAAACCCTGGCGTTACCCAACTTAA TCGCCTTGCAGCACATCCCCCTTTCGCC |
| 8 | Sequence from FIG. 15 f | ACTGGCCGTCGTTTTACAACGTCGTGACTGGGAAGTTACCCAACTTA ATCGCCTTGCAGCACATCCCCCTTTCGCCAGCTGGCGTAATAGCGA AGAGGCCCGCACCGATCGCCCTTCCCAACAGTTGCGCAGCCTGAAT GGCGAAAGTGGAGGAGGAGGCAGTGAAAACTTATACTTCCA |

TABLE 4-continued

| Sequences | | |
|---|---|---|
| SEQ ID NO: | Description | Sequence |
| 9 | Sequence from FIG. 15 g | tataccatgggcagcagccatcatcatcatcatcacagcagcggcATCGAAGGGCGCAG<br>TGGGGGGGGGAGGGTCCATGACCATGATTACGGATTCACTGGCCGTC<br>GTTTTACAACGTCGTGACTGGGAAAACCCTGGCGTTACCCAACTTAA<br>TCGCCTTGCAGCACATCCCCCTTTCGCCAGCTGGCGTAATAGCGAA<br>GAGGCCCGCACCGATCGCCCTTCCCAACAGTTGCGCAGCCTGAATG<br>GCGAAAGTGGAGGAGGAGGCAGTGAA |
| 10 | Sequence from FIG. 16b | CCGCGAAATTAATACGACTCACTATAGGGCCTCTAGAAATAATTTTG<br>TTTAACTTTAAGAAGGAGATATACCATGACCATGATTACGGATTCACT<br>GGCCGTCGTTTTACAACGTCGTGACTGGGAAAACCCTGGCGTTACC<br>CAACTTAATCGCCTTGCAGCACATCCCCCTTTCGCCAGCTGGCGTAA<br>TAGCGAAGAGGCCCGCACCGATCGCCCTTCCCAACAGTTGCGCAG<br>CCTGAATGGCGAATAAAACCCCTCTCTAAACGGAGGGGTTT |
| 11 | Sequence from FIG. 16c | GCGCTAATACGACTCACTATAGGGGTCTAAGAACTTTAAATAATTTCT<br>ACTGTTGTAGATCCAACTCGGCCGATCCGGCCGCGAGTTAAAAGTC<br>TAAGAACTTTAAAT |
| 12 | Sequence from FIG. 16d | TGAACAGCCCTGGTCGGCCCTTACCAACTCGGCCGATCCGGCCGC<br>GAAATTAATACGACTCACTATAGGG |
| 13 | Sequence from FIG. 17b | ACTGGCCGTCGTTTTACAACGTCGTGACTGGGAAGTTACCCAACTTA<br>ATCGCCTTGCAGCACATCCCCCTTTCGCCAGCTGGCGTAATAGCGA<br>AGAGGCCCGCACCGATCGCCCTTCCCAACAGTTGCGCAGCCTGAAT<br>GGCGAAAGTGGAGGAGGAGGCAGTGAAAACTTATACTTCCA |
| 14 | Sequence from FIG. 17d | GCGCTAATACGACTCACTATAGGGCGAAGTTCATATGCTCAACAAGG<br>GCGCCGAGGGCGCCATGGTTTTCGAGCCTGCCTATATCAAGGCCAA<br>TCCCGGCGACACGGTCACCTTTATTCCAGTGGACAAAGGACATAAT<br>GTCGAATCCATCAAGGATATGATCCGTCTAAGAACTTTAAATAATTTC<br>TACTGTTGTAGATCAACGTCGTGACTGGGAAGTTACCGTTAAAAGTC<br>TAAGAACTTTAAAT |
| 15 | Sequence from 17e | gcgaaattaatacgactcactatagggaaataattttgtttaactttaa<br>gaaggagatataccATGACCATGATTACGGATTCACTGGCCGTCGTTCT<br>TCAGCGCCGTGACTGGGAAAACCCTGGCGTTACC |
| 16 | Sequence from FIG. 17g | tataccatgggcagcagccatcatcatcatcatcacagcagcggcATCGAAGGGCGCAG<br>TTGGGGGGGGGAGGGTCCATGACCATGATTACGGATTCACTGGCCGT<br>CGTTTTACAACGTGGGGTGACTGGGAAAACCCTGGCGTTACCCAAC<br>TTAATCGCCTTGCAGCACATCCCCCTTTCGCCAGCTGGCGTAATAGC<br>GAAGAGGCCCGCACCGATCGCCCTTCCCAACAGTTGCGCAGCCTG<br>AATGGCGAAAGTGGAGGAGGAGGCAGTGAA |
| 17 | Sequence from FIG. 7 and FIG. 17m | ATTTAAAGTTCTTAGACTTTTAACGGTAACTTCCCAGTCACGACGTTG<br>ATCTACAACAGTAGAAATTATTTAAAGTTCTTAGACGGATCATATCCT<br>TGATGGATTCGACATTAT |
| 18 | Sequence from FIG. 18 | ATTTAAAGTTCTTAGACTTTTAACGTAAAACGACGGCCAGTGAATCC<br>GATCTACAACAGTAGAAATTATTTAAAGTTCTTAGACGGATCATATCC<br>TTGATGGATTCGACATTAT |
| 19 | Sequence from FIG. 19 a | CCATGATTACGAAGGCTCCACTGCTTCTGCTTGGGA |
| 20 | HA40trca | GTCCATGACCATGATTACGGATTCACTGGCCGTCGTTTTACAACGTC<br>GTGACTGGGAAAACCCTGGCGTTACCCAACTTAATCGCCTTGCAGC<br>ACATCCCCCTTTCGCCAGCTGGCGTAATAGCGAAGAGGCCCG |
| 21 | HA30trca | ATGATTACGGATTCACTGGCCGTCGTTTTACAACGTCGTGACTGGGA<br>AAACCCTGGCGTTACCCAACTTAATCGCCTTGCAGCACATCCCCCTT<br>TCGCCAGCTGGCGTAATAGCG |
| 22 | HA40trc2a | GATTACGGATTCACTGGCCGTCGTTTTACAACGTCGTGACTGGGAAA<br>ACCCTGGCGTTACCCAACTTAATCGCCTTGCAGCACATCCCC |
| 23 | HA40trc3a | GGATTCACTGGCCGTCGTTTTACAACGTCGTGACTGGGAAAACCCT<br>GGCGTTACCCAACTTAATCGCCTTGCAGCACATCCCCCTTTCGCCA<br>GC |
| 24 | Example 12 RePAIR Forward | gcgcTAATACGACTCACTATAGGGGACGCAACCCCAGGAATCCGCCA<br>ATTCAAG |
| 25 | Example 12 RePair Reverse | CAAGCAGAAGCAGTGGAGCCTTCGATCTACAACAGTAGAAATTATTT<br>AAAGTTCTTAGACGAGCAGCCACATTAAGCATATTACACACAC |

TABLE 4-continued

| Sequences | | |
|---|---|---|
| SEQ ID NO: | Description | Sequence |
| 26 | Example 12 MB Forward | gcgcTAATACGACTCACTATAGGGGACGCAACCCCAGGAATCCGCCA ATTCAAG |
| 27 | Example 12 MB Reverse | GGTAACTTCCCAGTCACGACGTTGATCTACAACAGTAGAAATTATTT AAAGTTCTTAGACGAGCAGCCACATTAAGCATATTACACACAC |
| 28 | non-functional reporter missing internal sequence of LacZ for Versions 1 and 3. | 5'-AACCCTGGC-3' |

Example 3. ssDNA Involvement in Recombination

As shown in FIG. 17*l*, ssDNA can be used in a "Version 3" signal-ON system. As shown in FIG. 17*l*, lipET15a used as positive control for functional gene and lipET15trc3α as negative control (non-functional gene). Repair using lipET15trc3α in Version 3 was tested by supplementing the system with varying amounts of the ssDNA primer described in FIG. 7. In this experiment, recombination was detected in the presence of ssDNA down to 10 nM.

Example 4

A molecular sensing platform can be configured in a spatially resolved reporter format. Under this format, reporter signal from activation can be spatially localized to enable an additional layer of multiplexing (see FIG. 10). This format can be used to increase the complexity of DNA-barcoding systems (e.g. each spot is an additional point of confirmation) or to increase the capacity of diagnostics (e.g. each spot is a different disease). Under this format, one or more of the RNA polymerase, components for transcription or components for translation and/or one or more of the components are freeze dried. Components could be embedded into a paper disc or other substrate in a spatial pattern that is separated by a wax barrier or other hydrophobic materials. Alternatively, the components could be evenly distributed over the substrate, but the reporter result is spatially resolved and concentrated as illustrated in FIG. 10, and may be arranged in a pattern that is, for example, a QR code or the like that is detectable by a capable device (see Example 6 below).

Example 5

The nucleic acid, sensor, and system described herein can be used for in vivo modification of a target gene. For example, the modification can involve adding in the target gene's 3'UTR (or any other non-coding RNA sequences) a sequence encoding a crRNA (fullDR-spacer-halfDR) that would allow production of a composite RNA that contains the target RNA and the crRNA. This composite RNA is recognized in the presence of a Cas enzyme and is loaded for downstream applications, for example, in vivo monitoring of processes. For example, when an RNA transcript of the target gene is produced, crRNA is generated, which allows cleavage and repair of, for example, a GFP gene. Therefore, in this example when GFP is detected, an RNA transcript of the target gene was produced.

Example 6. Reading Molecular Barcode

The molecular barcode described herein (see also Example 16 and detailed description) can be embedded in a product or material, for example, be applied or printed on the surface of the physical good material in a QR-code printed pattern. The methods described herein enable the generation of signal from the molecular barcode.

The QR code approach involves spatially resolving the optical signal generated by the RePAIR process into a QR code pattern. The pattern is generated by 1 or multiple reporters. All molecular details are unchanged from the RePAIR process that is described herein. Instead of a simple color change on a paper disc, the color change makes a QR code pattern. By printing the molecular barcode in a QR-code printed pattern, any device capable of reading QR-code, for example a smartphone, a webcam, a QR code reader, or any device equipped with a QR-code reader application, can scan the molecular barcode and, for example, locate, identify, or track the product or material, or determine the authenticity of the product or material.

Example 7 Cell-Based Bioproduction

In biotechnology and pharmaceutical industries, cell culture (e.g. microbial, eukaryotic) is used for the bioproduction of commodities (e.g. polymer precursors, scents, drugs) and protein-based reagents (e.g. vaccines, antibodies). This process involves the expansion of cell populations and then induction of the biosynthetic/production process. An example of this is the addition of IPTG (Isopropyl β-d-1-thiogalactopyranoside) to *E. coli* cell culture, which induces the activation of gene expression and the concomitant synthesis of the product-of-interest. This approach requires the physical addition of IPTG, which is costly ($90/g), and manual monitoring of cell density to ensure that cultures are induced at the appropriate time point.

The in vivo application of the CRISPR technology described herein could be used to replace IPTG by allowing production of product to be induced by the expression of a gene that is correlated to quorum or other cell density-related transcripts. Here the cell would be engineered to include an engineered 3' UTR coding for a crRNA into these transcripts. Using this approach, cells could essentially induce themselves, enabling automation of production and more cost effective production.

Mechanism: Upon expression of the cell-density related endogenous gene, Cas12 would load the engineered crRNA from the 3' UTR, which could direct CPF1 in a sequence-specific manner to gene promoters and drive the expression of biosynthetic enzymes.

Example 8 Regenerative Medicine

The ability of the CRISPR technology to synchronize an engineered gene circuit to the expression of an endogenous gene (e.g. developmental program) has in regenerative medicine.

a) Differentiation. In the differentiation of stem cells to neurons, the expression of a neuron-specific gene (with an engineered 3' UTR) would lead to the loading of CPF1 with a crRNA. Loading provides gene specific targeting of CPF1. CPF1-targeted genes could be induced to express (e.g. other neuronal genes to drive cell state to a neuronal end point more quickly) or to repress non-neuronal cell state gene (e.g. turn off pluripotent genes like Oct4).

b) Culture purity. Differentiation of cells to a specific cell type (e.g. myocardial cells) for use in regenerative medicine often requires a high level of cell homogeneity. With the presently described CRISPR technology, genes that are associated with desired/undesired cell states could be engineered to encode crRNAs in their 3' UTRs. This could be used to drive the expression of a drug selection marker (e.g. puromycin resistance) that would allow only cells expressing the genes of the desired state to survive puromycin exposure. Conversely, this could be used to induce the expression of a cytotoxic gene (e.g. caspase) to kill off cells in the undesired state and improve cell purity.

Example 9

Therapeutic

With the advent of cell-based therapeutics, there are exciting potential applications of the presently described CRISPR technology in vivo. Here an engineered therapeutic cell (CAR T or gut microbe) could be designed to produce/secrete therapeutics when it finds its target (e.g. cancer niche or gut inflammation). The crRNA would be engineered into the 3' UTR of gene associated with the cell's response to the trigger of interest (e.g. cellular response to the anoxic tumor environment or gut inflammation).

Example 10

Amplification prior to detection, for example amplification can proceed the methods described in any of Examples 1 to 5. All steps described in Examples 1 to 5 can be preceded by an amplification step. As shown in FIGS. 17j and 17k, cleavage and DNA reorganization can be successfully performed starting with DNA (FIG. 17j) or RNA (FIG. 17k) using HDA amplification. Sensitivity achieved is for example of 32 fM and 17 pM respectively for DNA and RNA. The method can detect a synthetic DNA (j) or RNA (k) target. The sequence is arbitrary—the system can be programmed to detect any sequence of interest.

Example 11—Sensitivity of DNAcrRNA in the Cis-Cleavage System

The cis-cleavage is an alternative system to output the result of the amplification (as depicted in FIG. 9a, 9b, 19a).

In contrast to trans-cleavage (aka collateral cleavage), cis-cleavage is sequence-specific, allowing the sequence-specific cleavage of a molecular beacon.

The indicated concentrations (FIG. 19b) of DNAcrRNA were added to the cis-cleavage mix. The cis-cleavage mix contains: Cas12a (4 uM), MgCl2, NTPs, T7 RNA polymerase, and Molecular Beacon (1 uM). The Molecular Beacon (MB) is dsDNA comprising a CRISPR target sequence which corresponds to the spacer present in the crRNA. Upon cis-cleavage of the MB by the activated Cas12a, fluorescence will be detectable.

Molecular Beacon design: As shown in FIG. 19a, the top strand has a fluorophore attached and the bottom strand has a quencher attached. The cleavage site is close enough to the fluorophore and quencher that the remaining dsDNA linking them becomes unstable. Upon cleavage, the fluorophore and quencher will separate, enabling fluorescence to be detected.

Sensitivity obtained: The sensitivity of detection of DNA-crRNA using a molecular beacon and various concentrations of DNAcrRNA in the cis-cleavage mix, without amplification and without the use of a cell free expression system, is shown in FIG. 19b. FIG. 19b shows the detection of target DNAcrRNA using the molecular beacon-based cleavage reporter mechanism.

Example 12: DNA Detection

Detection of Deformed Wing Virus (DWV) Synthetic dsDNA:

Synthetic dsDNA (DNAcrRNA) at different concentrations were used in HDA amplification using primers of SEQ ID NO: 24 and SEQ ID NO: 25. After 3 hr at 65° C., proteinase K treatment, 0.25 uL was transferred in the Version 3 RePAIR solution. The following reaction mix was used for the cleavage repair reaction: Output DNA (e.g. non-functional reporter gene pET15trc3α) 20 nM, Proximal DNA 60 nM (e.g. the pre-existing complementary piece of DNA or repair DNA or function restoring DNA), Cas12a 2 uM, MgCl2 10 mM, T4 ligase 0.25 uL (1/40 volume), T4 buffer 0.5 uL (1/10 volume), T7 RNA polymerase, NTPs 2 mM, RNAse inhibitor.

1 hr post RePAIR at 37° C., 0.5 uL was added to the cell free transcription/translation mix. FIG. 20a shows absorbance at 570 nm, demonstrating RePAIR of the alpha subunit of the LacZ gene, with as little target dsDNA as 50 aM.

Using the same synthetic dsDNA, HDA was performed with cis-cleavage system as an output (using primers of SEQ ID NO: 26 and SEQ ID NO: 27). After proteinase K treatment, the HDA amplification product was transferred in the cis-cleavage mix described in Example 11. As shown in FIG. 20b, the cis-cleavage system achieves attomolar sensitivity.

Detection of Deformed Wing Virus (DWV) Viral cDNA:

Using cultured viruses, RNA was extracted and cDNA was generated. FIG. 21a shows the result of the specific detection of the DWV cDNA using amplification HDA followed by RePAIR and cell free.

Example 13: RNA Detection from Synthetic RNA

Detection of synthetic DWV RNA: in vitro transcription was performed on synthetic dsDNA encoding for a fragment of the DWV genome. Once synthetic RNA was purified, RTHDA was performed followed by proteinase K and the cis-cleavage system described in Example 11. As shown in FIG. 22, femtomolar concentrations of RNA can be detected.

Example 14: RNA Detection from Samples

DWV RNA detection: RNA was obtained from RNA extraction of cultured DWV virus. 1 uL of this purified RNA was used in a 10 uL final reaction of RTHDA kit (NEB). Primers for the HDA amplification contain the barcode for the following RePAIR step (or molecular beacon). Following an amplification of 3 hr incubated at 65° C., Proteinase K was performed on the samples (2 uL samples+0.6 uL of Proteinase K). IAPV virus is used as a control.

It is which crRNA is encoded in the primer that determines which output. If it targets a MB: it will be used for fluorescence. If targets a protein that has to be expressed in cell free: output can be protein expression of a fluorometric protein, or expression of a colorimetric protein, or it can be expression of an electrochemical enzyme.

If the primers used in the amplification step enabled a colorimetric output using the RePAIR system of Version 3], 0.25 uL of the sample was added to the RePAIR mix for 1 hour (e.g. table 2 mix). Then 0.5 uL was added in the cell-free mix. The results are shown in FIG. 23a.

If the primers used in the amplification enabled the use of the cis-cleavage activity of the Cas enzyme, the sample was added to a mix containing the cis-cleavage system. The results are shown in FIG. 23b.

Example 15: ssDNA

A ssDNA containing a sequence coding for a crRNA (for example as the primers used above for amplification e.g. SEQ ID NO: 17) can be used directly and/or for the generation of crRNA. A crRNA can be generated through the T7 RNA polymerase. There is no need for a promoter for the T7 RNA pol to function.

The crRNA can be detected using a suitable detection system such as the RePAIR systems described above, or using a molecular beacon, depending on the crRNA.

The crRNA can be generated in the RePAIR systems described by including the ssDNA, T7 RNA polymerase, NTPs 2 mM, and RNAse inhibitors in a RePAIR solution described above (e.g. Output DNA (e.g. non-functional reporter gene pET15trc3α) 20 nM, Proximal DNA 60 nM (e.g. the pre-existing complementary piece of DNA or repair DNA or function restoring DNA), Cas12a 2 uM, MgCl2 10 mM, T4 ligase 0.25 uL ($\frac{1}{40}$ volume), T4 buffer 0.5 uL ($\frac{1}{10}$ volume)).

Example 16. Molecular QR-Code or Other

The QR code approach involves spatially resolving the optical signal generated by the RePAIR process into a QR code pattern. The pattern is generated by 1 or multiple reporters. All molecular details are unchanged from the RePAIR process that is described herein. Instead of a color change on a paper disc, the color change makes a QR code pattern.

As shown in FIG. 24, a laser cut QR code was cut into a block to serve as a mold for creating an inverted QR code pattern. A liquid setting agent such as glue was used to fill in the mold and a backing layer that binds to the liquid setting agent was placed on the glue layer prior to the glue setting, and used to create an inverted QR code pattern (e.g. the laser cutter was used to make a stamp and the stamp was used to imprint the glue). Printed wax (e.g. Xerox Phaser 8500) was used to create the QR pattern on a suitable reaction substrate, such as a porous filter disk (e.g. polyethylene).

The RePAIR components (e.g. Table A and/or Table 2) were added to available portions of the filter disk that were not covered by wax. The reagents were dried. Subsequently, the reaction portion of the QR coded filter disk was rehydrated by providing water, +/− barcode and LacZ substrate, producing a blue colour.

In an embodiment, all components required (except the barcode) are present on the QR code. If the barcode is provided with rehydrate, a color signal is generated.

Results are shown in FIGS. 24A and 24B.

Barcode can be added to the product as a paper product. Final receiver could apply the barcode mix. Alternatively, the barcode mix could be added to the product and the receiver could apply the barcode.

As shown herein, adding the product of the RePAIR on the QR enables a colorimetric QR to appear. Enabling the confirmation that the product received is the correct one.

REFERENCES

Curtis, K. A. et al. Isothermal amplification using a chemical heating device for point-of-care detection of HIV-1. PLoS ONE 7, e31432 (2012).

Yan, L. et al. Isothermal amplified detection of DNA and RNA. Mol Biosyst 10, 970-1003 (2014).

Gan, W. et al. A filter paper-based microdevice for low-cost, rapid, and automated DNA extraction and amplification from diverse sample types. Lab Chip 14, 3719-3728 (2014).

Linnes, J. C. et al. Paper-based molecular diagnostic for *Chlamydia trachomatis*. RSC Adv 4, 42245-42251 (2014).

Pardee, K. et al. Rapid, Low-Cost Detection of Zika Virus Using Programmable Biomolecular Components. Cell 165, 1255-1266 (2016).

Gootenberg, J. S. et al. Nucleic acid detection with CRISPR-Cas13a/C2c2. Science 356, 438-442 (2017).

Gootenberg, J. S. et al. Multiplexed and portable nucleic acid detection platform with Cas13, Cas12a, and Csm6. Science 360, 439-444 (2018).

Chen, J. S. et al. CRISPR-Cas12a target binding unleashes indiscriminate single-stranded DNase activity. Science 360, 436-439 (2018).

Mousavi, S. P. et al. A multiplexed, electrochemical interface for gene-circuit-based sensors. Nat. Chem. 12, 48-55 (2020).

The invention claimed is:

1. A method of target-nucleic acid-specific generation of a crRNA-encoding nucleic acid in a sample putatively containing the target nucleic acid, the method comprising:

a. providing the sample putatively containing the target nucleic acid;

b. contacting the sample with a system, the system comprising:

i) a primer pair comprising a promoter primer and a crRNA primer, the promoter primer comprising, from 5' to 3', a transcriptional promoter, and a proximal detection target segment that has, or is complementary to, the sequence of a proximal portion of the target nucleic acid, and the crRNA primer comprising, from 5' to 3', a crRNA encoding segment that is a sequence encoding a crRNA or the reverse complement of a sequence encoding a crRNA, and a distal detection target segment that has, or is complementary to, the sequence of a distal portion of the target nucleic acid, wherein the target segments in each primer permit amplification from the detection target nucleic acid;

ii) a polymerase; and iii) components for nucleic acid amplification; and c. incubating the sample and the system of step b. under conditions for target-specific amplification of the target sequence to generate a crRNA-encoding nucleic acid.

2. The method of claim 1 for detecting a target nucleic acid in a sample, the method further comprising:

d. optionally, separating the crRNA-encoding nucleic acid, optionally wherein separating the crRNA-encoding nucleic acid comprises i) isolating the crRNA-encoding nucleic acid, from the system; or ii) inactivating the primers;

e. contacting the crRNA-encoding nucleic acid with an RNA polymerase and components for transcription;

f. incubating the crRNA-encoding nucleic acid, RNA polymerase and components for transcription under conditions for the generation of a crRNA;

g. contacting the crRNA with a CRISPR-Cas protein, optionally the CRISPR-Cas protein Cas12a;

h. incubating the crRNA and CRISPR-Cas protein under conditions to allow the binding of the crRNA to the CRISPR-Cas protein to generate an active CRISPR-Cas effector protein;

i. contacting the active CRISPR-Cas effector protein with a signal-generating CRISPR-sensitive reporter;

j. incubating the CRISPR-Cas effector protein and signal-generating CRISPR-sensitive reporter under conditions to allow the generation of signal from the signal-generating CRISPR-sensitive reporter; and k. detecting the presence or absence of signal.

3. The method of claim 1, wherein the sample is a) a biological sample, or b) an environmental sample, c) a sample comprising a barcode, or a combination thereof, and/or wherein the target nucleic acid is purified or amplified from the sample prior to the application of the method.

4. The method of claim 3 wherein the biological sample is obtained from a tissue sample, saliva, blood, plasma, sera, stool, urine, semen, sputum, mucous, lymph, synovial fluid, cerebrospinal fluid, ascites, pleural effusion, seroma, pus, skin swab, or mucosal membrane surface, or the environmental sample is or is obtained from a food sample, a beverage sample, a surface, a soil sample, a water sample, exposure to atmospheric air or other gas sample.

5. The method of claim 1, wherein the polymerase is a DNA polymerase, optionally selected from Bsu, IsoPol, AMV-RT or Q5, or any DNA polymerase, suitable for use in isothermal amplification, optionally selected from HDA (Helicase-dependent amplification), LAMP (Loop-mediated Isothermal Amplification), NASBA (Nucleic Acid Sequence-Based Amplification), RPA (Recombinase Polymerase Amplification), NEAR (Nicking Enzyme Amplification Reaction), or suitable for PCR or combinations thereof.

6. The method of claim 1, wherein target nucleic acid is an RNA and the polymerase is a reverse transcriptase optionally AMV-RT.

7. The method of claim 2, wherein a. the promoter primer comprises a T7 promoter and the RNA polymerase is T7 polymerase;

b. the promoter primer comprises a T3 promoter and the RNA polymerase is T3 polymerase; or c. the promoter primer comprises a SP6 promoter and the RNA polymerase is SP6 polymerase.

8. The method of claim 2, wherein the signal-generating CRISPR-sensitive reporter is a molecular beacon (MB), optionally wherein the molecular beacon which comprises a CRISPR sensitive nucleic acid linker, a fluorophore and a quencher, wherein the CRISPR sensitive nucleic acid linker is double stranded and optionally wherein the fluorophore and the quencher are opposite.

9. The method of claim 2, wherein the signal-generating CRISPR-sensitive reporter is a CRISPR-sensitive DNA sensor, and the method further comprises in step i. contacting the active CRISPR-Cas effector protein with components for function-restoring repair of the signal-generating reporter and incubating the active CRISPR-Cas effector protein, signal-generating CRISPR-sensitive reporter, and components under conditions to allow a function restoring repair of the signal generating reporter.

10. The method of claim 9, wherein the CRISPR-sensitive DNA sensor comprises:

a. a non-functional CRISPR-sensitive DNA reporter construct comprising a non-functional expression cassette with at least one CRISPR target site inserted or naturally present in the expression cassette, the non-functional expression cassette having a reporter construct upstream end upstream of the CRISPR target site and a reporter construct downstream end downstream of the CRISPR target site, and b. at least one function-restoring nucleic acid, the function-restoring nucleic acid comprising a downstream flanking end and a function restoring repair insert, optionally an upstream flanking end, optionally comprising a promoter, wherein the upstream flanking end interfaces with the reporter construct upstream end and/or the downstream flanking end interfaces with the reporter construct downstream end and one or both of the flanking ends permitting insertion or ligation of the function restoring repair insert into/to the reporter construct when the CRISPR target site is actuated under sensing condition, thereby producing a functional DNA reporter construct and sensor signal, or the CRISPR-sensitive DNA sensor comprises:

a. a non-functional DNA reporter construct comprising a non-functional expression cassette, the non-functional expression cassette having a single stranded part;

b. at least one function-restoring nucleic acid optionally supplemented dsDNA, the function-restoring nucleic acid comprising:

i. a CRISPR target site inserted or naturally present in the function restoring nucleic acid, and ii. a function restoring repair insert complementary to the single stranded part of the non-functional DNA reporter construct, the function restoring insert being releasable upon CRISPR mediated cleavage of the function restoring nucleic acid;

wherein the function restoring repair insert interfaces (hybridizes) with the reporter construct single stranded part permitting insertion or ligation of the function restoring repair insert into/to the reporter construct when the CRISPR target site is actuated under sensing condition, thereby producing a functional DNA reporter construct and sensor signal; or the CRISPR-sensitive DNA sensor comprises a non-functional CRISPR-sensitive DNA reporter construct, the reporter construct comprising:

a. a promoter, b. a reporter cassette, c. a function-blocking region optionally in the promoter, or within a transcription start site or in a coding region of the reporter cassette, d. CRISPR-Cas target sites that flank the function blocking region;

e. a reporter construct upstream end upstream of the function-blocking region; and f. a reporter construct downstream end downstream of the function-blocking region;

wherein the upstream end is capable of interfacing with the downstream end to permit function-restoring repair of the reporter construct when the CRISPR target sites are actuated under sensing condition, thereby producing a functional DNA reporter construct and sensor signal.

11. The method of claim 2, wherein the signal-generating CRISPR-sensitive reporter in step i. is a CRISPR-sensitive DNA sensor comprising:

i) a non-functional CRISPR-sensitive DNA reporter construct comprising a non-functional expression cassette with at least one CRISPR target site inserted or naturally present in the expression cassette, the non-functional expression cassette having a reporter construct upstream end upstream of the CRISPR target site and a reporter construct downstream end downstream of the CRISPR target site, and ii) at least one function-restoring nucleic acid, the function-restoring nucleic acid comprising a downstream flanking end and a function restoring repair insert, optionally an upstream flanking end, wherein the upstream flanking end interfaces with the reporter construct upstream end and/or the downstream flanking end interfaces with the reporter construct downstream end and one or both of the flanking ends permitting insertion or ligation of the function restoring repair insert into/to the reporter construct when the CRISPR target site is actuated under sensing condition, thereby producing a functional DNA reporter construct and sensor signal;

and the method further comprises in step i incubating the CRISPR-Cas effector protein and signal-generating CRISPR-sensitive reporter under conditions to allow function restoring repair of the signal-generating CRISPR-sensitive reporter.

\* \* \* \* \*